(12) United States Patent
Zhang et al.

(10) Patent No.: US 7,442,685 B2
(45) Date of Patent: Oct. 28, 2008

(54) DOT1 HISTONE METHYLTRANSFERASES AS A TARGET FOR IDENTIFYING THERAPEUTIC AGENTS FOR LEUKEMIA

(75) Inventors: Yi Zhang, Chapel Hill, NC (US); Qin Feng, Houston, TX (US); Yuki Okada, Carrboro, NC (US); Guoliang Xu, Shanghai (CN)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 341 days.

(21) Appl. No.: 10/866,908

(22) Filed: Jun. 14, 2004

(65) Prior Publication Data

US 2005/0048634 A1 Mar. 3, 2005

Related U.S. Application Data

(60) Provisional application No. 60/478,497, filed on Jun. 13, 2003.

(51) Int. Cl.
*C07K 1/00* (2006.01)
(52) U.S. Cl. ............................... 514/12; 530/350
(58) Field of Classification Search ............... 514/12
See application file for complete search history.

(56) References Cited

U.S. PATENT DOCUMENTS

| 6,251,594 | B1 | 6/2001 | Gonzalgo et al. |
| 6,555,329 | B2 | 4/2003 | Jenuwein et al. |
| 2003/0157532 | A1 | 8/2003 | Jenuwein et al. |
| 2004/0053233 | A1* | 3/2004 | Lorens et al. ............... 435/6 |

FOREIGN PATENT DOCUMENTS

| WO | WO 03/016497 A2 | 2/2003 |
| WO | WO03/016497 A2 * | 2/2003 |
| WO | WO 03016497 A2 * | 2/2003 |

OTHER PUBLICATIONS

Feng et al. (Current Biology 2002; 12: 1052-1058).*
Accession No. AAC08316, NCBI Database.
Accession No. AF509504, NCBI Database.
Accession No. AAF54122, NCBI Database.
Accession No. AAN13378, NCBI Database.
Accession No. AAN13379, NCBI Database.
Accession No. AAN13380, NCBI Database.
Accession No. BAB84946, NCBI Database.
Accession No. CAA90610, NCBI Database.
Accession No. EAA03558, NCBI Database.
Accession No. EAA33634, NCBI Database.
Accession No. NP_010728, NCBI Database.
Accession No. NP_115871, NCBI Database.
Accession No. NP_510056, NCBI Database.
Accession No. NP_649655, NCBI Database.
Accession No. NP_731084, NCBI Database.
Accession No. NP_731085, NCBI Database.
Accession No. NP_731083, NCBI Database.
Accession No. Q8TEK3, NCBI Database.
Accession No. Q04089, NCBI Database.
Accession No. XP_125730, NCBI Database.
GenBank Accession No. BF982417 (Jan. 22, 2001).
GenBank Accession No. BF507396 (Dec. 6, 2000).
Dlakic, M.; "Chromatin silencing protein and pachytene checkpoint regulator Dot1p has a methyltransferase fold," *Trends in Biochemical Sciences* 26:7 405-407 (Jul. 2001).
Feng et al.; "Methylation of H3-Lysine 79 is mediated by a new family of HMTases without a SET domain," *Current Biology* 12: 1052-1058 (Jun. 2002).
Lacoste et al., "Disruptor of Telomeric Silencing-1 is a chromosome-specific histone H3 methyltransferase," *Journal of Biological Chemistry* 277:34 30421-30424 (2002).
Min et al., "Structure of the catalytic domain of human DOT1L, a non-set domain nucleosomal histone methyltransferase," *Cell* 112: 711-723 (Mar. 2003).
Ng et al., "Lysine methylation within the globular domain of histone H3 by Dot1 is important for telomeric silencing and Sir protein association," *Genes & Development* 16: 1518-1527 (2002).
San-Segundo et al., "Role for the silencing protein Dot1 in Meiotic checkpoint control," *Molecular Biology of the Cell* 11 3601-3615 (Oct. 2000).
Singer et al., "Identification of high-copy disruptors of telomeric silencing in *Saccharomyces cerevisiae*," *Genetics* 150 613-632 (Oct. 1998).
Van Leeuwen, et al., "Dot1p modulates silencing in yeast by methylation of the nucleosome core," *Cell* 109 745-756 (Jun. 2002).
Zhang, Yi, (Oral Presentation) "hDOT1L, a histone methyltransferase without a SET domain is involved in leukemogenesis," 28th Lineberger Cancer Symposium, "Epigenetics, Chromatin and Cancer," UNC-CH, Chapel Hill, NC, USA (Apr. 20, 2004).

* cited by examiner

*Primary Examiner*—Brandon J Fetterolf
(74) *Attorney, Agent, or Firm*—Myers Bigel Sibley & Sajovec, P.A.

(57) ABSTRACT

The present invention provides polypeptides with histone H3 lysine 79 methyltransferase activity as well as nucleic acids encoding the same. Also provided are methods of using the polypeptides and nucleic acids of the invention in screening assays to identify compounds of interest. Further provided are diagnostic methods for leukemia and prognostic methods to predict the course of the disease in a subject.

12 Claims, 27 Drawing Sheets

```
yDOT1  290 ETILPDLNASFDNSDTKGFVNAIN LYNKMIREIPRQR-- IIDHLETIDKIPRSFIHDFLHIVY
cDOT1L  88 VPLPSDAVVGNPDKFSQ-YIDALN LKLAHPDVLSRVP--AKHHEITSTRLCSLTVAIKLAELA
hDOT1L  53 LAMENYVLIDYDTKSFESMQRLCD KYNRAIDSIHQLWKGTTQPM-KLNTRPSTGLLRHILQQV
dDOT1L  58 SAFEETNLHQIDTACYKTMTGLVD RFNKAVDSIVALEKGTSLPAERLNKFAHPSLLRHILQLV yDOT1       TRSIHPQ ANK LKH Y KAFSNY VYGE LLPNFLSDVYQQCQLKKG D T FMDLGSGVGNC VQA A LEC
cDOT1L      YRFSVPD ANV LRH Y AVGTST VYGE LHCSQMASFVDQLNMGPS D Y FMDLGSGIGHL MNF V AA YA
hDOT1L      YNHSVTD PFK LNN Y EPFSPE VYGE TSFDLVAQMIDEIKMTDD D L FVDLGSGVGQV LQV A AA T
dDOT1L      YNAAVLD PKL NQY EPFSPE VYGE TSYELVQQMLKHVTVSKE D T E IDLGSGVGQV LQM A GSF
                            POST I
yDOT1       GCALSF GCE IMD DASDLT ILQYEELKKRCKL YGMRLNNVE F SLKKSFVDNNRVA E LIPQCDV I
cDOT1L      RTQMSV GVE LMD NLAEIA EKNKEFNERLLNH FGKKVYATR F -IHGSFTSPAVIR E IQTKATV I
hDOT1L      NCKHHY GVE KAD IPAKYA ETMDREFRKWMKW YGKK--HAEY TLERGDFLSEEWR E RIANTSV I
dDOT1L      PLKTCI GIE KAD TPARYA ERMDVIFRQYMGW EGKR--FCE Y KLIKGDFLVDEHR E NITSSTI V
              II                                     III
yDOT1       LVNN FLF DEDLNKKVEKILQTAKVGCK ITS LKSL-RSLTYQINFYNVE N IFNRLKVQRYDLKE
cDOT1L      LANN VRF DPELKLQLKEILMGCKDRTR IIS SEPLVPSRARQTNSRRAD D FVKISDESLLNLVD
hDOT1L      FVNN FAF GPEVDHQLKERFANMKEGGR IVS SKPFAP-LNFRINSRNLS D IGTIMRVVELSPLK
dDOT1L      FVNN FAF GPTVDHQLKERFADLRDGAR VVS SKSFCP-LNFRITDRNLS D IGTIMHVSEIPPLK yDOT1       DS VSWT HSGGEYYISTV MEDVDESLF SPAARGRRNRGTPVKYTR  582  (SEQ ID NO:5)
cDOT1L      NN VSWT SRKVPFYLTTI NRNKVSFF YCVRF                365  (SEQ ID NO:8)
hDOT1L      GS VSWT GKPVSYYLHTI DRTILENY FSSLKNPKLREEQEAARRR   344  (SEQ ID NO:6)
dDOT1L      GS VSWT CKPVSYYLHVI DRTILERY EQRLKTKGGNDHESVGTVR   350  (SEQ ID NO:7)
```

FIG. 2A

```
MGEKLELRLK  SPVGAEPAVY  PWPLPVYDKH  HDAAHEIIET    40
IRWVCEEIPD  LKLAMENYVL  IDYDTKSFES  MQRLCDKYNR    80
AIDSIHQLWK  GTTQPMKLNT  RPSTGLLRHI  LQQVYNHSVT   120
DPEKLNNYEP  FSPEVYGETS  FDLVAQMIDE  IKMTDDDLFV   160
DLGSGVGQVV  LQVAAATNCK  HHYGVEKADI  PAKYAETMDR   200
EFRKWMKWYG  KKHAEYTLER  GDFLSEEWRE  RIANTSVIFV   240
NNFAFGPEVD  HQLKERFANM  KEGGRIVSSK  PFAPLNFRIN   280
SRNLSDIGTI  MRVVELSPLK  GSVSWTGKPV  SYYLHTIDRT   320
ILENYFSSLK  NPKLREEQEA  ARRQQRESK   SNAATPTKGP   360
EGKVAGPADA  PMDSGAEEEK  AGAATVKKPS  PSKARKKKLN   400
KKGRKMAGRK  RGRPKKMNTA  NPERKPKKNQ  TALDALHAQT   440
VSQTAASSPQ  DAYRSPHSPF  YQLPPSVQRH  SPNPLLVAPT   480
PPALQKLLES  FKIQYLQFLA  YTKTPQYKAS  LQELLGQEKE   520
KNAQLLGAAQ  QLLSHCQAQK  EEIRRLFQQK  LDELGVKALT   560
YNDLIQAQKE  ISAHNQQLRE  QSEQLEQDNR  ALRGQSLQLL   600
KARCEELQLD  WATLSLEKLL  KEKQALKSQI  SEKQRHCLEL   640
QISIVELEKS  QRQQELLQLK  SCVPPDDALS  LHLRGKGALG   680
RELEPDASRL  HLELDCTKFS  LPHLSSMSPE  LSMNGQAAGY   720
ELCGVLSRPS  SKQNTPQYLA  SPLDQEVVPC  TPSHVGRPRL   760
EKLSGLAAPD  YTRLSPAKIV  LRRHLSQDHT  VPGRPAASEL   800
HSRAEHTKEN  GLPYQSPSVP  GSMKLSPQDP  RPLSPGALQL   840
AGEKSSEKGL  RERAYGSSGE  LITSLPISIP  LSTVQPNKLP   880
VSIPLASVVL  PSRAERARST  PSPVLQPRDP  SSTLEKQIGA   920
NAHGAGSRSL  ALAPAGFSYA  GSVAISGALA  GSPASLTPGA   960
EPATLDESSS  SGSLFATVGS  RSSTPQHPLL  LAQPRNSLPA  1000
SPAHQLSSSP  RLGGAAQGPL  PEASKGDLPS  DSGFSDPESE  1040
AKRRIVFTIT  TGAGSAKQSP  SSKHSPLTAS  ARGDCVPSHG  1080
QDSRRRGRRK  RASAGTPSLS  AGVSPKRRAL  PSVAGLFTQP  1120
SGSPLNLNSM  VSNINQPLEI  TAISSPETSL  KSSPVPYQDH  1160
DQPPVLKKER  PLSQTNGAHY  SPLTSDEEPG  SEDEPSSARI  1200
ERKIATISLE  SKSPPKTLEN  GGGLAGRKPA  PAGEPVNSSK  1240
WKSTFSPISD  IGLAKSADSP  LQASSALSQN  SLFTFRPALE  1280
EPSADAKLAA  HPRKGFPGSL  SGADGLSPGT  NPANGCTFGG  1320
GLAADLSLHS  FSDGASLPHK  GPEAAGLSSP  LSFPSQRGKE  1360
GSDANPFLSK  RQLDGLAGLK  GEGSRGKEAG  EGGLPLCGPT  1400
DKTPLLSGKA  AKARDREVDL  KNGHNLFISA  AAVPPGSLLS  1440
GPGLAPAASS  AGGAASSAQT  HRSFLGPFPP  GPQFALGPMS  1480
LQANLGSVAG  SSVLQSLFSS  VPAAAGLVHV  SSAATRLTNS  1520
HAMGSFSGVA  GGTVGGN (SEQ ID NO:2)                1537
```

FIG. 2B

```
CCCGCCTAGC  ATGGTGCGGC  GGCCGCGCGC  GCGGACATGG    40
GGGAGAAGCT  GGAGCTGAGA  CTGAAGTCGC  CCGTGGGGGC    80
TGAGCCCGCC  GTCTACCCGT  GGCCGCTGCC  GGTCTACGAT   120
AAACATCACG  ATGCTGCTCA  TGAAATCATC  GAGACCATCC   160
GATGGGTCTG  TGAAGAAATC  CCGGATCTCA  AGCTCGCTAT   200
GGAGAATTAC  GTTTTAATTG  ACTATGACAC  CAAAAGCTTC   240
GAGAGCATGC  AGAGGCTCTG  CGACAAGTAC  AACCGTGCCA   280
TCGACAGCAT  CCACCAGCTG  TGGAAGGGCA  CCACGCAGCC   320
CATGAAGCTG  AACACGCGGC  CGTCCACTGG  ACTCCTGCGC   360
CATATCCTGC  AGCAGGTCTA  CAACCACTCG  GTGACCGACC   400
CCGAGAAGCT  CAACAACTAC  GAGCCCTTCT  CCCCCGAGGT   440
GTACGGGGAG  ACCTCCTTCG  ACCTGGTGGC  CCAGATGATT   480
GATGAGATCA  AGATGACCGA  CGACGACCTG  TTTGTGGACT   520
TGGGGAGCGG  TGTGGGCCAG  GTCGTGCTCC  AGGTTGCTGC   560
TGCCACCAAC  TGCAAACATC  ACTATGGCGT  CGAGAAAGCA   600
GACATCCCGG  CCAAGTATGC  GGAGACCATG  GACCGCGAGT   640
TCAGGAAGTG  GATGAAATGG  TATGGAAAAA  AGCATGCAGA   680
ATACACATTG  GAGAGAGGCG  ATTTCCTCTC  AGAAGAGTGG   720
AGGGAGCGAA  TCGCCAACAC  GAGTGTTATA  TTTGTGAATA   760
ATTTTGCCTT  TGGTCCTGAG  GTGGATCACC  AGCTGAAGGA   800
GCGGTTTGCA  AACATGAAGG  AAGGTGGCAG  AATCGTGTCC   840
TCGAAACCCT  TTGCACCTCT  GAACTTCAGA  ATAAACAGTA   880
GAAACTTGAG  TGACATCGGC  ACCATCATGC  GCGTGGTGGA   920
GCTCTCGCCC  TGAAGGGCT  CGGTGTCGTG  GACGGGGAAG   960
CCAGTCTCCT  ACTACCTGCA  CACTATCGAC  CGCACCATAC  1000
TTGAAAACTA  TTTTTCTAGT  CTGAAAAACC  AAAACTCAG   1040
GGAGGAACAG  GAGGCAGCCC  GGCGCCGCCA  GCAGCGCGAG  1080
AGCAAGAGCA  ACGCGGCCAC  GCCCACTAAG  GGCCCAGAGG  1120
GCAAGGTGGC  CGGCCCCGCC  GACGCCCCCA  TGGACTCTGG  1160
TGCTGAGGAA  GAGAAGGCGG  GAGCAGCCAC  CGTGAAGAAG  1200
CCGTCTCCCT  CCAAAGCCCG  CAAGAAGAAG  CTAAACAAGA  1240
AGGGGAGGAA  GATGGCTGGC  CGCAAGCGCG  GCGCCCCAA   1280
GAAGATGAAC  ACTGCGAACC  CGAGCGGAA   GCCCAAGAAG  1320
AACCAAACTG  CACTGGATGC  CCTGCACGCT  CAGACCGTGT  1360
CTCAGACGGC  GGCCTCCTCA  CCCCAGGATG  CCTACAGATC  1400
CCCTCACAGC  CCGTTCTACC  AGCTACCTCC  GAGCGTGCAG  1440
CGGCACTCCC  CCAACCCGCT  GCTGGTGGCG  CCCACCCCGC  1480
CCGCGCTGCA  GAAGCTTCTA  GAGTCCTTCA  AGATCCAGTA  1520
CCTGCAGTTC  CTGGCATACA  CAAAGACCCC  CCAGTACAAG  1560
GCCAGCCTGC  AGGAGCTGCT  GGGCCAGGAG  AAGGAGAAGA  1600
ACGCCAGCT   CCTGGGTGCG  GCTCAGCAGC  TCCTCAGCCA  1640
CTGCCAGGCC  CAGAAGGAGG  AGATCAGGAG  GCTGTTTCAG  1680
```

*FIG. 2C*

| | | | | |
|---|---|---|---|---|
| CAAAAATTGG | ATGAGCTGGG | TGTGAAGGCG | CTGACCTACA | 1720 |
| ACGACCTGAT | TCAAGCGCAG | AAGGAGATCT | CCGCCCATAA | 1760 |
| CCAGCAGCTG | CGGGAGCAGT | CGGAGCAGCT | GGAGCAGGAC | 1800 |
| AACCGCGCGC | TCCGCGGCCA | GAGCTTGCAG | CTGCTCAAGG | 1840 |
| CTCGCTGCGA | GGAGCTGCAG | CTGGACTGGG | CCACGCTGTC | 1880 |
| GCTGGAGAAG | CTGTTGAAGG | AGAAGCAGGC | CCTGAAGAGC | 1920 |
| CAGATCTCGG | AGAAGCAGAG | GCACTGCCTG | GAGCTGCAGA | 1960 |
| TCAGCATTGT | GGAGCTAGAG | AAGAGCCAGC | GGCAGCAGGA | 2000 |
| GCTCCTGCAG | CTCAAGTCCT | GTGTGCCGCC | TGACGACGCC | 2040 |
| CTGTCCCTGC | ACCTGCGTGG | GAAGGGCGCC | CTGGGCCGCG | 2080 |
| AGCTGGAGCC | TGACGCCAGC | CGGCTGCACC | TGGAGCTGGA | 2120 |
| CTGCACCAAG | TTCTCGCTGC | CTCACTTGAG | CAGCATGAGC | 2160 |
| CCGGAGCTCT | CCATGAACGG | CCAGGCTGCT | GGCTATGAGC | 2200 |
| TCTGCGGTGT | GCTGAGCCGG | CCTTCGTCGA | AGCAGAACAC | 2240 |
| GCCCCAGTAC | CTGGCCTCAC | CCTGGACCA | GGAGGTGGTG | 2280 |
| CCCTGTACCC | CTAGCCACGT | CGGCCGGCCG | CGCCTGGAGA | 2320 |
| AGCTGTCTGG | CCTAGCCGCA | CCCGACTACA | CTAGGCTGTC | 2360 |
| CCCGGCCAAG | ATTGTGCTGA | GGCGGCACCT | GAGCCAGGAC | 2400 |
| CACACGGTGC | CCGGCAGGCC | GGCTGCCAGT | GAGCTGCATT | 2440 |
| CGAGAGCTGA | GCACACCAAG | GAGAACGGCC | TTCCCTACCA | 2480 |
| GAGCCCCAGC | GTGCCTGGCA | GCATGAAGCT | GAGCCCTCAG | 2520 |
| GACCCGCGGC | CCCTGTCCCC | TGGGGCCTTG | CAGCTTGCTG | 2560 |
| GAGAGAAGAG | CAGTGAGAAG | GGCCTGAGAG | AGCGCGCCTA | 2600 |
| CGGCAGCAGC | GGGGAGCTCA | TCACCAGCCT | GCCCATCAGC | 2640 |
| ATCCCGCTCA | GCACCGTGCA | GCCCAACAAG | CTCCCGGTCA | 2680 |
| GCATTCCCCT | GGCCAGCGTG | GTGCTGCCCA | GCCGCGCCGA | 2720 |
| GAGGGCGAGG | AGCACCCCCA | GTCCCGTGCT | GCAGCCCCGT | 2760 |
| GACCCTCGT | CCACACTTGA | AAAGCAGATT | GGTGCTAATG | 2800 |
| CCCACGGTGC | TGGGAGCAGA | AGCCTTGCCC | TGGCCCCCGC | 2840 |
| AGGCTTCTCC | TACGCTGGCT | CGGTGGCCAT | CAGCGGGGCC | 2880 |
| TTGGCGGGCA | GCCCGGCCTC | TCTCACACCT | GGAGCCGAGC | 2920 |
| CGGCCACCTT | GGATGAGTCC | TCCAGCTCTG | GGAGCCTTTT | 2960 |
| TGCCACCGTG | GGGTCCCGCA | GCTCCACGCC | ACAGCACCCC | 3000 |
| CTGCTGCTGG | CACAGCCCCG | GAACTCGCTT | CCTGCCTCTC | 3040 |
| CCGCCCACCA | GCTCTCCTCC | AGTCCCCGGC | TTGGTGGGGC | 3080 |
| CGCCCAGGGC | CCGTTGCCCG | AGGCCAGCAA | GGGAGACCTG | 3120 |
| CCCTCCGATT | CCGGCTTCTC | AGATCCTGAG | AGTGAAGCCA | 3160 |
| AGAGGAGGAT | TGTGTTCACC | ATCACCACTG | GTGCGGGCAG | 3200 |
| TGCCAAGCAG | TCGCCCTCCA | GCAAGCACAG | CCCCCTGACC | 3240 |
| GCCAGCGCCC | GTGGGGACTG | TGTGCCGAGC | CACGGGCAGG | 3280 |
| ACAGTCGCAG | GCGCGGCCGG | CGGAAGCGAG | CATCTGCGGG | 3320 |

FIG. 2D

```
GACGCCCAGC TTGAGCGCAG GCGTGTCCCC CAAGCGCCGA    3360
GCCCTGCCGT CCGTCGCTGG CCTTTTCACA CAGCCTTCGG    3400
GGTCTCCCCT CAACCTCAAC TCCATGGTCA GTAACATCAA    3440
CCAGCCCCTG GAGATTACAG CCATCTCGTC CCCGGAGACC    3480
TCCCTGAAGA GCTCCCTGT GCCCTACCAG GACCACGACC     3520
AGCCCCCGT GCTCAAGAAG GAGCGGCCTC TGAGCCAGAC     3560
CAATGGGGCA CACTACTCCC CACTCACCTC AGACGAGGAG    3600
CCAGGCTCTG AGGACGAGCC CAGCAGTGCT CGAATTGAGA    3640
GAAAAATTGC AACAATCTCC TTAGAAAGCA AATCTCCCCC    3680
GAAAACCTTG GAAATGGTG GTGGCTTGGC GGGAAGGAAG     3720
CCCGCGCCCG CCGGCGAGCC AGTCAATAGC AGCAAGTGGA    3760
AGTCCACCTT CTCGCCCATC TCCGACATCG GCCTGGCCAA    3800
GTCGGCGGAC AGCCCGCTGC AGGCCAGCTC CGCCCTCAGC    3840
CAGAACTCCC TGTTCACGTT CCGGCCCGCC CTGGAGGAGC    3880
CCTCTGCCGA TGCCAAGCTG GCCGCTCACC CCAGGAAAGG    3920
CTTTCCCGGC TCCCTGTCGG GGCTGACGG ACTCAGCCCG     3960
GGCACCAACC CTGCCAACGG CTGCACCTTC GGCGGGGCC     4000
TGGCCGCGGA CCTGAGTTTA CACAGCTTCA GTGATGGTGC    4040
TTCTCTTCCC CACAAGGGCC CCGAGGCGGC CGGCCTGAGC    4080
TCCCCGCTGA GCTTCCCCTC GCAGCGCGGC AAGGAGGGCT    4120
CGGACGCCAA CCCTTTCCTG AGCAAGAGGC AGCTGGACGG    4160
CCTGGCTGGG CTGAAGGGCG AGGGCAGCCG CGGCAAGGAG    4200
GCAGGGGAGG GCGGCCTACC GCTGTGCGGG CCCACGGACA    4240
AGACCCCACT GCTGAGCGGC AAGGCCGCCA AGGCCCGGGA    4280
CCGCGAGGTC GACCTCAAGA ATGGCCACAA CCTCTTCATC    4320
TCTGCGGCGG CCGTGCCTCC CGGAAGCCTC CTCAGCGGCC    4360
CCGGCCTGGC CCCGGCGGCG TCCTCCGCAG GCGGCGCGGC    4400
GTCCTCCGCC CAGACGCACC GGTCCTTCCT GGGCCCCTTC    4440
CCGCCGGGAC CGCAGTTCGC GCTCGGCCCC ATGTCCCTGC    4480
AGGCCAACCT CGGCTCCGTG GCCGGCTCCT CCGTGCTGCA    4520
GTCGCTGTTC AGCTCTGTGC CGGCCGCCGC AGGCCTGGTG    4560
CACGTGTCGT CCGCTGCCAC CAGACTGACC AACTCGCACG    4600
CCATGGGCAG CTTTTCCGGG GTGGCAGGCG GCACAGTTGG    4640
AGGTAACTAG GATTTCTACC TCAACCGCGA GACCTATGCA    4680
AGGACGGTGT GGACCAACTC GCGCCCGCGG CATGGTGCCC    4720
GCCGGCCTGC CGGGCTCCCA CCCCTGGACG GCAGAGGCAA    4760
GGACGGACGG GAGCTCCACT GTGAATCGGC GGCACGCGCC    4800
GCAGGAGGCT GGGACTGGTC CAGTTTGTAC TGTCGATAGT    4840
TTTAGATAAA GTATTTATCA TTTTTTAAAA AGTAAAAAAA    4880
AAAAAAAAA (SEQ ID NO:1)                       4889
```

FIG. 2E

```
                    +                  +
hDOT1   361  EGKVAGPADAPMDS-GAEEEKAGAAT  385
yDOT1    87  KGKDNGLVPLVEKVIPPIHKKTNNRN  112

+            +          +
hDOT1   VKKPSPSKARKKKLNKKGRKMAGRK-RGRPKK  416  (SEQ ID NO:9)
yDOT1   TRKKSSTTTKKDVKKPKAAKVKGKNGRTNHKH  144  (SEQ ID NO:10)
```

```
PKI-NES        aa 482 NELALKLAGLDINKT 496 (SEQ ID NO:11)
hDOT1L-NES1         PALQKLLESFKIQYL     (SEQ ID NO:12)
hDOT1L-NES3    aa 636 HCLELQISIVELEKS 650 (SEQ ID NO:13)
hDOT1L-NES1M        PALQKLLESAKAQYL     (SEQ ID NO:14)
```

| | GAL BD-FUSION | GAL AD-FUSION | GROWTH ON SD-W | GROWTH ON SD-L | GROWTH ON SD-W/-L/-H/-Ade/+ X-α-GAL |
|---|---|---|---|---|---|
| 1 | NONE | NONE | - | - | - |
| 2 | hDOT1L | NONE | + | - | - |
| 3 | NONE | AF10 | - | + | - |
| 4 | hDOT1L | AF10 | + | + | + |

IP:αFLAG®, IB:αHA

DOT1 HISTONE METHYLTRANSFERASES AS A TARGET FOR IDENTIFYING THERAPEUTIC AGENTS FOR LEUKEMIA

RELATED APPLICATION INFORMATION

This application claims the benefit of priority from U.S. provisional patent application Ser. No. 60/478,497, filed 13 Jun. 2003, which is incorporated herein by reference in its entirety.

STATEMENT OF FEDERAL SUPPORT

This invention was made with federal support under Grant Nos. GM63076 and GM68804 awarded by the National Institutes of Health/National Cancer Institute. The United States government has certain rights in the invention.

FIELD OF THE INVENTION

The present invention relates to novel histone methyltransferases as well as nucleic acids encoding the same; also disclosed are methods for identifying compounds that modulate the activity of the histone methyltransferase, methods of identifying compounds that inhibit binding of a polypeptide to the histone methyltransferase, methods of identifying candidate compounds for the treatment of leukemia, and diagnostic methods based on histone methylation.

BACKGROUND OF THE INVENTION

Higher-order chromatin structures are of profound importance in gene regulation and epigenetic inheritance (Wu and Grunstein (2000) *Trends Biochem. Sci.* 25:619-623). Post-translational modifications of core histones critically influence the establishment and maintenance of higher-order chromatin structures. The unstructured tails of certain core histones are extensively modified by acetylation, methylation, phosphorylation, ribosylation and ubiquitination. A "histone code" hypothesis, linking histone modifications to chromatin structures, has been the focus of intensive recent studies (Strahl and Allis (2000) *Mol. Cell. Biol.* 22:1298-1306; Turner (2000) *Bioessays* 22:836-845). Histone methylation has emerged as a major form of histone modification. (Strahl and Allis (2000) *Mol. Cell. Biol.* 22: 1298-1306; Zhang and Reinberg (2001) *Genes Dev.* 15:2343-2360). In particular, a large family of SET domain-containing histone methyltransferases (HMTases) has been identified (Lachner and Jenuwein (2002) *Curr. Opin. Cell Biol.* 14:286-298). SET domain proteins have been shown to methylate various N-terminal lysine residues of histone H3 and H4. Histone lysine methylation has been associated with diverse biological processes ranging from transcriptional regulation to the faithful transmission of chromosomes during the cell division (Grewal and Elgin (2002) *Curr. Opin. Genet. Dev.* 12:178-187).

Further, lysine methylation catalyzed by SET domain containing proteins has been linked to cancer (Schneider, et al. (2002) *Trends Biochem. Sci.* 27:396-402). For example, the H3-K4 methyltransferase MLL is frequently translocated in leukemia (Ayton and Cleary (2001) *Oncogene* 20:5695-5707; Milne, et al. (2002) *Mol. Cell* 10:1107-1117; Nakamura, et al. (2002) *Mol. Cell* 10:1119-1128) and the H3-K27 methyltransferase EZH2 is overexpressed in a number of tumors and its expression level correlates with the invasiveness of these tumors (Bracken, et al. (2003) *EMBO J.* 22:5323-5335; Kleer, et al. (2003) *Proc. Natl. Acad. Sci. USA* 100:11606-11611; Varambally, et al. (2002) *Nature* 419:624-9).

Chromosomal translocation is one of the major causes of human cancer, particularly in acute leukemias. The most common chromosome rearrangement found in leukemia patients involves the mixed lineage leukemia gene MLL (also called ALL or HRX) located at 11q23 (Ayton and Cleary (2001) *Oncogene* 20:5695-5707). MLL is the human homologue of *Drosophila* Trithorax (Trx), a protein involved in maintaining the "on state" of the homeotic box (Hox) gene expression during embryonic development. MLL contains a number of functional motifs including the N-terminal AT hook DNA binding motif and the C-terminal SET domain required for its H3-lysine 4 methyltransferase activity (Milne, et al. (2002) *Mol. Cell* 10:1107-1117; Nakamura, et al. (2002) *Mol. Cell* 10:1119-1128). As a result of chromosome translocation, MLL N-termini become fused in-frame with one of more than 30 partner proteins (Ayton and Cleary (2001) *Oncogene* 20:5695-5707). Regardless of whether the fusion partner is normally localized to the nucleus or cytoplasm, the chimeras are always nuclear (Dimartino and Cleary (1999) *Br. J. Haematol.* 106:614-626). Given that the DNA binding domain of MLL is still retained in the fusion proteins, the MLL target genes will be differentially regulated as a result of loss of the MLL SET domain and gain of fusion partner function in the chimeras. HOXA9 has emerged as one of the most relevant MLL target genes in human acute myeloid leukemia (AML) as it is always up-regulated in AML (Golub, et al. (1999) *Science* 286:531-537). Indeed, the leukemogenic potential of Hoxa9 was directly demonstrated by the development of AML in mice receiving transplantation of bone marrow cells overexpressing Hoxa9 (Kroon, et al. (1998) *EMBO J.* 17:3714-3725). Both Hoxa7 and Hoxa9 have been shown to be required for MLL fusion proteins to transform myeloid progenitor cells (Ayton and Cleary (2003) *Genes Dev.* 17:2298-2307). However, the mechanism by which different MLL fusion proteins up-regulate HOXA9 and how higher levels of HOXA9 leads to leukemia remains to be elucidated.

Dot1 is an evolutionarily conserved protein that was originally identified in *S. cerevisiae* as a disruptor of telomeric silencing (Singer, et al. (1998) *Genetics* 150:613-632). It also functions at the pachytene checkpoint during the meiotic cell cycle (San-Segundo and Roeder (2000) *Mol. Biol. Cell.* 11:3601-3615). Sequence analysis of yeast Dot1 revealed that it possesses certain characteristic SAM binding motifs, similar to the ones in protein arginine methyltransferases (Dlakic (2001) *Trends Biochem. Sci.* 26:405-407).

SUMMARY OF THE INVENTION

The present invention is based, in part, on the first identification of a post-translational modification within the globular domain of the histone. In particular, the inventors have observed methylation of lysine 79 of histone H3 ("H3-K79") and have identified a novel class of histone methyltransferase (HMTase) designated "DOT1" that methylates H3-K79 in vivo. DOT1L (see, e.g., SEQ ID NO:2) is a member of the DOT1 family. Similar to other HMTases, the DOT1 polypeptides contain a S-adenosylmethionine (SAM) binding site and use SAM as a methyl donor. However, unlike other reported HMTases, the DOT1 polypeptides do not contain a SET domain.

Accordingly, as a first aspect, the present invention provides an isolated nucleic acid comprising a nucleotide sequence encoding a DOT1L polypeptide, the nucleotide sequence selected from the group consisting of: (a) a nucleotide sequence comprising the nucleotide sequence of SEQ ID NO:1; (b) a nucleotide sequence that hybridizes to the complete complement of a nucleotide sequence comprising the nucleotide sequence of SEQ ID NO:1 under stringent conditions, wherein the nucleotide sequence encodes a polypeptide having histone H3 lysine 79 (H3-K79) methyltransferase activity; (c) a nucleotide sequence having at least 95% nucleotide sequence similarity with the nucleotide sequence of SEQ ID NO:1, wherein the nucleotide sequence encodes a polypeptide having H3-K79 methyltransferase activity; (d) a nucleotide sequence that differs from the nucleotide sequence of (a) above due to the degeneracy of the genetic code; (f) a nucleotide sequence comprising a functional fragment of SEQ ID NO:1, wherein the functional fragment comprises at least the coding region of the histone methyltransferase catalytic domain of SEQ ID NO:1 or a nucleotide sequence that hybridizes to the complete complement of the coding region of the histone methyltransferase catalytic domain of SEQ ID NO:1 under stringent conditions, and wherein the functional fragment encodes a polypeptide having H3-K79 methyltransferase activity; (g) a nucleotide sequence comprising a functional fragment of SEQ ID NO:1, wherein the functional fragment comprises at least the coding region of the histone methyltransferase catalytic domain of SEQ ID NO:1 or a nucleotide sequence having at least 95% nucleotide sequence similarity thereto, and wherein the functional fragment encodes a polypeptide having H3-K79 methyltransferase activity; and (h) a nucleotide sequence comprising a functional fragment of SEQ ID NO:1, wherein the functional fragment comprises at least the coding region of the histone methyltransferase catalytic domain of SEQ ID NO:1 or a nucleotide sequence that differs therefrom due to the degeneracy of the genetic code, and wherein the functional fragment encodes a polypeptide having H3-K79 methyltransferase activity.

Also provided are vectors comprising the nucleic acids of the invention, as well as cells comprising the inventive nucleic acids and vectors.

As a further embodiment, the invention provides an isolated DOT1L polypeptide comprising an amino acid sequence selected from the group consisting of: (a) the amino acid sequence of SEQ ID NO:2; (b) an amino acid sequence having at least 95% amino acid sequence similarity with the amino acid sequence of SEQ ID NO:2, wherein the DOT1L polypeptide has histone H3 lysine 79 (H3-K79) methyltransferase activity; and (c) a functional fragment of at least 400 amino acids of the amino acid sequence of (a) or (b) above, wherein the functional fragment comprises a DOT1L histone methyltransferase catalytic domain and has H3-K79 methyltransferase activity.

Also provided are fusion proteins comprising the inventive DOT1L polypeptide. Further provided are cells comprising the fusion proteins of the invention.

As a further aspect, the invention comprises a method of identifying a compound that modulates DOT1L histone H3 lysine 79 (H3-K79) methyltransferase activity, the method comprising contacting a DOT1L polypeptide of the invention with a nucleosome substrate comprising H3 in the presence of a test compound; detecting the level of H3-K79 methylation of the nucleosome substrate under conditions sufficient to provide H3-K79 methylation, wherein an elevation or reduction in H3-K79 methylation in the presence of the test compound as compared with the level of histone H3-K79 methylation in the absence of the test compound indicates that the test compound modulates DOT1L H3-K79 methyltransferase activity.

As still a further aspect, the invention provides a method of identifying a candidate compound for the prevention and/or treatment of leukemia, the method comprising: contacting a DOT1L polypeptide of the invention with a nucleosome substrate comprising histone H3 in the presence of a test compound; detecting the level of histone H3 lysine 79 (H3-K79) methylation of the nucleosome substrate under conditions sufficient to provide H3-K79 methylation, wherein a reduction in H3-K79 methylation in the presence of the test compound as compared with the level of H3-K79 methylation in the absence of the test compound indicates that the test compound is a candidate compound for the prevention and/or treatment of leukemia.

As still a further aspect, the invention provides a method of identifying a compound that inhibits binding of DOT1L polypeptide to a second polypeptide, comprising: contacting a DOT1L polypeptide according to the invention with a second polypeptide in the presence of a test compound; detecting the level of binding between DOT1L polypeptide and the second polypeptide under conditions sufficient for binding of DOT1L polypeptide to the second polypeptide, wherein a reduction in binding between DOT1L polypeptide and the second polypeptide in the presence of the test compound as compared with the level of binding in the absence of the test compound indicates that the test compound inhibits binding of DOT1L polypeptide to the second polypeptide.

As yet another aspect, the invention provides a method of identifying a candidate compound for the prevention and/or treatment of leukemia, comprising: contacting a DOT1L polypeptide of the invention with AF10 or an MLL fusion protein in the presence of a test compound; detecting the level of binding between the DOT1L polypeptide and AF10 or MLL fusion protein under conditions sufficient for binding of DOT1L polypeptide to AF10 or MLL fusion protein, wherein a reduction in binding between DOT1L polypeptide and AF10 or the MLL fusion protein in the presence of the test compound as compared with the level of binding in the absence of the test compound indicates that the test compound is a candidate compound for the prevention and/or treatment of leukemia.

As a further aspect, the invention provides a method of diagnosing whether a subject has or is at risk for developing leukemia and/or determining the prognosis for the course of the disease, comprising: obtaining a biological sample comprising nucleosomes from a subject; detecting the level of histone H3 lysine 79 (H3-K79) methylation associated with the HoxA9 gene; wherein an elevation in HoxA9-associated H3-K79 methylation in the biological sample as compared with the level of HoxA9-associated H3-K79 methylation in a non-leukemic biological sample is diagnostic that the subject has or is at risk of developing leukemia and/or is prognostic of the course of the disease in the subject.

These and other aspects of the invention are set forth in more detail in the description of the invention below.

Equivalent amounts of histones, as evidenced by COOMASSIE® staining, from the indicated organisms were analyzed by western blot analysis using the H3-mK79-specific antibody.

FIGS. 2A-2E show the identification of a human DOT1-like protein. (A) Alignment of the amino acid sequences of the DOT1 family proteins. Only the most conserved regions are shown. Sequences used in the alignment include yeast DOT1 (NP_010728; SEQ ID NO:5), and its homologs from human (AF509504; SEQ ID NO:6), Drosophila (AAF54122; SEQ ID NO:7), and C. elegans (NP_510056; SEQ ID NO:8). Four additional putative C. elegans proteins in GENBANK (NP_509981, NP_490970, NP_509997, NP_508351) also show homology to DOT1. Sequences predicted to be involved in SAM binding (Dlakic (2001) Trends Biochem. Sci. 26:405-407; incorporated by reference herein in its entirety for teachings of SAM binding domains in DOT1) are indicated. Numbers represent the amino acid number of respective proteins. Gaps are indicated by "–". Amino acids that are identical or have similar properties are boxed. (B) Amino acid sequence of human DOT1L (SEQ ID NO:2). Predicted SAM binding motifs are underlined. Mutation of the boxed amino acids abolished the HMTase activity of hDOT1L. (C-E) Nucleic acid sequence encoding human DOT1L (SEQ ID NO:1).

Figure 3A:
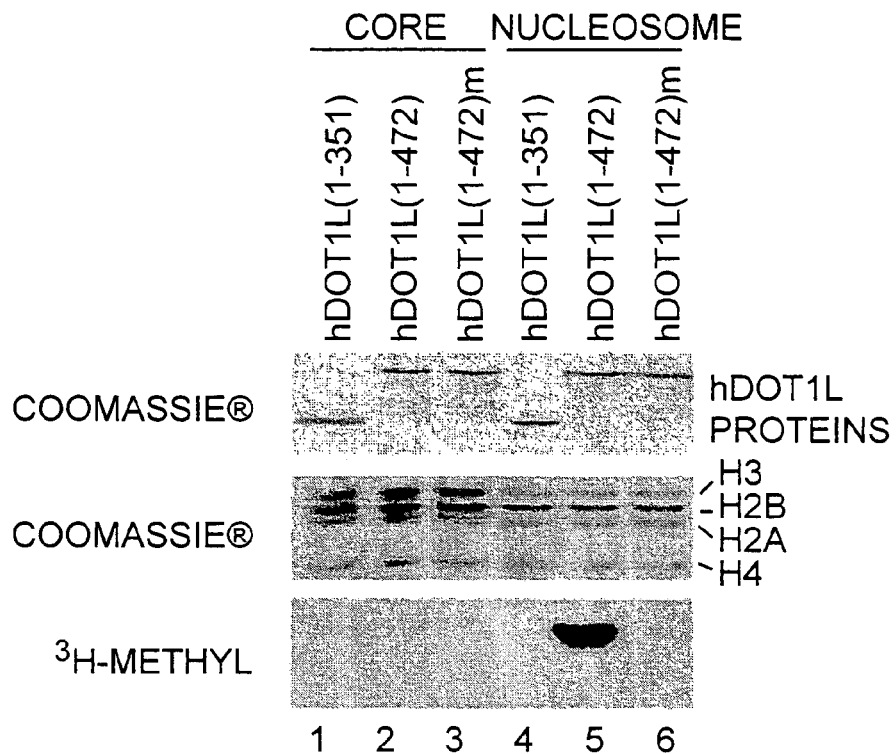
Figure 3B:
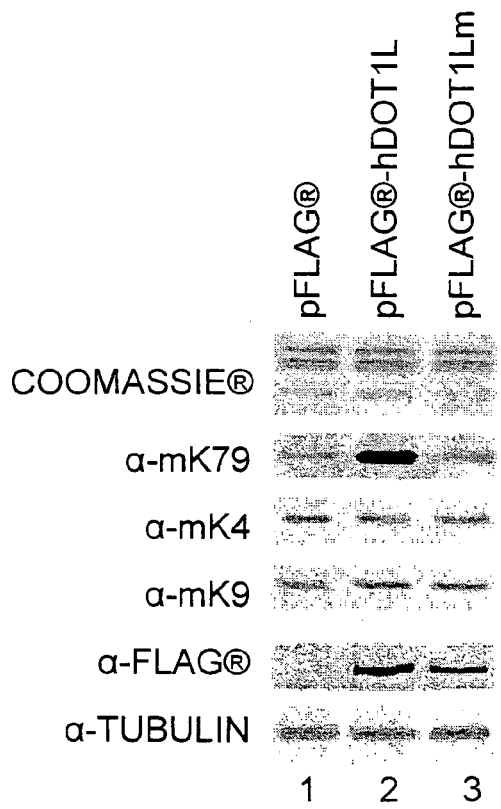

FIGS. 3A and 3B demonstrate that hDOT1L is a nucleosomal H3-K79-specific HMTase. (A) Recombinant hDOT1L is a nucleosomal H3-specific HMTase in vitro. About 0.2 μg of different versions of recombinant hDOT1L protein were incubated with 10 μg of core histones or equivalent amounts of nucleosomes using standard methods (Wang, et al. (2001) Mol. Cell 8:1207-1217). The reaction mixtures were resolved in SDS-PAGE followed by COOMASSIE® staining and fluorogram analysis. Recombinant hDOT1L proteins shown in the upper panel are 15-fold of what were used in the HMTase assay. (B) hDOT1L methylates H3-K79 in vivo. Empty vector, as well as vectors that encode FLAG®-tagged wild-type or mutant (m) hDOT1L were transfected into 293T cells using the QIAGEN® EFFECTENE™ Transfection Reagent. Two days after transfection, cells were collected for the preparation of total cell lysates and histones. Expression of wild-type and mutant hDOT1L was verified by western blot analysis using anti-FLAG® antibody. Equal loading of lysates was confirmed by probing for tubulin. Equal loading of histones was verified by COOMASSIE® staining.

FIGS. 4A-4E show that the level of H3-K79 methylation is cell cycle regulated. (A) Cells released from double thymidine block were analyzed by flow cytometry. The numbers of cells (arbitrary units) were plotted against DNA content. (B) Cell extracts and histones derived from samples analyzed in (A) were analyzed by western blot analysis. SLBP and cyclin A were used as cell cycle markers, tubulin was used as loading control. Equal loading of histones were revealed by COOMASSIE® staining. The level of H3-K79 methylation was analyzed by probing with the mK79-specific antibodies. The cell cycle stage of each sample is indicated on top of the panel. 'asy' represents synchronized cell extracts. (C, D) Identical to (A, B) except that the cells were arrested at M-phase before release. (E) mK79 level in relation to cell DNA content. Cells were labeled with FITC-conjugated goat anti-rabbit secondary antibody in the absence (left panel) or presence of primary antibody (middle and right panels) as indicated. DNA in each cell was labeled with propidium iodide (PI). Each spot represents an individual cell. The numbers represent an arbitrary FITC unit. Unlabeled cells were analyzed by flow cytometry (left panel insert) to serve as standard for DNA content. The intensity of FITC signal (measurement of Mi-2 or mK79) is plotted against PI signal (measurement of DNA content that correlates with cell cycle stages). Arrow heads and arrows represent early S-phase and late S phase, respectively.

Figure 5:
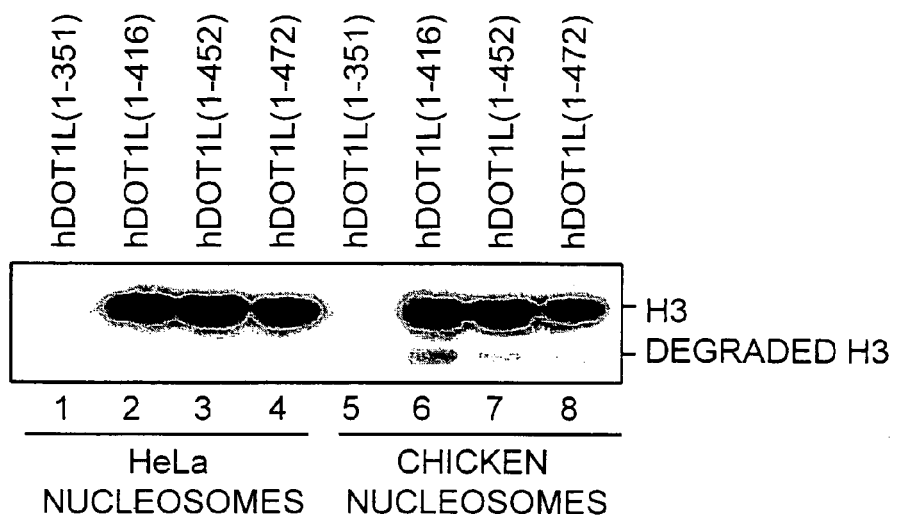

FIG. 5 shows that hDOT1L(1-416) is an active histone methyltransferase. Purified HeLa and chicken nucleosomes were used as substrates in the assay and proteins were analyzed by autoradiography.

FIGS. 6A-6D show HMTase activity and mono-nucleosome binding of hDOT1L derivatives. (A) The positively charged region (amino acids 390-407) is important for the HMTase activity of hDOT1L. Equal amount of hDOT1L deletion mutants (upper panel), indicated on top of the panel, were analyzed for HMTase activity (middle panel) and the quantitation is presented in the bottom panel. (B) The positively charged region required for HMTase activity is also required for mono-nucleosome binding. Mono-nucleosome binding of the hDOT1L deletions mutants was analyzed by gel mobility shift assays at three different protein concentrations (μM). (C) Amino acid sequence (amino acids 361-416; SEQ ID NO:9) of the C-terminal of hDOT1L(1-416) encompassing the charged region required for the HMTase activity. A stretch of similar amino acids located at the N-terminal of yeast Dot1 is also shown (SEQ ID NO:10). Identical amino acids between the yeast and human proteins are single underlined, and similar amino acids are double underlined. (D) The HMTase activities of hDOT1L(1-416) and Δ(376-390) in the absence and presence of increasing concentrations (μM) of a positively charged competitor peptide were analyzed by autoradiograph (top panel) and the quantitation is shown at the bottom panel.

Figure 7A:
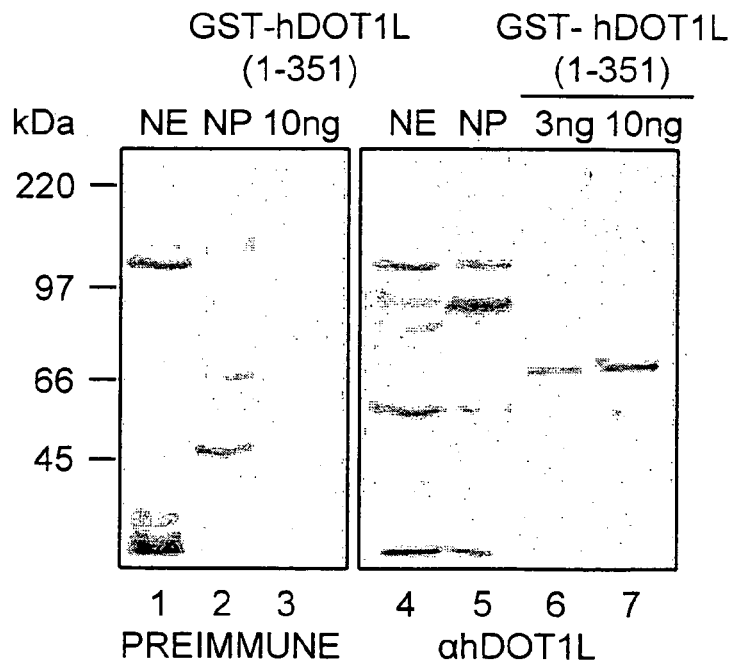
Figure 7B:
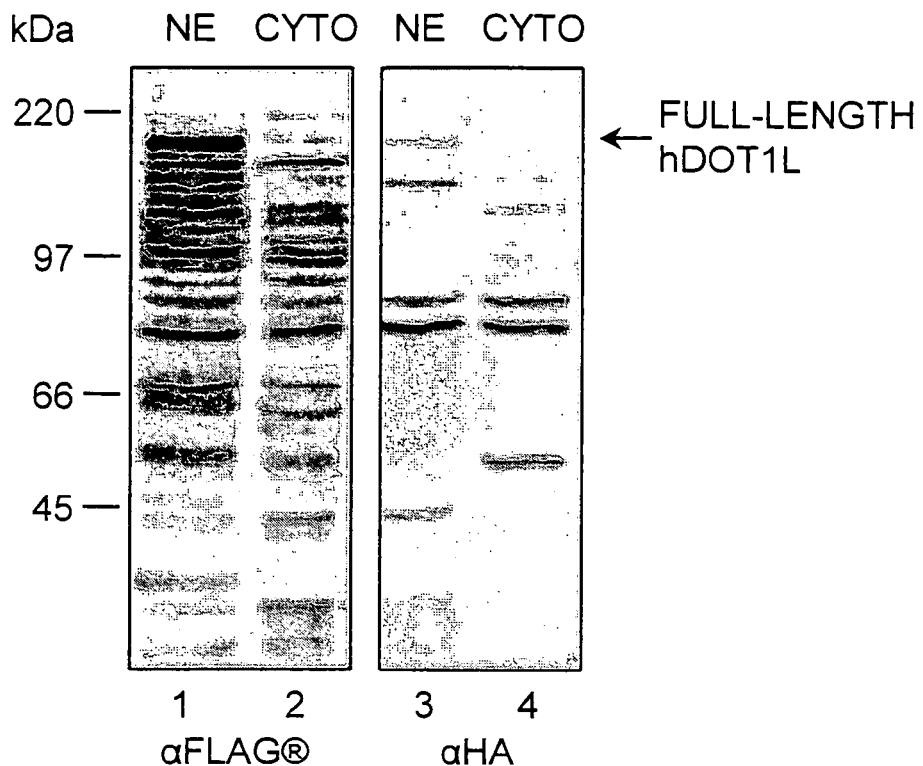
Figure 7C:
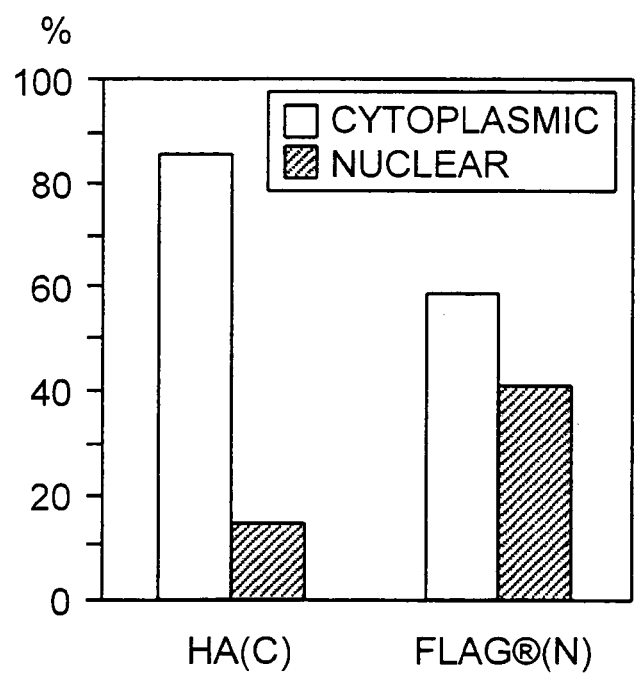

FIGS. 7A-7C show that hDOT1L is degraded extensively in cells. (A) Recombinant hDOT1L(1-351) digested by thrombin from GST-hDOT1L(1-352) was used to generate a rabbit polyclonal antibody. The antibody was affinity purified by incubating the serum with the antigen. Protein (100 μg) derived from HeLa nuclear extracts (NE) or nuclear pellet (NP), or recombinant GST-hDOT1L(1-351) were subjected to SDS-PAGE and blotted with either preimmune serum or affinity-purified hDOT1L antibody. (B) Full-length hDOT1L exists only in the nucleus. N-terminal FLAG®-tagged or C-terminal HA-tagged hDOT1L was transfected into 293T cells. Proteins (100 μg) derived from nuclear or cytoplasm fractions of transfected cells were subjected to western blot analysis using antibodies against FLAG® or HA. (C) hDOT1L tagged with an N-terminal FLAG® and a C-terminal HA was transfected into U2OS cells. Localization of hDOT1L was viewed by immunofluorescent staining using a monoclonal antibody against FLAG® and a polyclonal antibody against HA. Transfected cells with nuclear localization or cytoplasmic localization were counted and presented as percentage of total transfected cells.

Figure 8A:
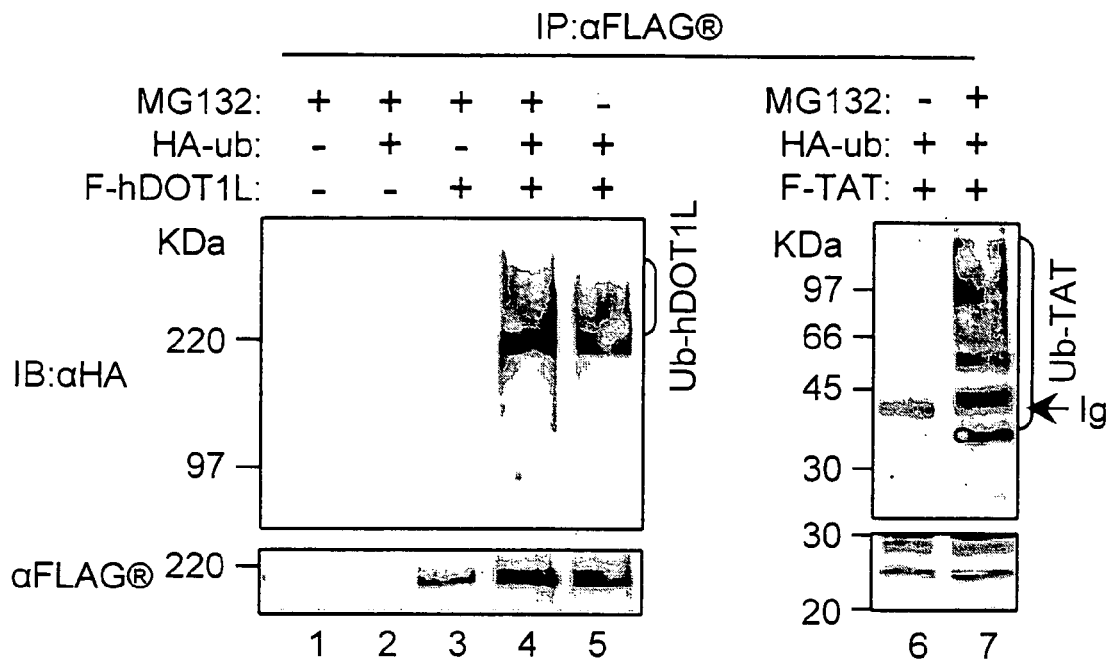
Figure 8B:
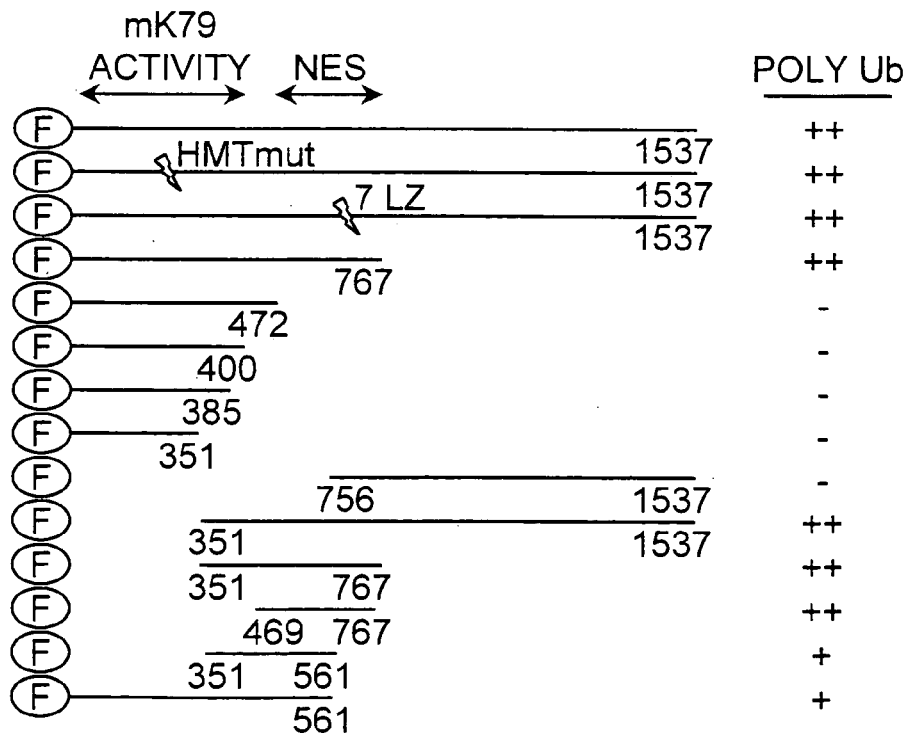
Figure 8C:
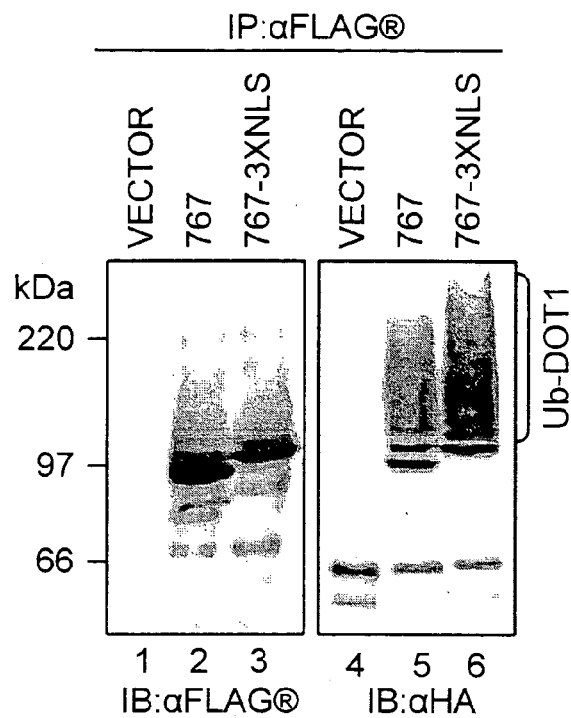

FIGS. 8A-8C show that hDOT1L is subjected to ubiquitination in vivo. (A) hDOT1L is subjected to ubiquitination but its degradation is not through the 26S proteasome pathway. FLAG®-tagged hDOT1L and Tat were co-expressed with HA-ubiquitin in the presence or absence of proteasome inhibitor MG132. Protein extracts derived from the transfected cells were immunoprecipitated with anti-FLAG® antibody and blotted with antibody against FLAG®. (B) hDOT1L ubiquitination occurs in the region between amino acid 469-756. Diagram of the hDOT1L constructs tested in the ubiquitination assays described in A. Results of the assays are summarized to the right of the panel. "++" represents full level of polyubiquitination; "+" represents lower level of polyubiquitination; "–" represents mono or no ubiquitination. (C) hDOT1L can be ubiquitinated equally well in both nucleus and cytoplasm. Western blot of the ubiquitination assays of the two hDOT1L(1-767) constructs indicated.

Lanes 5 and 6 indicate a similar level of ubiquitination regardless of whether the protein is present in cytoplasm (lane 5) or nucleus (lane 6).

Figure 9:
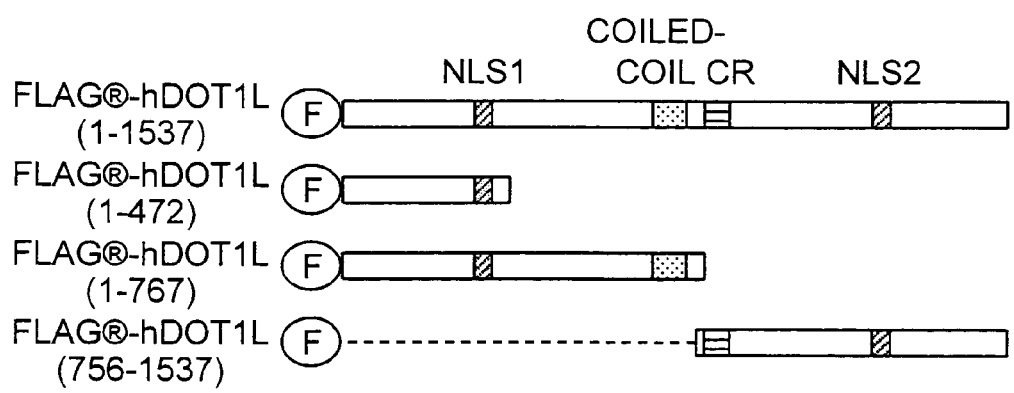

FIG. 9 illustrates that hDOT1L contains signals for nuclear and cytoplasm localization and presents a diagram of full-length and deletion hDOT1L constructs. NLS1 and NLS2 represent two nuclear localization signals (NLS) identified by the PredictNLS program. In addition, a coiled-coil and a region conserved between *Drosophila* and human DOT1L (CR) is also indicated.

FIGS. 10A-10E show the identification of the three nuclear export signals (NESs) in hDOT1L. (A) Diagram of the different EGFP-hDPT1L fusion constructs and summary of their nuclear exclusion patterns. "++", "+", and "−" represent strong, weak, and no nuclear exclusion, respectively. (B) Representative pictures of the constructs, shown in A, transfected into U2OS cells. (C) Top panel is a sequence alignment of NES1 (SEQ ID NO:12) and NES2 (SEQ ID NO:13) of hDOT1L with NES of protein kinase A inhibitor (PKI; SEQ ID NO:11). Conserved amino acids are underlined and amino acids mutated in NES1M are boxed. Bottom panels show mutation on the two C-terminal hydrophobic amino acids of NES1 (SEQ ID NO:14) disrupts NES1 function. (D) Demonstration of the NES1 function in hDOT1L localization in the context of full-length protein. (E) The function of each of the three NESs of hDOT1L can be blocked by LMB treatment.

Figure 11A:
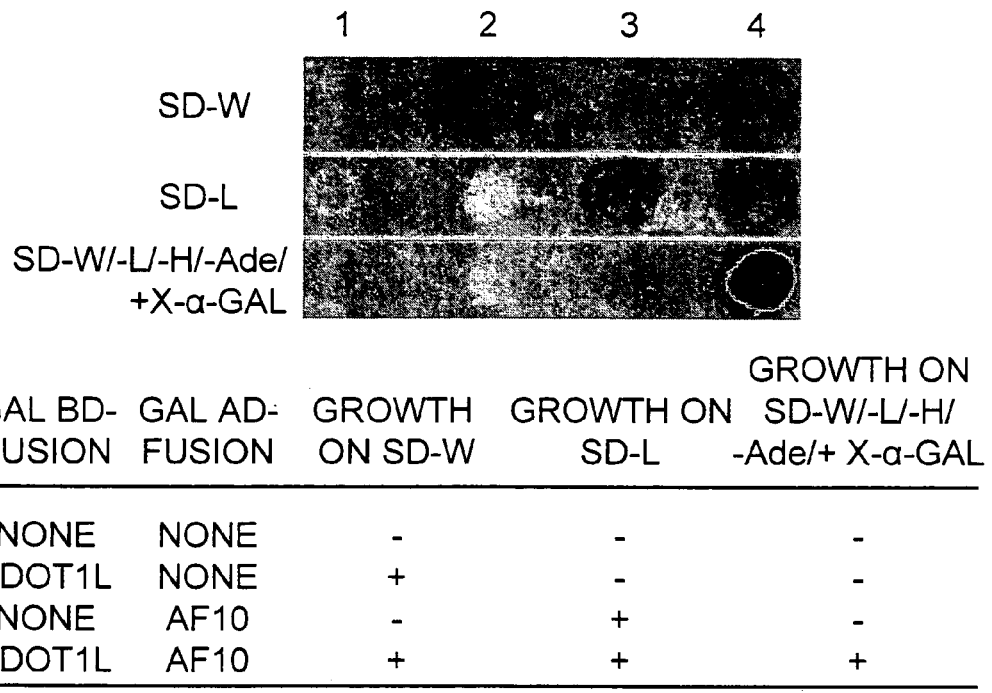
Figure 11B:
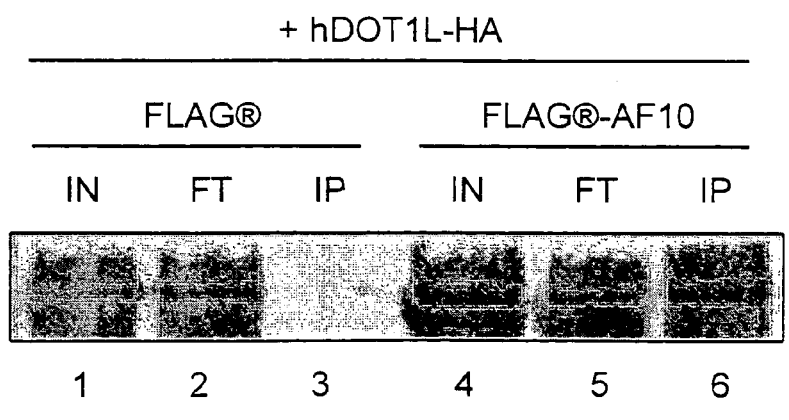

FIGS. 11A and 11B show the identification of AF10, a MLL fusion partner in leukemia, as an hDOT1L associated protein. (A) Yeast two-hybrid results demonstrating that only yeast cells containing both hDOT1L and AF10 plasmids could grow and form a blue colony on SD-Trp/-Leu/-His/-adenine/+X-α-Gal plates ("SD-W/-L/-H/-Ade/+X-α-Gal"). (B) AF10 and hDOT1L co-immunoprecipitate when co-expressed in 293T cells. FLAG® antibody was used for immunoprecipitation, and HA antibody was used for western blot analysis.

FIGS. 12A-12D show that the octapeptide motif and Leucine zipper (OM-LZ) region of AF10, required for leukemogenesis of MLL-AF10, is also required for hDOT1L and AF10 interaction. (A) Diagram of AF10 functional motifs and sequence alignment of the OM and LZ regions. Arrow indicates the break point for MLL-AF10 fusion. Human AF10 (AY598745; SEQ ID NO:15), and its homologs from mouse ("mAF10", O54826; SEQ ID NO:16), *Drosophila*, ("dAF10", Alhambra, AAF72595; SEQ ID NO:17), and *C. elegans* ("cAF10", Cezf, 2122400A; SEQ ID NO:18) were compared. Conserved amino acids are underlined. Mutations on the amino acids marked by * disrupt the interaction between hDOT1L and AF10. (B) Mammalian two-hybrid analysis identified the OM-LZ region of AF10 which is sufficient for mediating AF10 and hDOT1L interaction. (C) Co-immunoprecipitation experiments demonstrating that the OM-LZ region of AF10 is necessary for the AF10 and hDOT1L interaction. Western blot analysis shown on the left panel indicated that the wild-type and the deletion mutant proteins were expressed to a similar level. (D) Mammalian two-hybrid assays demonstrating that both the evolutionarily conserved octapeptide (Glu-Gln-Leu-Leu-Glu-Arg-Gln-Trp; SEQ ID NO:19) motif (OM) and the leucine zipper (LZ) of AF10 contribute to the interaction. The mutations are marked by * in panel A.

Figure 13A:
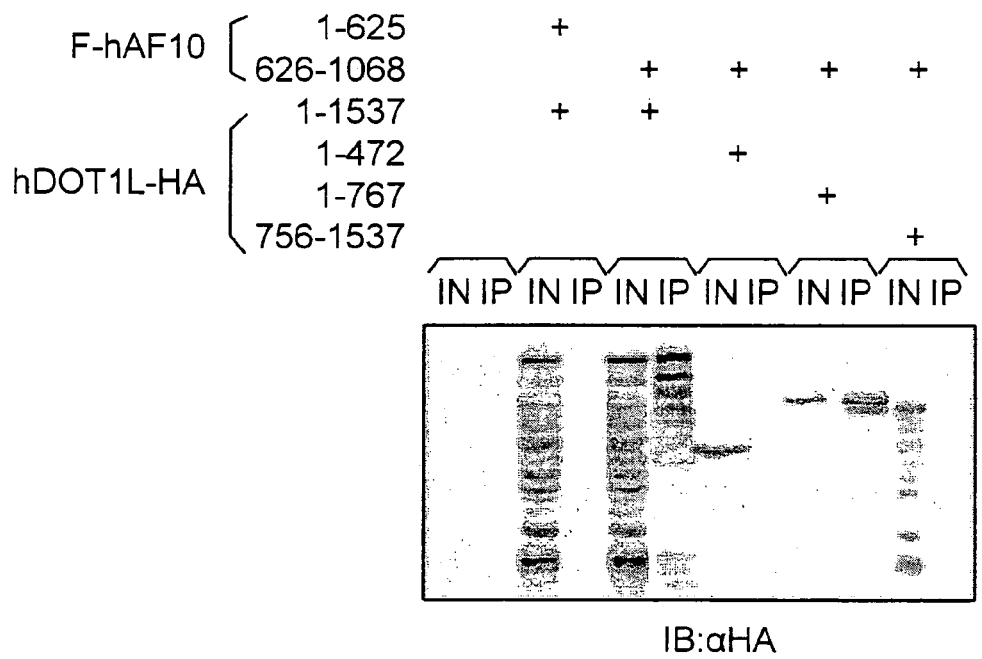
Figure 13B:
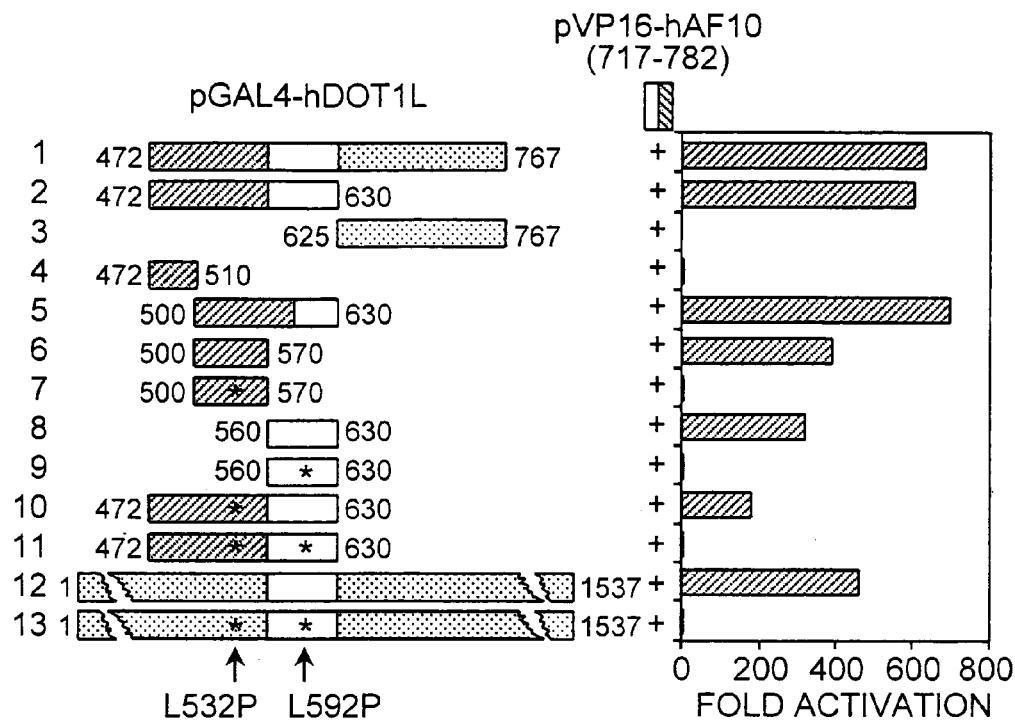

FIGS. 13A and 13B show that a leucine rich region in hDOT1L mediates the AF10 and hDOT1L interaction. (A) Co-immunoprecipitation assay identified a leucine rich region (amino acids 472-767) of hDOT1L to be important for AF10 and hDOT1L interaction. (B) Mammalian two-hybrid assays confirmed and further narrowed the interaction regions of hDOT1L to amino acids 500-630. In addition, mutagenesis studies demonstrated that leucines 532 and 592 are both important for the interaction. Numbers indicate the amino acid number of hDOT1L.

Figure 14A:
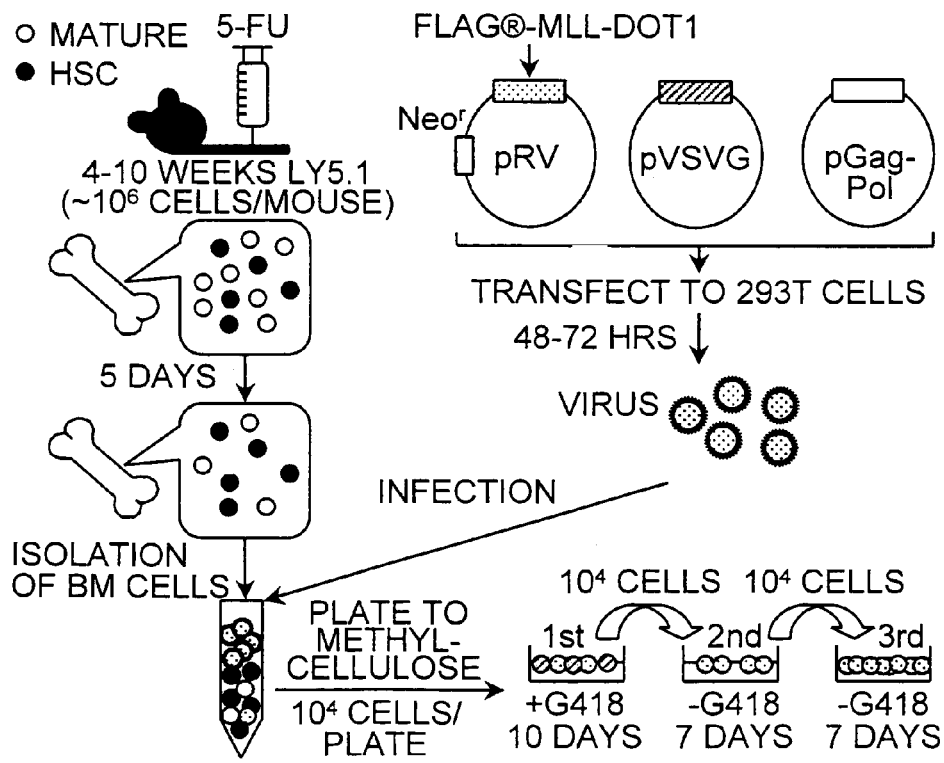
Figure 14B:
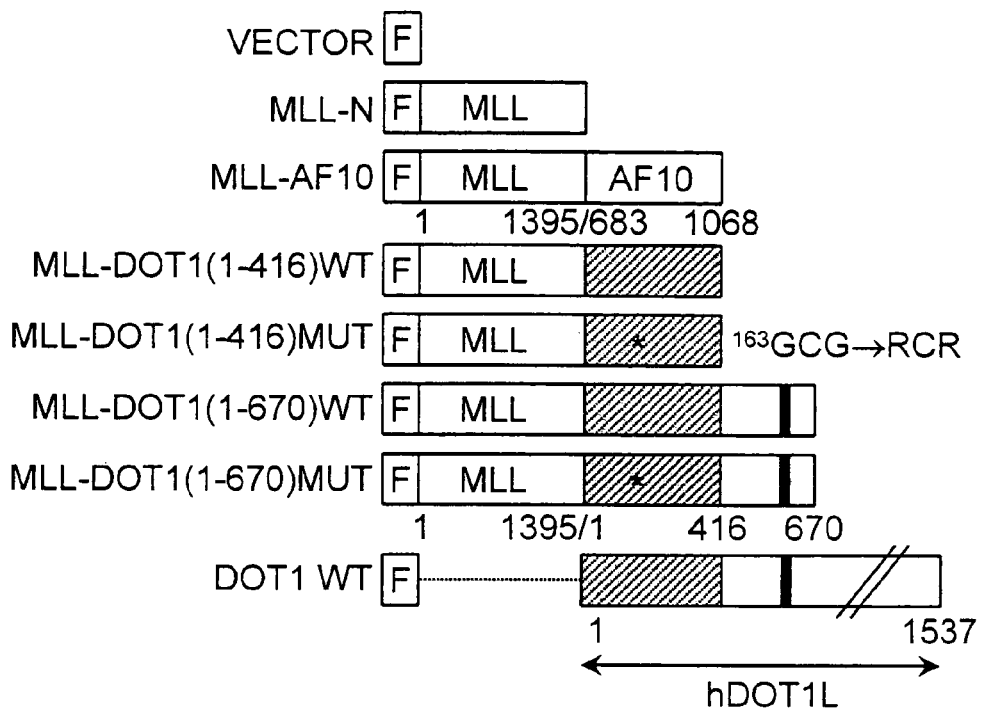
Figure 14C:
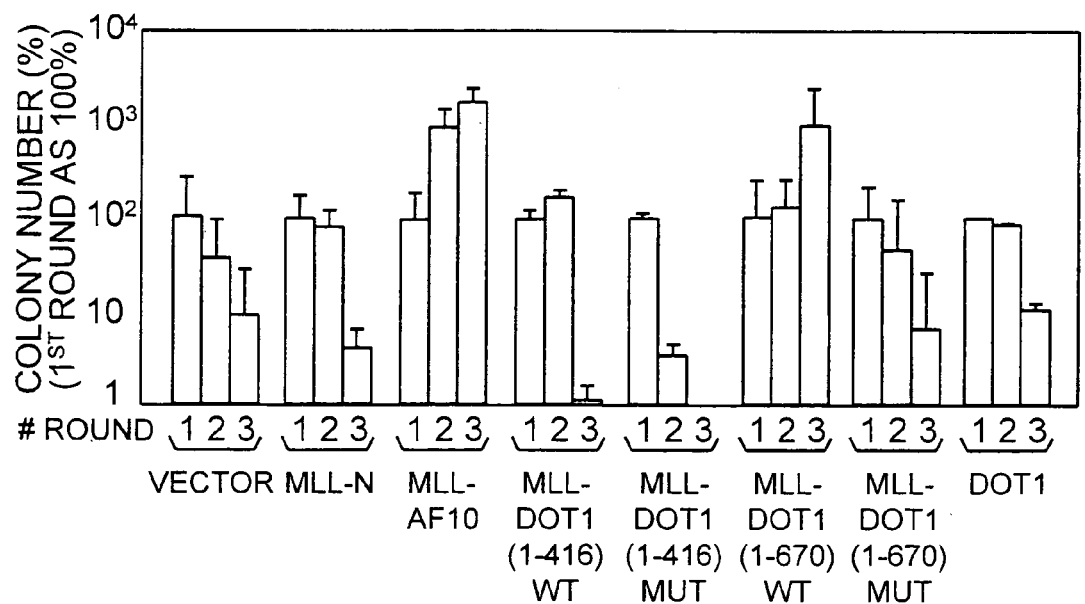

FIGS. 14A-14C shows that bone marrow transformation by MLL-hDOT1L requires the HMTase activity and a coiled-coil region (amino acids 416-670) of hDOT1L. (A) Schematic representation of the retroviral transduction procedures. (B) Diagram of retroviral constructs expressing MLL, MLL-AF10, and MLL-hDOT1L. The numbers refer to the amino acid number of corresponding proteins. The HMTase defective mutant (containing GCG to RCR change) is marked by *. (C) Relative colony numbers generated per $10^4$ transduced bone marrow cells in the first, second, and third round of plating. The various control and fusion proteins expressed are indicated. Data presented is the average of four independent experiments with error bars.

Figure 15A:
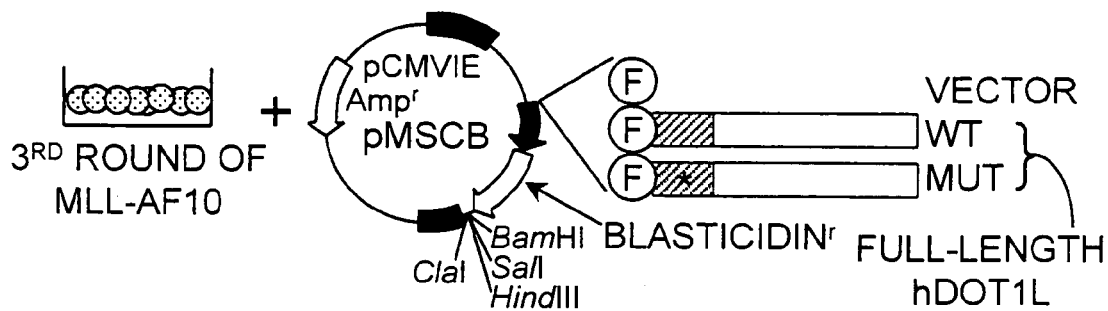
Figure 15B:
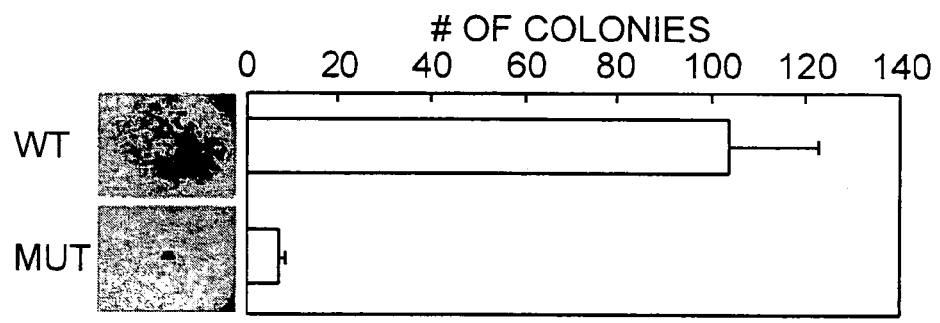

FIGS. 15A and 15B show that transduction of the HMTase-defective hDOT1L into MLL-AF10 transformed bone marrow cells attenuates the proliferation ability of the transformed cells. (A) Diagram depicting the assay. (B) Colony numbers generated from transduction of $10^4$ cells of the third round of MLL-AF10-transformed bone marrow cells with wild-type or HMTase-defective MLL-hDOT1L(1-670). Data presented is the average of two independent experiments with error bars.

Figure 16A:
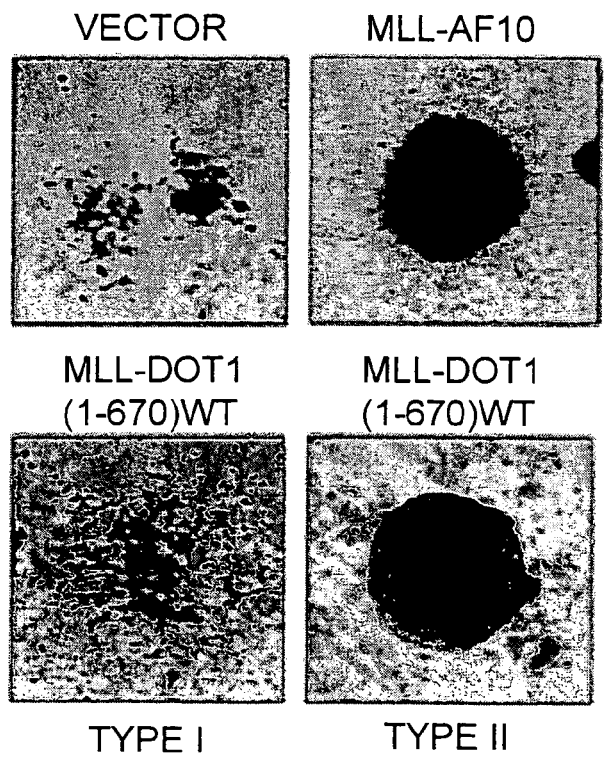
Figure 16B:
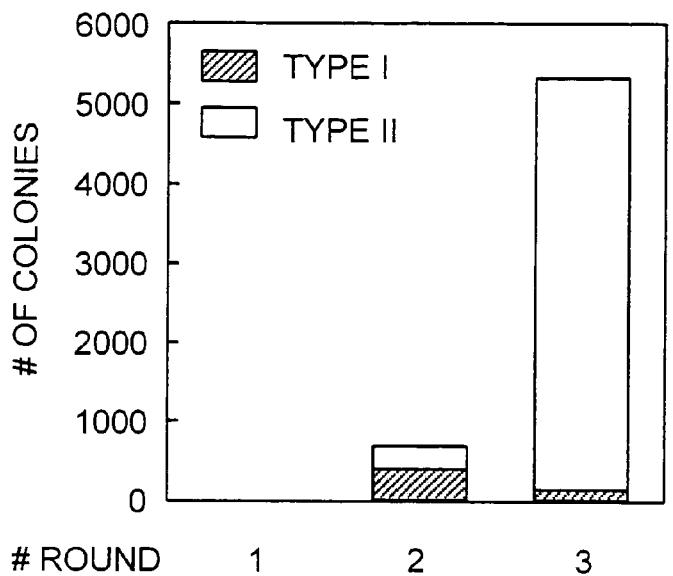
Figure 16C:
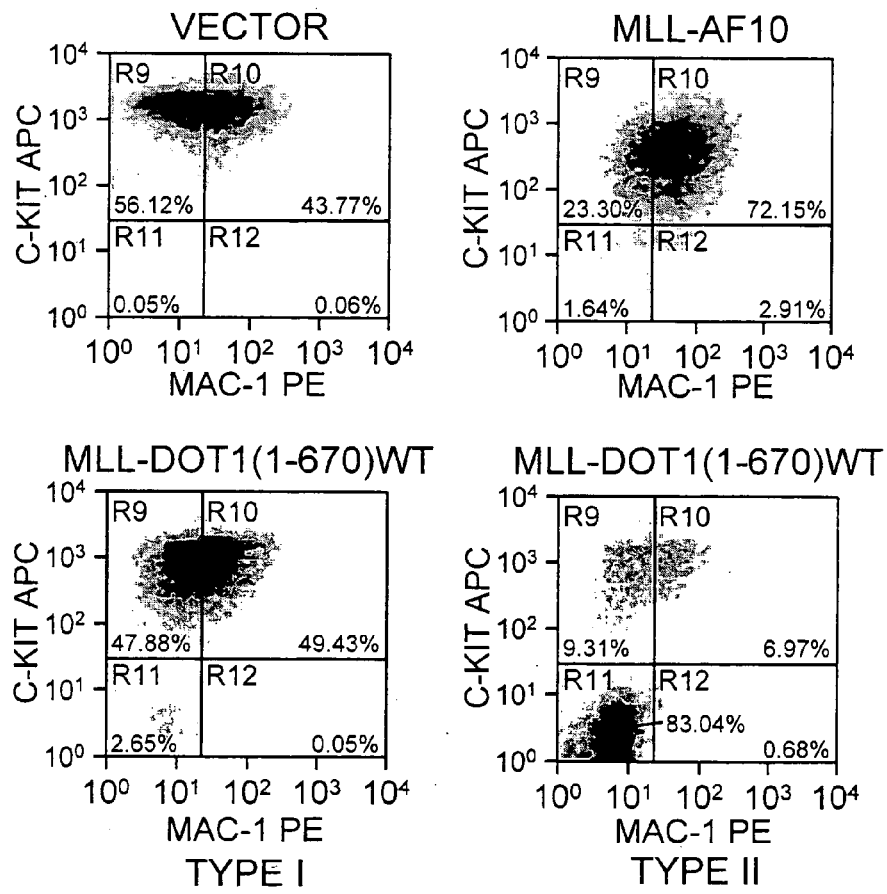

FIGS. 16A-16C show MLL-hDOT1L(1-670) immortalizes murine myeloid progenitors and uncharacterized cells. (A) Morphology of colonies formed in methylcellulose by MLL-AF10- and MLL-hDOT1L(1-670)-transduced cells. (B) Total and individual numbers of the two types of colonies formed in each round transduced by MLL-hDOT1L(1-670). (C) FACS analysis of the early myeloid markers, Mac1 and c-Kit, of the cells derived from second round plating of MLL-AF10- or hDOT1L(1-670)-transduced cells. Percent of cells expressing the indicated surface antigens is indicated.

Figure 17A:
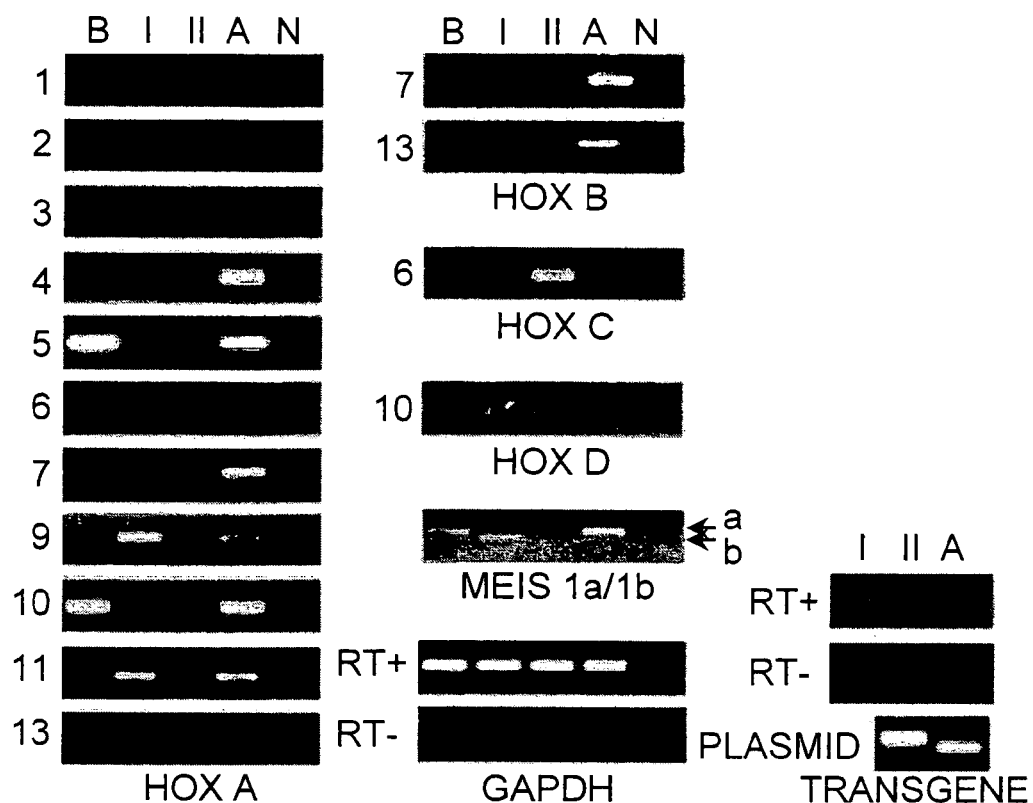
Figure 17B:
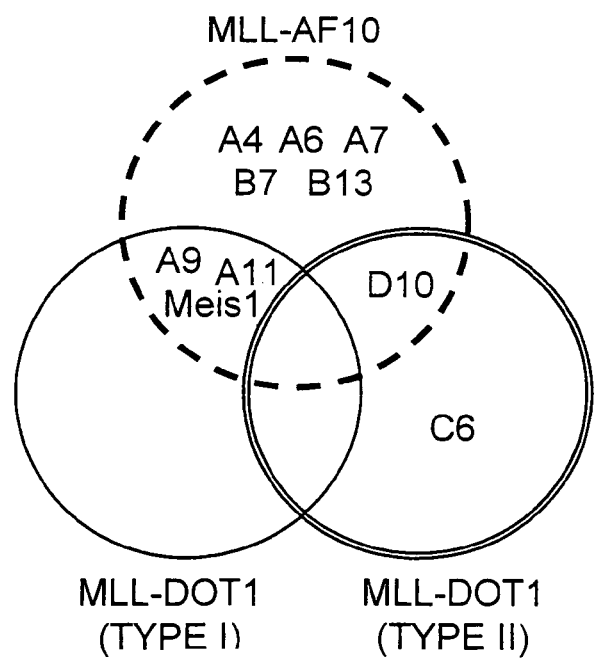

FIGS. 17A and 17B show a comparison of Hox gene expression patterns between primary bone marrow cells and MLL-AF10- or MLL-hDOT1L(1-670)-transduced cells. (A) RT-PCR showing expression response to MLL-AF10 or MLL-hDOT1L(1-670) transduction for each of the HoxA genes and other Hox genes. The expression patterns of the two Meis1 isoforms (a, b correspond to the upper and lower bands of the doublet, respectively) were also analyzed due to the reported collaborative role of Hoxa and Meis genes in myeloid leukemogenesis (Nakamura, et al. (1996) *Nat. Genet.* 12:149-153). GAPDH serves as a control for equal input in RT-PCR for different samples. Presence of MLL-AF10 or MLL-hDOT1L transgenes in the transformed cells was verified by PCR. "B" refers to primary bone marrow; "I" and "II" refer to the two different types of colonies arising from MLL-hDOT1L(1-670) transduction; "A" refers to colonies arising from MLL-AF10 transduction; "N" is a negative control for RT-PCR. (B) Summary of the genes overexpressed in transduced cells relative to none-transduced bone marrow cells analyzed in A.

Figure 18A:
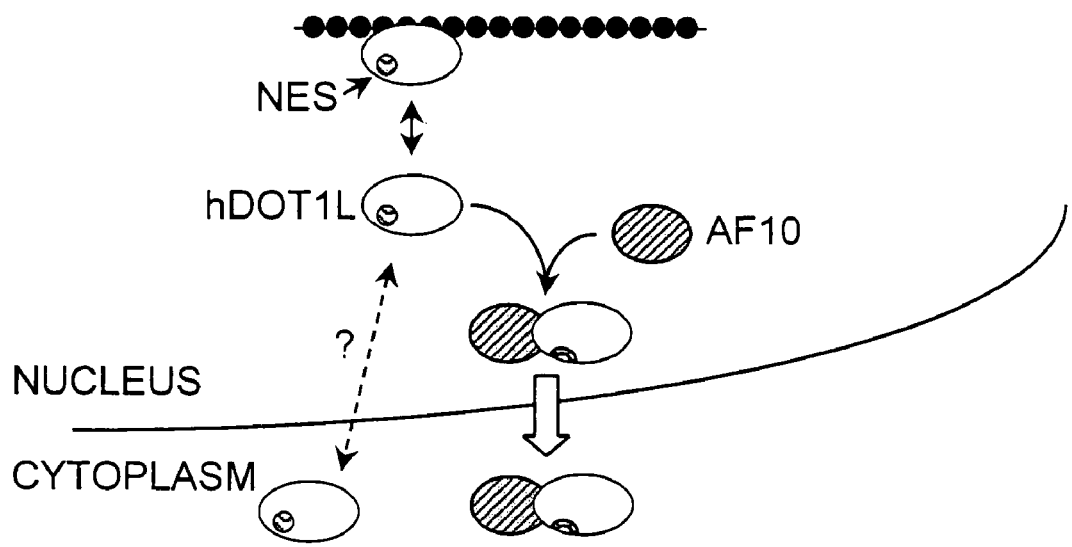
Figure 18B:
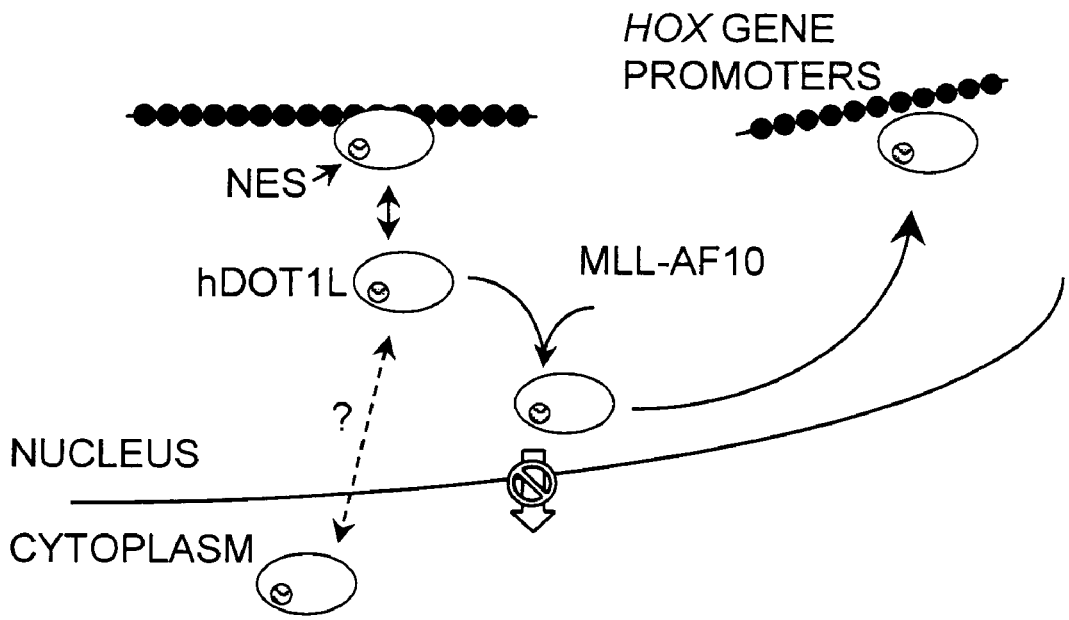

FIGS. 18A and 18B depict the relationship between hDOT1L, AF10, and MLL-AF10 in normal (A) and leukemia (B) cells.

DETAILED DESCRIPTION OF THE INVENTION

Chromatin structure is important in gene regulation and epigenetic inherence. It is known that post-translational modifications of histones are involved in the establishment and maintenance of higher-order chromatin structure; further, it has been reported that the tails of certain core histones are modified by acetylation, methylation, phosphorylation, ribosylation and ubiquitination. The present invention is based, in part, on the first identification of a post-translational modification within the globular domain of the histone. In particular, the inventors have observed methylation of lysine 79 of histone H3 ("H3-K79") and have identified a novel class of histone methyltransferase (HMTase) designated "DOT1" that methylates H3-K79 in vivo. DOT1L is a member of the DOT1 HTMase family (see, e.g., SEQ ID NO:2). Similar to other HMTases, the DOT1 polypeptide contain a S-adenosylmethionine (SAM) binding site and use SAM as a methyl donor. However, unlike other reported HMTases, the DOT1 polypeptides do not contain a SET domain.

The yeast homolog of DOT1 was originally identified as a Disruptor Of Telomeric silencing (the protein and nucleic acid sequences of yeast DOT1 can be found at Accession No. NP_010728; incorporated herein by reference in its entirety). The inventors have cloned and isolated the human DOT1 homolog, designated as hDOT1L (human DOT1-like protein), and determined that hDOT1L is an HMTase. The sequences of the human nucleic acid (SEQ ID NO:1) and protein (SEQ ID NO:2) have been deposited under GenBank accession number AF509504. Only the approximately 360 N-terminal amino acids of hDOT1L share significant sequence similarity with the yeast DOT1. The inventors have further identified DOT1 homologs from *C. elegans* (*C. elegans*, GenBank Accession number NP_510056 and CAA90610), *Drosophila* (GenBank Accession No. CG10272 and AAF54122), mouse (GenBank Accession No. XP_125730), *Anopheles gambiae* (GenBank Accession No. EAA03558), and *Neurospora crassa* (GenBank Accession No. EAA33634) from sequences in public databases (the disclosures of which are incorporated by reference herein in their entireties). The SAM binding domain among these homologs is conserved (approximately 30-100% amino acid sequence identity and 50-100% amino acid similarity [i.e., identical or conserved amino acids]; see FIG. 2A).

The 2.5 Å resolution structure of a fragment of the hDOT1L protein containing the catalytic domain (amino acids 1-416) has been solved. The atomic coordinates for amino acids 1-416 of hDOT1L have been determined and deposited in the RCSB database under ID code 1NW3 (see also, Min, et al. (2003) *Cell* 112:711-723), the disclosures of which are incorporated herein by reference in their entireties.

The present invention will now be described with reference to the accompanying drawings, in which preferred embodiments of the invention are shown. This invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

As used in the description of the invention and the appended claims, the singular forms "a," "an" and "the" are intended to include the plural forms as well, unless the context clearly indicates otherwise.

All publications, patent applications, patents, and other references mentioned herein are incorporated by reference in their entirety.

Except as otherwise indicated, standard methods can be used for the production of recombinant and synthetic polypeptides, fusion proteins, antibodies or antigen-binding fragments thereof, manipulation of nucleic acid sequences, production of transformed cells, and the like according to the present invention. Such techniques are known to those skilled in the art. See, e.g., SAMBROOK et al., MOLECULAR CLONING: A LABORATORY MANUAL 2nd Ed. (Cold Spring Harbor, N.Y., 1989); F. M. AUSUBEL et al. CURRENT PROTOCOLS IN MOLECULAR BIOLOGY (Green Publishing Associates, Inc. and John Wiley & Sons, Inc., New York).

I. DOT1L Polypeptides and Nucleic Acids

As one aspect, the present invention provides DOT1L polypeptides. As used herein, the term "polypeptide" includes both proteins and peptides. The term "DOT1L polypeptide" is intended to encompass the DOT1L polypeptides specifically described herein (e.g., SEQ ID NO:2) as well as functional equivalents thereof that have substantially similar amino acid sequences (as described below) to the DOT1L polypeptides specifically described herein (e.g., SEQ ID NO:2) and have one or more of the functional properties (also discussed below) of the DOT1L polypeptides specifically described herein. The term "DOT1L polypeptide" also encompasses functional fragments of the full-length DOT1L polypeptides specifically disclosed herein (e.g., SEQ ID NO:2) and functional equivalents thereof that have substantially similar amino acid sequences to a fragment of a full-length DOT1L polypeptide specifically disclosed herein (e.g., a fragment of SEQ ID NO:2) and have one or more of the functional properties of the DOT1L polypeptides specifically disclosed herein.

By "functional" it is meant that the DOT1L polypeptide has the same or substantially similar H3-K79 HMTase activity, SAM binding activity, histone and/or nucleosome binding activity, AF10 binding activity, AF10-MLL or other MLL fusion protein binding activity, leukemogenic activity and/or any other biological activity of interest as compared with a full-length DO1L polypeptide (e.g., SEQ ID NO:2). To illustrate, in representative embodiments, a functionally equivalent DOT1L polypeptide or functional DOT1L fragment has at least about 50%, 75%, 85%, 90%, 95% or 98% or more of the relevant biological activity(ies) as the DOT1L polypeptide of SEQ ID NO:2. Methods of assessing DOT1L binding to histones, nucleosomes, nucleic acids or polypeptides can be carried out using standard techniques that will be apparent to those skilled in the art (see the Examples for exemplary methods). Such methods include yeast and mammalian two-hybrid assays and co-immunoprecipitation techniques.

Other biological activities associated with DOT1L such as H3-K79 HMTase and leukemogenic activity can also be evaluated using standard methods known in the art, for example, as described in the Examples below.

In particular embodiments of the invention, the DOT1L polypeptide has H3-K79 specific HMTase activity. By H3-K79 "specific" HMTase activity it is meant that all, or essentially all, of the HMTase activity is directed to H3-K79 (e.g., using a histone or nucleosome substrate).

In particular embodiments of the invention, the functionally equivalent DOT1L polypeptide or functional DOT1L fragment has the same or substantially similar H3-K79 HMTase activity as the DOT1L polypeptide of SEQ ID NO:2 or the catalytically active fragment of amino acids 1-416 of SEQ ID NO:2. Methods of evaluating HMTase activity are known in the art, and are described in the Examples below. In representative embodiments, the functionally equivalent DOT1L polypeptide or functional DOT1L fragment has at least about 50%, 75%, 85%, 90%, 95% or 98% or more of the H3-K79 HMTase activity as the DOT1L polypeptide of SEQ ID NO:2 or the catalytically active fragment of amino acids 1-416 of SEQ ID NO:2.

An "isolated" polypeptide as used herein means a polypeptide that is separated or substantially free from at least some of the other components of the naturally occurring organism or virus, for example, the cell or viral structural components or other polypeptides or nucleic acids commonly found associated with the polypeptide. In particular embodiments, the "isolated" polypeptide is at least about 1%, 5%, 10%, 25%, 50%, 60%, 70%, 75%, 80%, 85%, 90%, 95%, 97%, 98%, 99% or more pure (w/w). In other embodiments, an "isolated" polypeptide indicates that at least about a 5-fold, 10-fold, 25-fold, 100-fold, 1000-fold, 10,000-fold, or more enrichment of the protein (w/w) is achieved as compared with the starting material.

The DOT1L polypeptides of the invention can be derived from any species of interest (e.g., mammalian [including but not limited to human, non-human primate, mouse, rat, lagomorph, bovine, ovine, caprine, porcine, equine, feline, canine, etc.], insect, yeast, avian, plants, etc.) as well as allelic variations, isoforms, splice variants and the like. The DOT1L sequences can further be wholly or partially synthetic.

In particular embodiments, the DOT1L polypeptide comprises, consists essentially of, or consists of an isolated DOT1L polypeptide of SEQ ID NO:2 or a functional fragment or functional equivalent thereof.

Functional equivalents of the DOT1L polypeptides of the invention encompass those that have substantial amino acid sequence similarity, for example, at least about 60%, 70%, 75%, 80%, 85%, 90%, 95%, 97% or more amino acid sequence similarity with the amino acid sequences specifically disclosed herein (e.g., SEQ ID NO:2) or a functional fragment thereof. Alternatively, nucleic acids encoding the DOT1L polypeptides of the invention have at least about 60%, 70%, 75%, 80%, 85%, 90%, 95%, 97% or more nucleotide sequence similarity with the nucleotide sequences encoding the DOT1L polypeptides specifically disclosed herein (e.g., SEQ ID NO:1) or a fragment thereof and encode a functional DOT1L polypeptide.

In alternate embodiments, nucleic acids encoding the DOT1L polypeptides of the invention have substantial nucleotide sequence similarity with the DOT1L nucleic acids specifically disclosed herein (e.g., SEQ ID NO:1) or fragments thereof and hybridize to the nucleic acid sequences disclosed herein (e.g., SEQ ID NO:1) or fragments thereof under standard conditions as known by those skilled in the art and encode a functional DOT1L polypeptide (including functional fragments).

For example, hybridization of such sequences may be carried out under conditions of reduced stringency, medium stringency or even stringent conditions (e.g., conditions represented by a wash stringency of 35-40% Formamide with 5× Denhardt's solution, 0.5% SDS and 1×SSPE at 37° C.; conditions represented by a wash stringency of 40-45% Formamide with 5× Denhardt's solution, 0.5% SDS, and 1×SSPE at 42° C.; and conditions represented by a wash stringency of 50% Formamide with 5× Denhardt's solution, 0.5% SDS and 1×SSPE at 42° C., respectively) to the nucleic acids encoding the DOT1L polypeptides (including functional fragments thereof) disclosed herein. See, e.g., Sambrook et al., *Molecular Cloning, A Laboratory Manual* (2d Ed. 1989) (Cold Spring Harbor Laboratory).

Further, it will be appreciated by those skilled in the art that there can be variability in the nucleic acids that encode the DOT1L polypeptides of the present invention due to the degeneracy of the genetic code. The degeneracy of the genetic code, which allows different nucleic acid sequences to code for the same protein, is well known in the art.

Likewise, those skilled in the art will appreciate that the present invention also encompasses fusion proteins (and nucleic acid sequences encoding the same) comprising the DOT1L polypeptides (including functional fragments) of the invention. For example, it may be useful to express the DOT1L polypeptides as a fusion protein that can be recognized by a commercially available antibody (e.g., FLAG motifs) or as a fusion protein that can otherwise be more easily purified (e.g., by addition of a poly-His tail). Additionally, fusion proteins that enhance the stability of the protein may be produced, e.g., fusion proteins comprising maltose binding protein (MBP) or glutathione-S-transferase. As another alternative, the fusion protein can comprise a reporter molecule. In other particular embodiments, the DOT1L fusion protein is a DOT1L-MLL fusion (see, e.g., Example 8). DOT1L fusion proteins can also be generated for use in yeast two-hybrid systems (e.g., GAL4-DOT1L fusions), as known in the art.

It will further be understood that the DOT1L polypeptides specifically disclosed herein will typically tolerate substitutions in the amino acid sequence and substantially retain biological activity. To routinely identify polypeptides of the invention other than those specifically disclosed herein, amino acid substitutions may be based on any characteristic known in the art, including the relative similarity or differences of the amino acid side-chain substituents, for example, their hydrophobicity, hydrophilicity, charge, size, and the like. In particular embodiments, conservative substitutions (i.e., substitution with an amino acid residue having similar properties) are made in the amino acid sequence encoding the DOT1L polypeptide.

In making amino acid substitutions, the hydropathic index of amino acids can be considered. The importance of the hydropathic amino acid index in conferring interactive biologic function on a protein is generally understood in the art (see, Kyte and Doolittle, (1982) *J. Mol. Biol.* 157:105; incorporated herein by reference in its entirety). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics (Kyte and Doolittle, Id.), and these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is also understood in the art that the substitution of amino acids can be made on the basis of hydrophilicity. U.S. Pat. No. 4,554,101 (incorporated herein by reference in its entirety) states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (±3.0); aspartate (+3.0±1); glutamate (+3.0±1); serine (+0.3); asparagine (+0.2); glutamine (+0.2); glycine (0); threonine (−0.4); proline (−0.5±I); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

As is known in the art, a number of different programs can be used to identify whether a nucleic acid or polypeptide has sequence identity or similarity to a known sequence. One example of a useful algorithm is the BLAST algorithm, described in Altschul et al., *J. Mol. Biol.* 215, 403-410, (1990) and Karlin et al., *Proc. Natl. Acad. Sci. USA* 90, 5873-5787 (1993). A particularly useful BLAST program is the WU-BLAST-2 program which was obtained from Altschul et al., *Methods in Enzymology*, 266, 460-480 (1996). WU-BLAST-2 uses several search parameters, which are preferably set to the default values. The parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., (1997) *Nucleic Acids Res.* 25, 3389-3402.

The CLUSTAL program can also be used to determine sequence similarity. This algorithm is described by Higgins et al. (1988) *Gene* 73:237; Higgins et al. (1989) *CABIOS* 5:151-153; Corpet et al. (1988) *Nucleic Acids Res.* 16: 10881-90; Huang et al. (1992) *CABIOS* 8: 155-65; and Pearson et al. (1994) *Meth. Mol. Biol.* 24: 307-331.

The DOT1L polypeptides of the present invention also encompass functional DOT1L polypeptide fragments (e.g., having HMTase activity, having SAM binding activity, histone or nucleosome binding activity, AF10 binding activity, AF10-MLL or any other MLL fusion protein binding activity, leukemogenic activity and/or any other biological activity of interest), and functional equivalents thereof. The length of the DOT1L fragment is not critical. Illustrative functional DOT1L protein fragments comprise at least about 80, 100, 200, 300, 400, 500, 600, 700, 800, 1000, 1200, 1400 or more amino acids (optionally, contiguous amino acids) of a DOT1L polypeptide. The invention also provides nucleic acids encoding the functional DOT1L fragments. Exemplary nucleic acids encoding functional DOT1L fragments comprise at least about 250, 300, 400, 500, 600, 700, 800, 1000, 1500, 2000, 2500, 3000, 4000 or more nucleotide bases (optionally, contiguous bases) of a nucleic acid encoding a full-length DOT1L polypeptide.

In particular embodiments, the invention provides functional DOT1L fragments comprising the catalytic domain comprising the SAM binding domain (as well as adjacent sequences) and nucleic acids encoding the same. In representative embodiments, the functional DOT1L fragment comprises a catalytically active fragment comprising amino acids 157 to 270 of SEQ ID NO:2 or a functional equivalent thereof. In other embodiments, the DOT1L fragment comprises a catalytically active fragment comprising amino acids 121-306 or amino acids 1-416 of SEQ ID NO:2 or a functional equivalent of either of the foregoing.

The functional DOT1L fragment comprising the catalytic domain can optionally further comprise the DOT1L positively charged region (e.g., amino acids 390 to 407 of SEQ ID NO:2 or a functional equivalent thereof.

In other embodiments, the functional fragment comprises the DOT1L leucine rich interaction domain with AF10 (e.g., amino acids 500-630 of SEQ ID NO:2 or a functional equivalent thereof). As a further embodiment, the functional fragment comprises the leucine zipper region at amino acids 564-590 of SEQ ID NO:2 and/or the coiled coil region at amino acids 561-660 of SEQ ID NO:2 or functional equivalents of either of the foregoing.

In still other embodiments, the invention provides a functional DOT1L fragment comprising a nuclear export signal. In illustrative embodiments, the nuclear export signal comprises amino acids 482-496 of SEQ ID NO:2 or a functional equivalent thereof, amino acids 600-635 of SEQ ID NO:2 or a functional equivalent thereof and/or amino acids 636-650 of SEQ ID NO:2 or a functional equivalent thereof. In other embodiments, the nucl ear export signal comprises amino acids 472-767 of SEQ ID NO:2 or a functional fragment thereof.

Those skilled in the art will appreciate that functional DOT1L fragments can comprise two or more of the functional regions discussed above.

In yet a further embodiment, the functional fragment comprises the N-terminal portion of a DOT1 polypeptide (e.g., SEQ ID NO:2), for example, approximately the N-terminal 10, 20, 30, 40, 50, 60, 70, 80, 90 or 100 amino acids. In other embodiments, the functional fragment is truncated at the N-terminus, e.g., less than about 100, 85, 75, 60, 50, 35, 20, 15, 10 or 5 amino acids are truncated from the N-terminus.

The invention also provides isolated nucleic acids encoding the DOT1L polypeptides of the invention. The nucleic acid can be DNA, RNA or chimeras thereof, single stranded or double-stranded, and can be fully or partially synthetic or naturally occurring. The nucleic acids can comprise modified nucleotides or nucleotide analogs as are well-known in the art. Further, the nucleic acid can be from any species of origin, including but not limited to mammalian species such as human, non-human primate, mouse, rat, rabbit, cattle, goat, sheep, horse, pig, dog, cat, etc. and avian species.

In particular embodiments, the nucleic acid is an isolated nucleic acid. As used herein, an "isolated" nucleic acid means a nucleic acid separated or substantially free from at least some of the other components of the naturally occurring organism, such as for example, the cell structural components or other polypeptides or nucleic acids commonly found associated with the nucleic acid.

In representative embodiments, the invention provides an isolated DOT1L polypeptide comprising an amino acid sequence selected from the group consisting of: (a) the amino acid sequence of SEQ ID NO:2; (b) an amino acid sequence having at least about 60%, 70%, 75%, 80%, 85%, 90%, 95%, 97% or more amino acid sequence similarity with the amino acid sequence of SEQ ID NO:2, wherein the DOT1L polypeptide has H3-K79 methyltransferase activity; and (c) a functional fragment of at least about 100, 200, 300, 400, 500, 600, 700, 800, 1000, 1200, 1400 or more amino acids of the amino acid sequence of (a) or (b) above, wherein the functional fragment comprises a DOT1L histone methyltransferase catalytic domain and has H3-K79 methyltransferase activity.

In other illustrative embodiments, the invention provides an isolated nucleic acid comprising a nucleotide sequence encoding a DOT1L polypeptide, the nucleotide sequence selected from the group consisting of: (a) a nucleotide sequence comprising the nucleotide sequence of SEQ ID NO:1; (b) a nucleotide sequence that hybridizes to the complete complement of a nucleotide sequence comprising the nucleotide sequence of SEQ ID NO:1 under stringent conditions (as defined above), wherein the nucleotide sequence encodes a polypeptide having H3-K79 methyltransferase activity; (c) a nucleotide sequence having at least about 60%, 70%, 75%, 80%, 85%, 90%, 95%, 97% or more nucleotide sequence similarity with the nucleotide sequence of SEQ ID NO:1, wherein the nucleotide sequence encodes a polypeptide having H3-K79 methyltransferase activity; (d) a nucleotide sequence that differs from the nucleotide sequence of (a) above due to the degeneracy of the genetic code; (f) a nucleotide sequence comprising a functional fragment of SEQ ID NO:1, wherein the functional fragment comprises at least the coding region of the histone methyltransferase catalytic domain of SEQ ID NO:1 or a nucleotide sequence that hybridizes to the complete complement coding region of the histone methyltransferase catalytic domain of SEQ ID NO:1 under stringent conditions, and wherein the functional fragment encodes a polypeptide having H3-K79 methyltransferase activity; (g) a nucleotide sequence comprising a functional fragment of SEQ ID NO:1, wherein the functional fragment comprises at least the coding region of the histone methyltransferase catalytic domain of SEQ ID NO:1 or a nucleotide sequence having at least about 60%, 70%, 75%, 80%, 85%, 90%, 95%, 97% or more nucleotide sequence similarity thereto, and wherein the functional fragment encodes a polypeptide having H3-K79 methyltransferase activity; and (h) a nucleotide sequence comprising a functional fragment of SEQ ID NO:1, wherein the functional fragment comprises at least the coding region of the histone methyltransferase catalytic domain of SEQ ID NO:1 or a nucleotide sequence that differs therefrom due to the degeneracy of the genetic code; and wherein the functional fragment encodes a polypeptide having H3-K79 methyltransferase activity.

As yet a further embodiment, the invention provides antisense oligonucleotides and siRNA that hybridize to the DOT1L nucleic acids of the invention (e.g., under stringent hybridization conditions as defined above) and inhibit production of DOT1L polypeptide. RNAi is a mechanism of post-transcriptional gene silencing in which double-stranded RNA (dsRNA) corresponding to a coding sequence of interest is introduced into a cell or an organism, resulting in degradation of the corresponding mRNA. The RNAi effect persists for multiple cell divisions before gene expression is regained. RNAi is therefore a powerful method for making targeted knockouts or "knockdowns" at the RNA level. RNAi has proven successful in human cells, including human embryonic kidney and HeLa cells (see, e.g., Elbashir et al., *Nature* (2001) 411:494-8). In one embodiment, silencing can be induced in mammalian cells by enforcing endogenous expression of RNA hairpins (see Paddison et al., (2002), *PNAS USA* 99:1443-1448). In another embodiment, transfection of small (e.g., 21-23 nt) dsRNA specifically inhibits nucleic acid expression (reviewed in Caplen, (2002) *Trends in Biotechnology* 20:49-51).

The mechanism by which RNAi achieves gene silencing has been reviewed in Sharp et al, (2001) *Genes Dev* 15: 485-490; and Hammond et al., (2001) *Nature Rev Gen* 2:110-119).

RNAi technology utilizes standard molecular biology methods. To illustrate, dsRNA corresponding to all or a part of a target coding sequence to be inactivated can be produced by standard methods, e.g., by simultaneous transcription of both strands of a template DNA (corresponding to the target sequence) with T7 RNA polymerase. Kits for production of dsRNA for use in RNAi are available commercially, e.g., from New England Biolabs, Inc. Methods of transfection of dsRNA or plasmids engineered to make dsRNA are routine in the art.

Silencing effects similar to those produced by RNAi have been reported in mammalian cells with transfection of a mRNA-cDNA hybrid construct (Lin et al., (2001) *Biochem Biophys Res Commun* 281:639-44), providing yet another strategy for silencing a coding sequence of interest.

In particular embodiments, the invention provides antisense oligonucleotides and siRNA that have at least about 60%, 70%, 80%, 85%, 90%, 95%, 98%, 99% or 100% sequence identity with the DOT1L nucleic acids described above. Methods of making and using antisense oligonucleotides and siRNA are known in the art. There is no particular upper or lower limit to the antisense oligonucleotide or siRNA. Illustrative antisense oligonucleotides or siRNA will be about 8, 10, 12, 15, 18, 20, 25, 30, 40, 50, 60, 75, 90, 100, 125 or 150 or more bases in length.

The invention also provides vectors, including expression vectors and gene delivery vectors, comprising the nucleic acids of the invention. Suitable vectors include bacterial expression vectors, fungal expression vectors, mammalian vectors, yeast expression vectors and plant expression vectors. Exemplary vectors include bacterial artificial chromosomes, cosmids, yeast artificial chromosomes, phage, plasmids, lipid vectors and viral vectors (e.g., adenovirus, adeno-associated virus, retrovirus, baculovirus, and the like).

Expression vectors can be designed for expression of polypeptides in prokaryotic or eukaryotic cells. For example, polypeptides can be expressed in bacterial cells such as *E. coli*, yeast cells, insect cells (e.g., in the baculovirus expression system) or mammalian cells. Some suitable host cells are discussed further in Goeddel, Gene Expression Technology: Methods in Enzymology 185, Academic Press, San Diego, Calif. (1990). Examples of vectors for expression in yeast *S. cerevisiae* include pYepSecl (Baldari et al., (1987) *EMBO J.* 6:229-234), pMFa (Kurjan and Herskowitz, (1982) *Cell* 30:933-943), pJRY88 (Schultz et al., (1987) *Gene* 54:113-123), and pYES2 (Invitrogen Corporation, San Diego, Calif.). Baculovirus vectors available for expression of nucleic acids to produce proteins in cultured insect cells (e.g., Sf 9 cells) include the pAc series (Smith et al., (1983) *Mol. Cell. Biol.* 3:2156-2165) and the pVL series (Lucklow, V. A., and Summers, M. d. (1989) *Virology* 170:31-39).

Examples of mammalian expression vectors include pCDM8 (Seed, (1987) *Nature* 329:840) and pMT2PC (Kaufman et al. (1987), *EMBO J.* 6:187-195).

The vector generally comprises an expression control element (e.g., a promoter) operably associated with the nucleic acids of the invention. It will be appreciated that a variety of expression control elements can be used depending on the level and tissue-specific expression desired. Further, the promoter can be constitutive or inducible (e.g., the metalothionein promoter or a hormone inducible promoter). The expression control element can be native or foreign to the host cell and can be a natural or a synthetic sequence. The promoter is generally chosen so that it will function in the target cell(s) of interest. The nucleic acids can further be associated with other appropriate expression control sequences, e.g., transcription/translation control signals and polyadenylation signals. Viral regulatory elements are often employed in mammalian cells. For example, commonly used promoters in mammalian expression vectors are derived from polyoma, adenovirus 2, cytomegalovirus and Simian Virus 40.

Moreover, specific initiation signals are generally required for efficient translation of inserted protein coding sequences.

These translational control sequences, which can include the ATG initiation codon and adjacent sequences, can be of a variety of origins, both natural and synthetic. Further provided are host cells (e.g., yeast, bacterial, mammalian, insect, plant or fungal cells) comprising the isolated nucleic acids and vectors of the invention. The cell can be transiently or stably transformed with the nucleic acid or vector of the invention. In particular embodiments, a host cell is transiently or stably (e.g., by stable integration into the genome of the cell or by a stably maintained episome) transformed with a nucleic acid of the invention.

Further, the cell can be cultured (i.e., isolated) or can be a cell in situ in a living organism.

Still another aspect of the invention is a transgenic non-human animal (e.g., non-human mammal) comprising a recombinant nucleic acid encoding a DOT1L polypeptide or a functional fragment thereof. In alternative embodiments, the transgenic non-human animal comprises a recombinant nucleic acid encoding an antisense oligonucleotide or siRNA that inhibits production of DOT1L polypeptide. Generally, the transgenic non-human animal will be stably transformed with the nucleic acid, e.g., by stable integration into the genome of the animal. The transgenic non-human animal can be of any species of interest including but not limited to mouse, rat, guinea pig, rabbit, pig, horse, goat, sheep, cow, cat, dog, monkey, hamster, chicken and the like. Methods of making transgenic non-human animals are known in the art.

As yet a further embodiment, the invention provides antibodies and antibody fragments that specifically bind to the DOT1L polypeptides of the invention.

The term "antibody" or "antibodies" as used herein refers to all types of immunoglobulins, including IgG, IgM, IgA, IgD, and IgE. The antibody can be monoclonal or polyclonal and can be of any species of origin, including (for example) mouse, rat, rabbit, horse, goat, sheep or human, or can be a chimeric antibody. See, e.g., Walker et al., *Molec. Immunol.* 26, 403-11 (1989). The antibodies can be recombinant monoclonal antibodies produced according to the methods disclosed in U.S. Pat. No. 4,474,893 or U.S. Pat. No. 4,816,567. The antibodies can also be chemically constructed according to the method disclosed in U.S. Pat. No. 4,676,980.

Antibody fragments included within the scope of the present invention include, for example, Fab, F(ab')2, and Fc fragments, and the corresponding fragments obtained from antibodies other than IgG. Such fragments can be produced by known techniques. For example, F(ab')2 fragments can be produced by pepsin digestion of the antibody molecule, and Fab fragments can be generated by reducing the disulfide bridges of the F(ab')2 fragments. Alternatively, Fab expression libraries can be constructed to allow rapid and easy identification of monoclonal Fab fragments with the desired specificity (Huse et al., (1989) *Science* 254, 1275-1281).

Monoclonal antibodies used to carry out the present invention can be produced in a hybridoma cell line according to the technique of Kohler and Milstein, (1975) *Nature* 265, 495-97. For example, a solution containing the appropriate antigen can be injected into a mouse and, after a sufficient time, the mouse sacrificed and spleen cells obtained. The spleen cells are then immortalized by fusing them with myeloma cells or with lymphoma cells, typically in the presence of polyethylene glycol, to produce hybridoma cells. The hybridoma cells are then grown in a suitable medium and the supernatant screened for monoclonal antibodies having the desired specificity. Monoclonal Fab fragments can be produced in *E. coli* by recombinant techniques known to those skilled in the art. See, e.g., W. Huse, (1989) *Science* 246, 1275-81.

Antibodies specific to the target polypeptide can also be obtained by phage display techniques known in the art.

Methods of Use.

The DOT1L polypeptides and nucleic acids of the invention can be used in a number of research, diagnostic and/or therapeutic applications.

To illustrate, the inventive DOT1L polypeptides and nucleic acids can be used to screen for compounds that bind to and/or modulate (e.g., increase or decrease) one or more biological activities of DOT1L, including but not limited to H3-K79 HMTase activity, SAM binding activity, histone and/or nucleosome binding activity, AF10 binding activity, AF10-MLL or other MLL fusion protein binding activity, leukemogenic activity and/or any other biological activity of interest. As described above, the DOT1L polypeptide can be a functional fragment of a full-length DO1L polypeptide or functional equivalent thereof and can comprise any DOT1 domain of interest, including but not limited to the catalytic domain, the SAM binding domain and/or the positively charged domain, the AF10 interaction domain and/or a nuclear export signal.

In particular embodiments, the compound enhances, elevates, increases (or similar terms) one or more biological activities of DOT1L (e.g., by at least about 25%, 50%, 75%, 2-fold, 3-fold, 5-fold, 10-fold, 15-fold, 20-fold or more). In other embodiments, the compound is an inhibitor that reduces, inhibits, decreases (or similar terms) of one or more biological activities of DOT1L (e.g., by at least about 25%, 40%, 50%, 60%, 75%, 80%, 85%, 90%, 95%, 98% or more). In particular embodiments, an inhibitory compound results in no detectable level of the DOT1L biological activity(ies) of interest.

In one particular embodiment, the invention provides a method of identifying a compound that modulates (e.g., inhibits or enhances) DOT1L polypeptide binding to a histone or nucleosome substrate comprising H3, the method comprising: contacting a DOT1L polypeptide with a histone nucleosome substrate comprising H3 in the presence of a test compound; detecting the binding of the DOT1L polypeptide to the substrate under conditions sufficient for binding of the DOT1L polypeptide to the substrate, wherein an elevation or reduction in DOT1L polypeptide binding to the substrate in the presence of the test compound as compared with the level of binding in the absence of the test compound indicates that the test compound modulates binding of DOT1L polypeptide to a histone or nucleosome substrate comprising H3.

In another embodiment, the invention provides a method of identifying a compound that modulates a biological activity (as described above) of a DOT1L polypeptide, the method comprising: contacting a DOT1L polypeptide with a histone or nucleosome substrate comprising H3 in the presence of a test compound; detecting the level of the DOT1L activity of interest under conditions sufficient for the DOT1L polypeptide to exhibit the relevant biological activity, wherein an elevation or reduction in the DOT1L activity in the presence of the test compound as compared with the level in the absence of the test compound indicates that the test compound modulates DOT1L biological activity.

In a further embodiment, the invention provides a method of identifying a compound that modulates DOT1L H3-K79 HMTase activity, the method comprising: contacting a DOT1L polypeptide with a histone or nucleosome substrate comprising H3 in the presence of a test compound; detecting the level of H3-K79 methylation of the histone or nucleosome substrate under conditions sufficient to provide H3-K79 methylation, wherein an elevation or reduction in H3-K79 methylation in the presence of the test compound as compared with the level of histone H3-K79 methylation in the absence of the test compound indicates that the test compound modulates DOT1L H3-K79 HMTase activity.

The inventors have discovered that DOT1L has a number of binding partners including AF10 and MLL fusion proteins (e.g., AF10-MLL), which are implicated in leukemogenesis (described in more detail below). Thus, as another aspect, the invention provides a method of identifying a compound that inhibits binding of DOT1L polypeptide to a second polypeptide, the method comprising: contacting a DOT1L polypeptide of the invention with a second polypeptide in the presence of a test compound; detecting the level of binding between DOT1L polypeptide and the second polypeptide under conditions sufficient for binding of DOT1L polypeptide to the second polypeptide, wherein a reduction in binding between DOT1L polypeptide and the second polypeptide in the presence of the test compound as compared with the level of binding in the absence of the test compound indicates that the test compound inhibits binding of DOT1L polypeptide to the second polypeptide.

In particular embodiments, the second polypeptide is AF10 (including AF10 fragments comprising the OM-LZ domain, e.g., amino acids 719-800 of AF10 [human AF10 sequence, Accession No. AY598745; mouse AF10 sequence, Accession No. 054826]; the disclosures of which are incorporated herein by reference in their entireties). In other representative embodiments, the second polypeptide is an MLL fusion protein (e.g., an MLL-AF10 fusion protein or an MLL-ENL, MLL-ELL or MLL-CBP fusion protein).

In other particular embodiments, the DOT1L polypeptide (including functional fragments) comprises amino acids 500 to 630 of SEQ ID NO:2 or an amino acid sequence having at least 95% amino acid sequence similarity thereto.

The present invention further provides methods of identifying compounds for the treatment and/or prevention of leukemia by identifying compounds that bind to and/or modulate the biological activity (as described above) of a DOT1 polypeptide.

In one embodiment, the invention provides a method of identifying a candidate compound for the prevention and/or treatment of leukemia, the method comprising: contacting a DOT1L polypeptide of the invention with a histone or nucleosome substrate comprising histone H3 in the presence of a test compound; detecting the level of H3-K79 methylation of the substrate under conditions sufficient to provide H3-K79 methylation, wherein an inhibition of H3-K79 methylation in the presence of the test compound as compared with the level of H3-K79 methylation in the absence of the test compound indicates that the test compound is a candidate compound for the prevention and/or treatment of leukemia.

The invention further provides a method of identifying a candidate compound for the prevention and/or treatment of leukemia, comprising: contacting a DOT1L polypeptide of the invention with AF10 or an MLL fusion protein; detecting the level of binding between the DOT1L polypeptide and AF10 or MLL fusion protein under conditions sufficient for binding therebetween, wherein a reduction in binding between DOT1L polypeptide and AF10 or the MLL fusion protein in the presence of the test compound as compared with the level of binding in the absence of the test compound indicates that the test compound is a candidate compound for the prevention and/or treatment of leukemia.

In particular embodiments, the MLL fusion protein is an MLL-AF10 fusion protein or an MLL-ENL, MLL-ELL or MLL-CBP fusion protein.

In other representative embodiments, the DOT1L polypeptide (including functional fragments) comprises the DOT1L AF10 interaction domain, e.g., amino acids 500-630 of SEQ ID NO:2 or a functional equivalent thereof. Alternatively, DOT1L polypeptides comprising the leucine zipper region at amino acids 564-590 of SEQ ID NO:2 and/or the coiled coil region at amino acids 561 to 660 of SEQ ID NO:2 or functional equivalents of either of the foregoing can be used as targets to identify compounds that disrupt interactions between DOT1L and AF10 or an MLL fusion protein.

By the terms "treating leukemia" or "treatment of leukemia", it is intended that the severity of the disease is reduced. By the term "prevention of leukemia" or "preventing leukemia" it is intended that the methods at least partially eliminate or reduce the incidence or onset of leukemia. Alternatively stated, by treating or preventing leukemia (or grammatical variations thereof, it is meant that the methods and compounds of the invention slow, control, decrease the likelihood or probability, or delay the onset of leukemia in the subject.

Methods of assessing DOT1L binding to histones, nucleosomes, nucleic acids or polypeptides can be carried out using standard techniques that will be apparent to those skilled in the art (see the Examples for exemplary methods). Such methods include yeast and mammalian two-hybrid assays and co-immunoprecipitation techniques.

Other biological activities associated with DOT1L such as H3-K79 HMTase and leukemogenic activity can also be evaluated using standard methods known in the art, for example, as described in the Examples below.

The screening methods of the invention can be carried out in a cell-based or cell-free system. As a further alternative, the assay can be performed in a whole animal (including transgenic non-human animals). Further, with respect to cell-based systems, the DOT1L polypeptide (or any other polypeptide used in the assay) can be added directly to the cell or can be produced from a nucleic acid in the cell. The nucleic acid can be endogenous to the cell or can be foreign (e.g., a genetically modified cell).

Any compound of interest can be screened according to the present invention. Suitable test compounds include small organic compounds (i.e., non-oligomers), oligomers or combinations thereof, and inorganic molecules. Suitable organic molecules can include but are not limited to polypeptides (including enzymes, antibodies and Fab' fragments), carbohydrates, lipids, coenzymes, and nucleic acid molecules (including DNA, RNA and chimerics and analogs thereof) and nucleotides and nucleotide analogs. In particular embodiments, the compound is an antisense nucleic acid, an siRNA or a ribozyme that inhibits production of DOT1L polypeptide.

Small organic compounds (or "non-oligomers") include a wide variety of organic molecules, such as heterocyclics, aromatics, alicyclics, aliphatics and combinations thereof, comprising steroids, antibiotics, enzyme inhibitors, ligands, hormones, drugs, alkaloids, opioids, terpenes, porphyrins, toxins, catalysts, as well as combinations thereof.

Oligomers include oligopeptides, oligonucleotides, oligosaccharides, polylipids, polyesters, polyamides, polyurethanes, polyureas, polyethers, and poly (phosphorus derivatives), e.g. phosphates, phosphonates, phosphoramides, phosphonamides, phosphites, phosphinamides, etc., poly (sulfur derivatives) e.g., sulfones, sulfonates, sulfites, sulfonamides, sulfenamides, etc., where for the phosphorous and sulfur derivatives the indicated heteroatom for the most part will be bonded to C, H, N, O or S, and combinations thereof. Such oligomers may be obtained from combinatorial libraries in accordance with known techniques.

Further, the methods of the invention can be practiced to screen a compound library, e.g., a combinatorial chemical compound library (e.g., benzodiazepine libraries as described in U.S. Pat. No. 5,288,514; phosphonate ester libraries as described in U.S. Pat. No. 5,420,328, pyrrolidine libraries as described in U.S. Pat. Nos. 5,525,735 and 5,525,734, and diketopiperazine and diketomorpholine libraries as described in U.S. Pat. No. 5,817,751), a polypeptide library, a cDNA library, a library of antisense nucleic acids, and the like, or an arrayed collection of compounds such as polypeptide and nucleic acid arrays.

The invention also encompasses compounds identified by the screening methods described above.

As still a further aspect, the invention encompasses diagnostic methods for leukemia and/or prognostic methods for predicting the future course of leukemia in a subject by assessing H3-K79 histone methylation, wherein an elevation in H3-K79 methylation as compared with a normal (e.g., non-leukemic) subject is diagnostic of leukemia and/or prognostic of the course of the disease. In particular embodiments, the pattern of histone H3 methylation is assessed, e.g., the level of H3-K79 methylation and the level of H3-K4 methylation are determined (e.g., at a particular location of the HoxA9 gene), wherein an elevation in H3-K79 methylation and/or a reduction in H3-K4 methylation as compared with a normal (e.g., non-leukemic) subject is diagnostic of leukemia and/or prognostic of the course of the disease. This embodiment of the invention can be practiced with any mammalian subject including but not limited to human, non-human primate, cattle, sheep, goat, cat, dog, pig, horse, rat, mouse, rabbit or guinea pig subjects. In particular embodiments, the subject has or is believed to be at risk of developing leukemia. In other embodiments, the subject is an animal model of leukemia.

A "diagnostic method", as used herein, refers to a screening procedure that is carried out to identify those subjects that are affected with a particular disorder.

A "prognostic method" refers to a method used to help predict, at least in part, the course of a disease (e.g., more aggressive or less aggressive). Alternatively stated, a prognostic method may be used to assess the severity of the disease. For example, the screening procedure disclosed herein may be carried out to both identify an affected individual, to evaluate the severity of the disease, and/or to predict the future course of the disease. Such methods may be useful in evaluating the necessity for therapeutic treatment, what type of treatment to implement, and the like. In addition, a prognostic method may be carried out on a subject previously diagnosed with a particular disorder when it is desired to gain greater insight into how the disease will progress for that particular subject (e.g., the likelihood that a particular patient will respond favorably to a particular drug treatment, or when it is desired to classify or separate patients into distinct and different sub-populations for the purpose of conducting a clinical trial thereon).

It will be appreciated by those skilled in the art that the diagnostic and prognostic methods of the invention may not be conclusive and may need to be supplemented with other diagnostic and/or prognostic methods to make a final diagnosis or prognosis.

One exemplary method of diagnosing whether a subject has or is at risk for developing leukemia and/or determining the prognosis for the course of the disease comprises: obtaining a biological sample comprising nucleosomes from a subject; detecting the level of H3-K79 methylation in the biological sample; wherein an elevation in H3-K79 methylation in the biological sample as compared with the level of H3-K79 methylation in a non-leukemic biological sample is diagnostic that the subject has or is at risk of developing leukemia and/or prognostic of the course of the disease in the subject. The method can optionally further include determination of the level of H3-K4 methylation, wherein a decrease in H3-K4 methylation in the biological sample as compared with a non-leukemic sample is diagnostic that the subject has or is at risk of developing leukemia and/or prognostic of the course of the disease in the subject.

According to another representative embodiment, the invention provides a method of diagnosing whether a subject has or is at risk for developing leukemia and/or determining the prognosis for the course of the disease, the method comprising: obtaining a biological sample comprising nucleosomes from a subject; detecting the level of H3-K79 methylation associated with one or more HoxA genes (e.g., the HoxA9 gene) in the biological sample; wherein an elevation in HoxA gene-associated H3-K79 methylation (e.g., associated with the HoxA9 gene) in the biological sample as compared with the level in a non-leukemic biological sample is diagnostic that the subject has or is at risk of developing leukemia and/or prognostic of the course of the disease in the subject. The method can optionally further include determination of the level of H3-K4 methylation associated with one or more HoxA genes (e.g., the HoxA9 gene), wherein a decrease in HoxA gene associated H3-K4 methylation in the biological sample as compared with a non-leukemic sample is diagnostic that the subject has or is at risk of developing leukemia and/or prognostic of the course of the disease in the subject.

In exemplary embodiments, an "elevation" or "increase" (or similar terms) in methylation (e.g., H3-K79 methylation) is at least about a 25%, 50%, 75%, 2-fold, 3-fold, 5-fold, 10-fold, 15-fold, 20-fold or more increase in methylation as compared with the level of methylation in a non-leukemic biological sample.

In other representative embodiments, a "decrease" or "reduction" (or similar terms) in methylation (e.g., H3-K4 methylation) is at least about a 25%, 40%, 50%, 60%, 75%, 80%, 85%, 90%, 95%, 98% or more decrease in methylation as compared with the level of methylation in a non-leukemic biological sample. In particular embodiments, no methylation is detectable.

Any suitable biological sample can be used including cell or tissue samples, umbilical cord samples, blood, plasma or serum samples, urine or fecal samples, mucus or sputum samples, and the like. In particular embodiments, the biological sample is a B cell or bone marrow sample. In other representative embodiments, the biological sample is a histone or nucleosome preparation comprising histone H3 (e.g., obtained from B cells or bone marrow cells). In representative embodiments, cells or tissue are removed from a subject, cultured and nucleosomes prepared from the cultured cells or tissue.

By "non-leukemic biological sample" it is meant a suitable control sample that is indicative of a normal subject (i.e., not having or at risk for developing leukemia). For example, the sample can be isolated from a normal subject or, in some instances (e.g., a nucleosome preparation), can be isolated from cultured cells.

As further uses of the present invention, the DOT1L nucleic acids and polypeptides can be used in methods of methylating histones (H3) in a cell free system, in cultured cells or in vivo. In particular embodiments, the substrate is a histone substrate comprising H3. In other embodiments, the substrate is a nucleosome substrate comprising H3. Other uses of the DOT1L nucleic acids and DOT1L polypeptides as well as antisense and siRNA molecules that inhibit DOT1L polypeptide production include modulation of telomeric silencing, regulation of gene expression and/or cell cycle regulation.

Having described the present invention, the same will be explained in greater detail in the following examples, which are included herein for illustration purposes only, and which are not intended to be limiting to the invention.

EXAMPLE 1

Experimental Procedures

HMTase-Mediated Methylation of H3-Lysine 79

Antibodies, hDOT1L Constructs and Protein Preparation. The methyl-K79-specific antibody was raised by injection of rabbits with a synthetic peptide coding for amino acids 73-83 of histone H3 with K79 di-methylated (Ile-Ala-Gln-Asp-Phe-mLys-Thr-Asp-Leu-Arg-Phe; SEQ ID NO:4). The methyl-K4, -K9 antibodies were purchased from Upstate Biotechnology (Lake Placid, N.Y.). The full-length hDOT1L was derived from two over-lapping EST clones BF507396 and BF982417. The FLAG®-tagged constructs were cloned into the EcoRI/XhoI sites of a pcDNA-derived vector by PCR. The GST-fusion of the hDOT1L N-terminal fragments were also cloned into the EcoRI/XhoI sites of pGEX-KG vector by PCR. The mutants were generated through PCR-based mutagenesis. All PCR-generated constructs were verified by sequence analysis. The GST-hDOT1L fusion proteins were purified as according to standard methods (Wang, et al. (2001) *Mol. Cell* 8:1207-1217). The recombinant proteins were then cleaved using thrombin following manufacturer's instructions. Proteins were quantified by COOMASSIE® staining.

Cell Synchronization, Labeling and Flow Cytometry. To obtain cells synchronized at the G1/S boundary, HeLa cells were treated with 2 mM thymidine (SIGMA, St. Louis, Mo.) for 18 hours, followed by a 9 hour release in thymidine-free medium, and then treated again with 2 mM thymidine for 17 hours to arrest cells at the beginning of S phase. The synchronized cells were released in fresh medium and harvested every two hours. HeLa cells synchronized at the mitotic stage were prepared by blocking with 2 mM thymidine for 18 hours, releasing for 3 hours, and then incubating with 100 ng/mL nocodazole for 12 hours. The cells were then washed three times with phosphate-buffered saline (PBS) to eliminate nocodazole before release into fresh medium. Cells were harvested every two hours and cell lysates and histones were prepared using well-established methods (Wang, et al. (2001) *Science* 293:853-857). The cell cycle position of the cells collected at different stages was determined by propidium iodide (PI) staining. For simultaneous measurement of DNA content and levels of specific proteins (Mi2 and mK79), asynchronized HeLa cells were fixed by ice-cold ethanol before treatment with 0.25% TRITON® in PBS for 5 minutes. Subsequently, the cells were labeled with anti-Mi2 or anti-mK79 antibodies followed by fluorescein isothiocyanate (FITC)-conjugated goat anti-rabbit secondary antibody (Jackson ImmunoResearch Laboratories, West Grove, Pa.). The cells were labeled with PI before performing flow cytometry analysis using stand methods.

EXAMPLE 2

Results

HMTase-Mediated Methylation of H3-Lysine 79

Identification of H3-K79 as a Novel Methylation Site. Histone methylation has emerged as an important player in regulating gene expression and chromatin function (Jenuwein and Allis (2001) *Science* 293:1074-1080; Zhang and Reinberg (2001) *Genes Dev.* 15:2343-2360; Kouzarides (2002) *Curr. Opin. Genet. Dev.* 12:198-209). Histone methylation occurs on arginine and lysine residues at the N-terminal tails of histones H3 and H4, and is catalyzed by two distinct family of proteins, the PRMT1 and the SET-domain-containing family of proteins (Zhang and Reinberg (2001) *Genes Dev.* 15:2343-2360). Since the discovery of the first histone lysine methyltransferase (Rea, et al. (2000) *Nature* 406:593-599), other lysine methyltransferases that methylate histone H3 at lysines 4, 9, 27, and 36 have been reported (Briggs, et al. (2001) *Genes Dev.* 15:3286-3295; Roguev, et al. (2001) *EMBO J.* 20:7137-7148; Wang, et al. (2001) *Mol. Cell* 8:1207-1217; Tachibana, et al. (2001) *J. Biol. Chem.* 276:25309-25317; Yang, et al. (2002) *Oncogene* 21:148-152; Nagy, et al. (2002) *Proc. Natl. Acad. Sci. USA* 99:90-94; Bryk, et al. (2002) *Curr. Biol.* 12:165-170; Nishioka, et al. (2002) *Genes Dev.* 16:479-489; Strahl, et al. (2002) *Mol. Cell Biol.* 22:1298-1306). One common feature of these histone lysine methyltransferases is that they all contain a SET domain that is required for their enzymatic activity. Thus, SET domain is believed to be a signature motif for histone lysine methyltransferase (Zhang and Reinberg (2001) *Genes Dev.* 15:2343-2360).

Methylation sites are known to be located at the N-terminus of histones H3 and H4 (Jenuwein and Allis (2001) *Science* 293:1074-1080; Zhang and Reinberg (2001) *Genes Dev.* 15:2343-2360). Mass spectrometry analysis has been used to identify potential novel modification sites in the histone globular domain (Feng et al., (2002) *Current Biology* 12:1052-1058; the disclosure of which is incorporated by reference herein it its entirety). These investigations demonstrated that histone H3 from HeLa cells is mono-methylated on K79 (Feng, et al., Id at FIG. 1A, panels a-c).

Figure 1A:
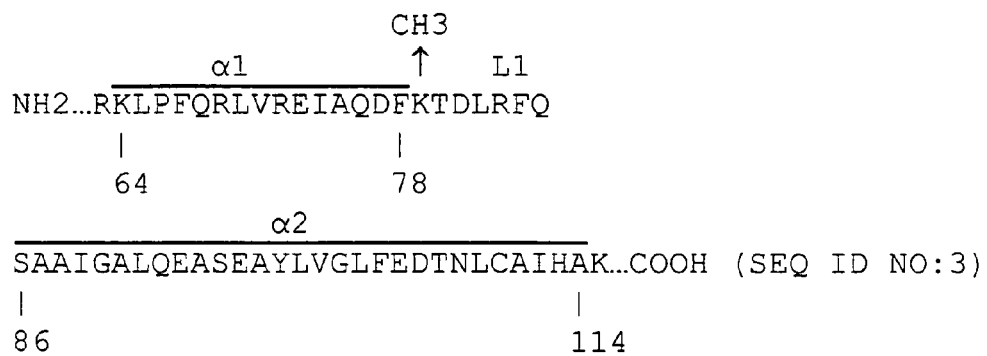
FIGS. 1A-1C show that H3-K79 methylation is conserved from yeast to human. (A) Location of K79 of histone H3 relative to the two α-helices (α1 and α2) and loop 1 (L1) (SEQ ID NO:3) based on the known nucleosome structure (Luger, et al. (1997) *Nature* 389:251-260). (B) Characterization of the H3-mK79 antibody. HeLa core histones, recombinant histone H3 that are not methylated, methylated by SET7 or SUV39 were analyzed by COOMASSIE® staining and western blot analysis using the mK4-, mK9-, and mK79-specific antibodies. The mK79-specific antibody was raised against an H3 peptide containing di-methylated K79 (Ile-Ala-Gln-Asp-Phe-$^m$Lys-Thr-Asp-Leu-Arg-Phe; SEQ ID NO:4). (C) H3-K79 methylation occurs in a wide range of organisms.

Based on the well-established nucleosome structure (Luger, et al. (1997) *Nature* 389:251-260), K79 is located in a loop connecting the first and the second alpha helixes (FIG. 1A). This region is exposed and is adjacent to the interface between H3/H4 tetramer and the H2A/H2B dimer. Although K79 is not directly involved in the formation of the interface, it is in a position capable of influencing the access to the interface, indicating that methylation on K79 may play an important role in regulating the access of protein factors to chromatin.

Figure 1B:
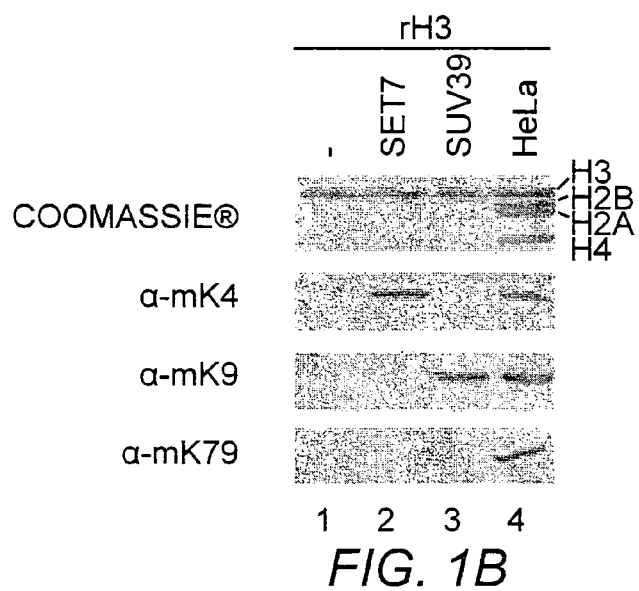

H3-K79 Methylation is Conserved from Yeast to Human. To confirm the MS data and the conservation of K79 methylation in other organisms, we generated a polyclonal antibody against a dimethyl-K79 H3 peptide Ile-Ala-Gln-Asp-Phe-$^m$Lys-Thr-Asp-Leu-Arg-Phe (SEQ ID NO:4). To examine the specificity of the antibody, recombinant histone H3 that was either not methylated, or methylated on K4 or K9 by SET7 (Wang, et al. (2001) *Mol. Cell* 8:1207-1217) or SUV39H1 (Rea, et al. (2000) *Nature* 406:593-599), respectively, were subjected to COOMASSIE® staining and western blot analysis. As a positive control, equivalent amounts of core histones purified from HeLa cells were also analyzed. Results shown in FIG. 1B demonstrate that while the antibody recognized histone H3 purified from HeLa cells, it did not recognize unmethylated, or K4-, or K9-methylated H3 (FIG. 1B, lower panel). In addition, competition with two peptides of identical amino acid sequences with or without di-methylation on K79 demonstrate that only the methylated peptide is capable of abolishing the reactivity of the antibody toward the HeLa histone H3. Thus, it was concluded that the antibody is H3-mK79-specific.

Figure 1C:
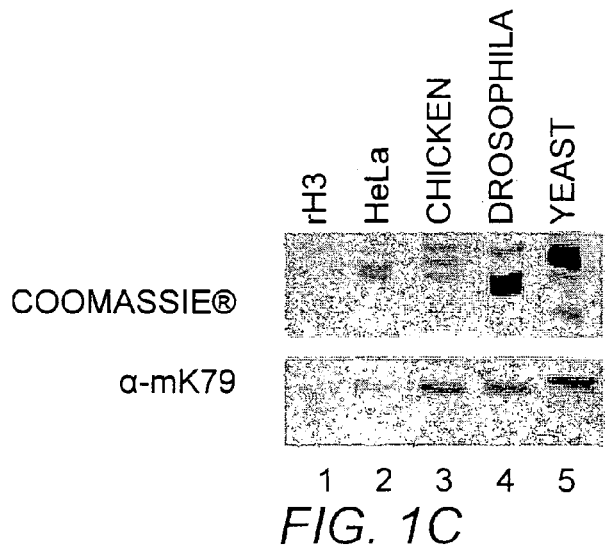

The fact that K79 and adjacent sequences of H3 are conserved in different organisms prompted us to test the possibility of H3-K79 methylation occurs in other organisms. Thus, core histones isolated from chicken, *Drosophila*, and budding yeast were analyzed by western blotting using the H3-mK79-specific antibody. As negative and positive controls, recombinant H3 and HeLa core histones were included in the assay. Results shown in FIG. 1C demonstrate that H3-K79 methylation occurs in all the organisms analyzed. Thus, it was concluded that H3-K79 methylation is conserved from yeast to human.

Human DOT1-Like Protein is an H3-K79-Specific Methyltransferase. Having demonstrated that H3-K79 methylation occurs in yeast, we identified the responsible enzyme in this organism. It was reasoned that deletion of the K79 HMTase should lead to loss or reduction of K79 methylation that could be detected by western blot analysis using the mK79-specific antibody described above. The candidate genes that we screened included the six yeast SET domain-containing proteins (Set 1 to Set 6; a gift from Kevin Struhl and Huck Hui Ng, Harvard Medical School) as well as those that were predicted to encode SAM-binding domain-containing proteins (Niewmierzycka and Clarke (1999) *J. Biol. Chem.* 274: 814-824; Dlakic (2001) *Trends Biochem. Sci.* 26:405-407). This screen resulted in the identification of DOT1 as the HMTase responsible for K79 methylation in yeast (Ng, et al. (2002) *Genes Dev.* 16:1518-27).

Dot1 was originally identified in a genetic screen for genes whose overexpression disrupts telomeric silencing (Singer, et al. (1998) *Genetics* 150:613-632). Disruption or overexpression of Dot1 not only impaired telomeric silencing, but also reduced silencing at mating type and rDNA loci (Singer, et al. (1998) *Genetics* 150:613-632). In addition to participating in silencing, DOT1 also plays an important role in meiotic checkpoint control (San-Segundo and Roeder (2000) *Mol. Biol. Cell* 11:3601-3615). Given that K79 methylation was conserved from yeast to human (FIG. 1C), we expected that DOT1-like (DOT1L) proteins existed in other organisms. A BLAST search revealed several putative proteins with significant sequence homology to DOT1. Sequence alignment of these proteins revealed several conserved blocks (FIG. 2A) that were predicted to be involved in SAM binding (Dlakic (2001) *Trends Biochem. Sci.* 26:405-407). The BLAST search also revealed that a hypothetical human protein (GEN-BANK accession number AAC08316) encoded by a gene located on 19p13.3 is likely the human DOT1L. However, this hypothetical protein was incomplete at both 5' and 3' ends. To clone the full-length cDNA encoding hDOT1L, several EST clones were obtained and sequenced. Two overlapping EST clones (BF507396 and BF982417) contained a single open reading frame (ORF) which was predicted to encode a 1537 amino acid protein with a calculated mass of 165 kDa (FIG. 2B). The fact that the nucleotide sequence (FIG. 2C-E) around the first methionine conformed to the Kozak initiator sequence in combination with the fact that the cDNA contained an upstream stop codon indicated that the 1537 amino acids encoded by the cDNA represented the full-length protein. Analysis of the hDOT1L protein sequences revealed no known functional motif other than a putative SAM-binding domain (FIG. 2B).

To determine whether hDOT1L possessed intrinsic HMTase activity, two recombinant proteins corresponding to the N-terminal 351 and 472 amino acids of hDOT1L, respectively, were produced in *E. coli*. The N-terminus of hDOT1L was selected because this region contained the putative SAM-binding motif and was most conserved among the different DOT1L proteins (FIG. 2A). HMTase assays revealed neither protein possessed significant enzymatic activity when free core histones were used as a substrate (FIG. 3A, lanes 1-3). However, when nucleosomes were used as a substrate, hDOT1L(1-472) exhibited significant HMTase activity while hDOT1L(1-351) was inactive (FIG. 3A, lanes 4 and 5). To demonstrate that the HMTase activity depended on binding to SAM, we generated a mutated version of hDOT1L(1-472) [hDOT1L(1-472)m] by changing the highly conserved Gly-Ser-Gly$_{163-165}$ sequence of motif I (FIG. 2A) to Arg-Cys-Arg. This mutation completely abolished the HMTase activity (FIG. 3A, compare lanes 5 and 6). Taken together, these results demonstrate that hDOT1L is a nucleosomal H3-specific HMTase and that both the SAM binding motif and the sequences between amino acids 351 and 472 are critical for enzymatic activity.

Having demonstrated the HMTase activity of human DOT1L in vitro, we demonstrated its HMTase activity in vivo. Accordingly, mammalian expression vectors encoding a FLAG®-tagged hDOT1L and a motif I mutant were transfected into 293T cells. Core histones purified from the transfected cells were analyzed by COOMASSIE® and western blot analysis using antibodies specific for methylated K4, K9 or K79. Results shown in FIG. 3B demonstrate that overexpression of hDOT1L significantly increased H3-K79 methylation while having no effect on K4 and K9 methylation (compare lanes 1 and 2). Increased K79 methylation was dependent on an intact motif I as transfection of a motif I mutant did not affect K79 methylation (FIG. 3B, compare lanes 1 and 3). This differential effect was not caused by differential expression since both constructs expressed hDOT1L at a similar level (FIG. 3B, lower two panels). Based on these results, we concluded that hDOT1L is an H3-K79-specific HMTase in vivo.

Figure 4A:
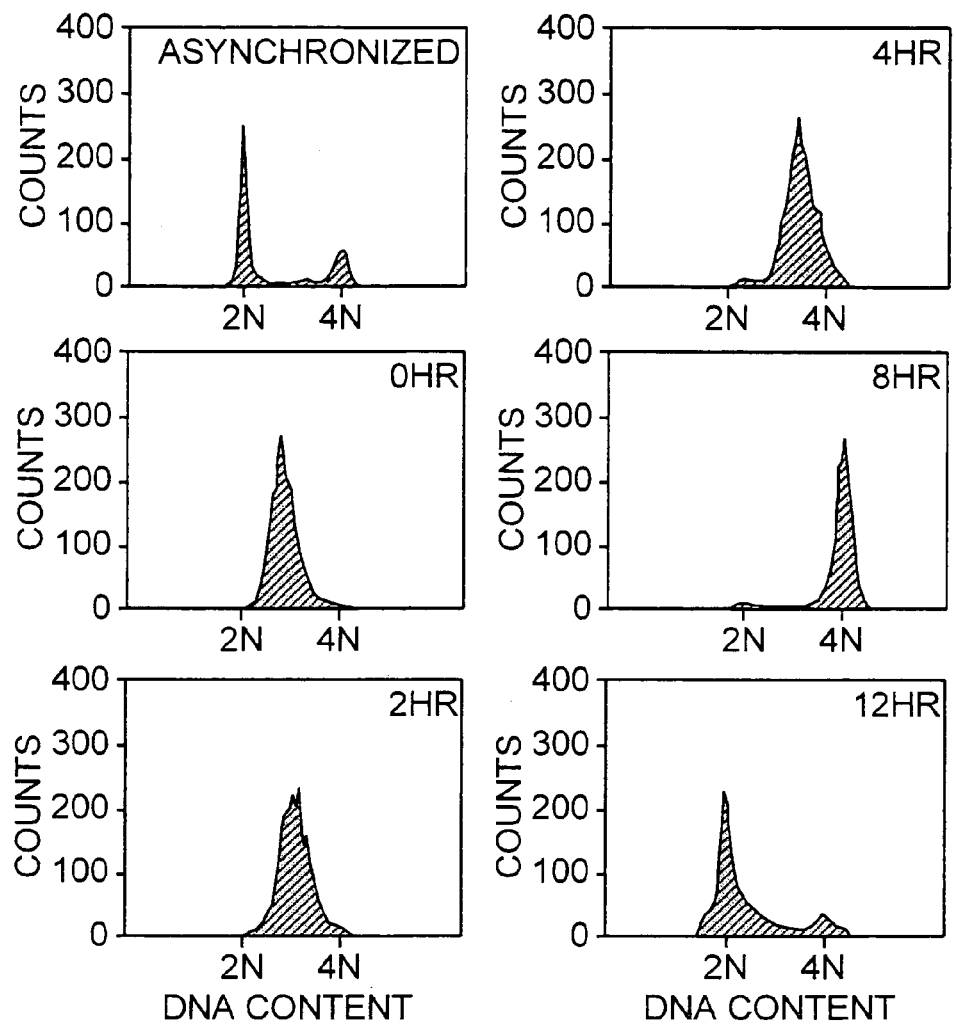
Figure 4B:
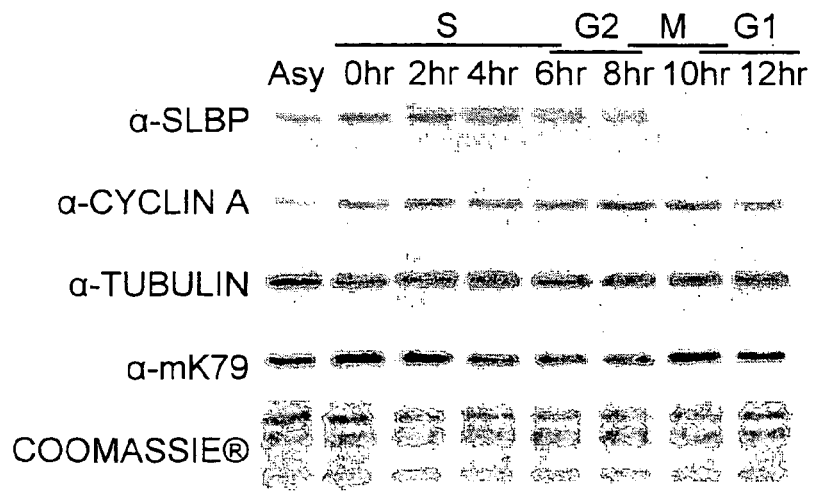

Methylation on K79 is Regulated During the Cell Cycle. Total histone methylation level is regulated during the cell cycle (Borun, et al. (1972) *J. Biol. Chem.* 247:4288-4298). Thus, it was determined whether the level of K79 methylation changed during the cell cycle. To obtain a population of synchronous cells, we arrested HeLa cells at the G1/S border using a double thymidine block. After releasing the arrested cells from the thymidine block, cells were collected every two hours for flow cytometry analysis as well as for the preparation of protein extracts and histones. Flow cytometry analysis (FIG. 4A) indicated that more than 95% of the cells progress through S phase and enter G2 synchronously. The cells were successfully arrested at the G1/S border before release as evidenced by the accumulation of the histone mRNA stem-loop-binding-protein (SLBP) (FIG. 4B). As has been demonstrated (Whiffield, et al. (2000) *Mol. Cell Biol.* 20:4188-4198), SLBP levels stayed high throughout S phase and dropped rapidly as cells exited S phase (FIG. 4B). The cells completed mitosis about 12 hours after release, as evidenced by the degradation of cyclin A when cells entered anaphase (FIG. 4B). To determine whether the level of K79 methylation changed during the cell cycle, histones isolated from corresponding cells were subjected to western blot analysis using the mK79-specific antibody. This analysis demonstrated that the level of K79 methylation decreased during S-phase and reached the lowest level in G2 and increased during M-phase (FIG. 4B).

Figure 4C:
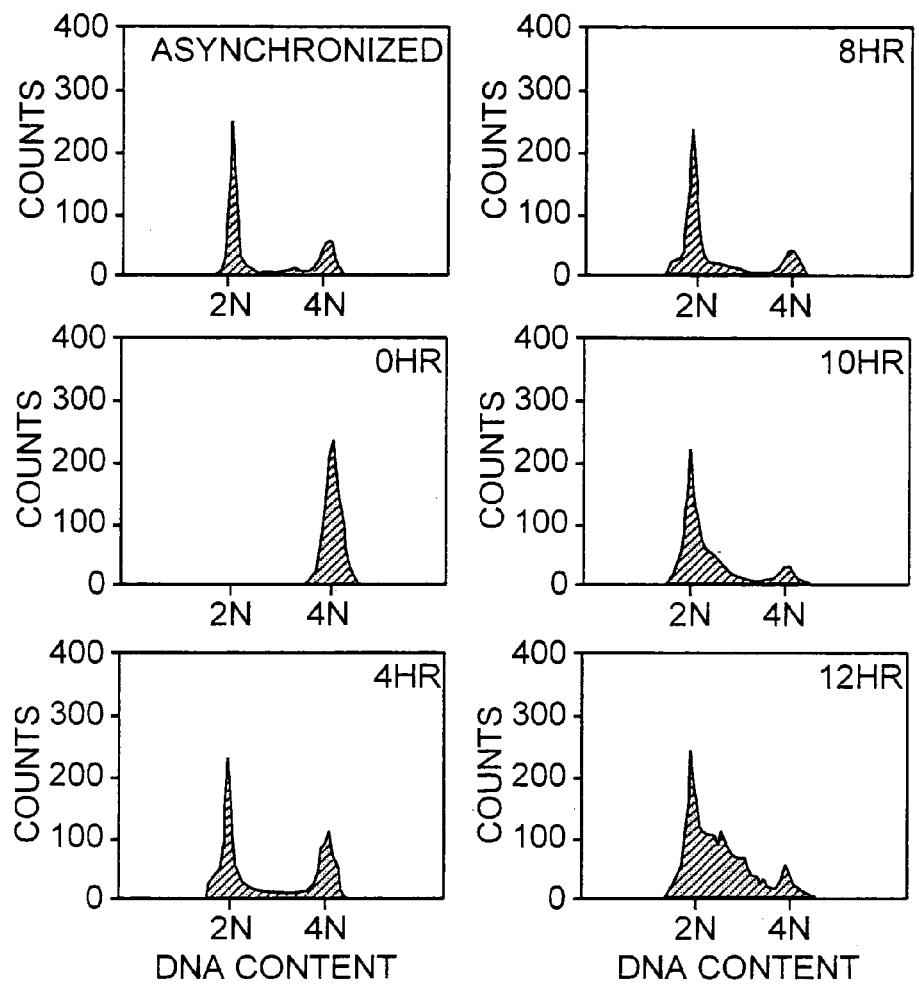
Figure 4D:
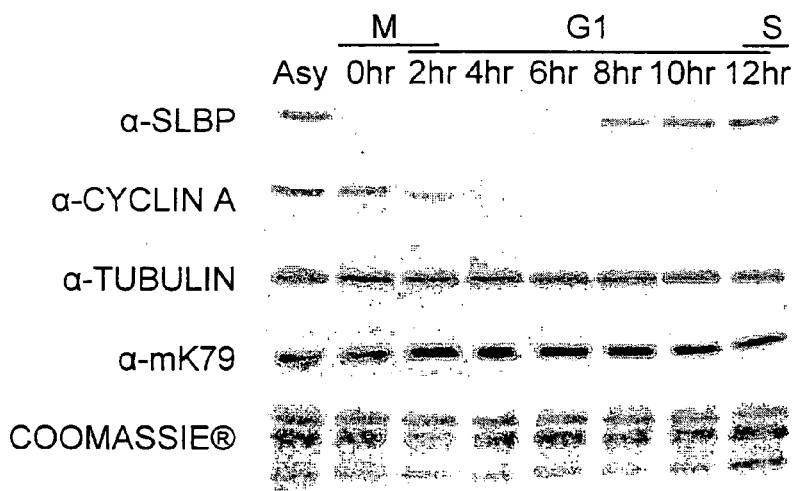

To analyze K79 methylation status in G1 phase, we arrested the cells with thymidine, released them, and then arrested them in mitosis with nocodazole. After release from the nocodazole block, the cells progressed through G1 to S phase synchronously (FIG. 4C). The cells completed mitosis 2 hours after release from the nocodazole block as evidenced by the degradation of cyclin A (FIG. 4D). The cells then started to enter S phase about 10 hours after release as evidenced by the accumulation of SLBP (FIG. 4D). Western blot analysis of the histones from cells collected at different time points after the nocodazole release indicated that the K79 methylation remained at a high level throughout the G1-phase (FIG. 4D).

Figure 4E:
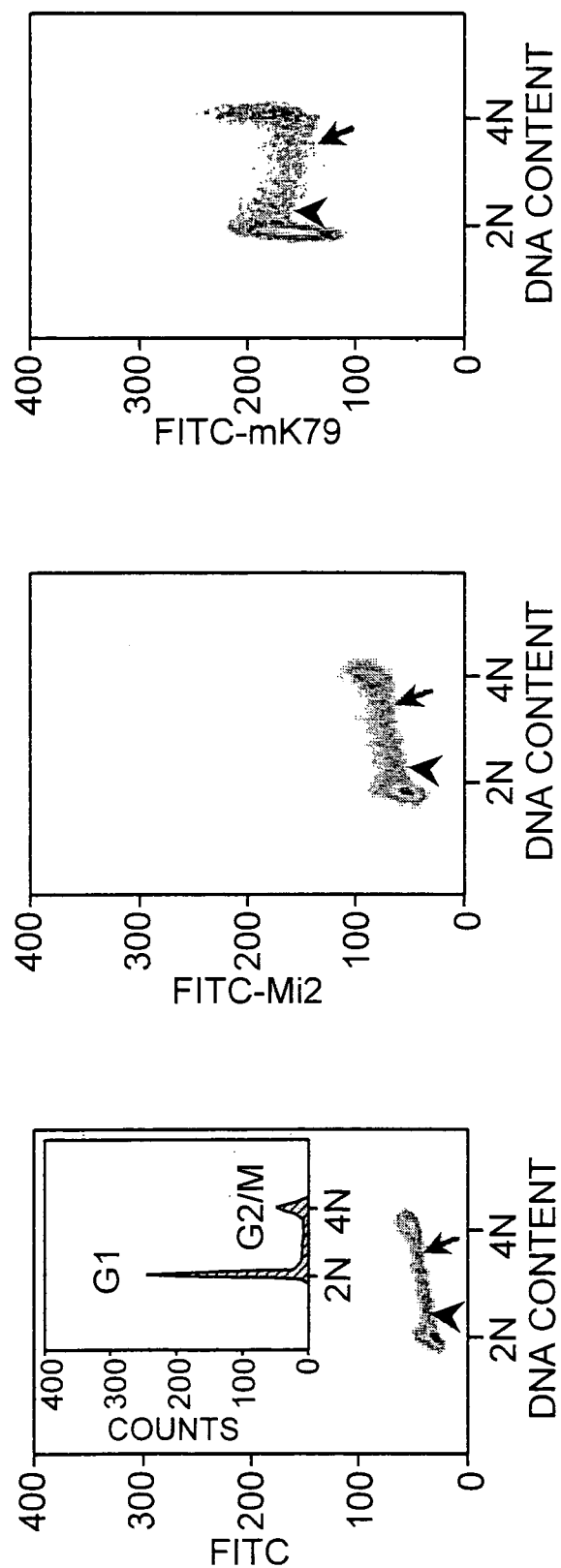

To further confirm the cell cycle-dependent changes in K79 methylation, we performed bivariate analysis of DNA content and mK79 level using a method similar to that used in analyzing cell cycle-dependent changes of cyclins using asynchronous cells (Bonifacino, et al. (1999) Current Protocols in Cell Biology (John Wiley & Sons, Inc.). Book chapter 8. Unit 8.4; Darzynkiewicz, et al. (1999) Determining Cell Cycle Stage by Flow Cytometry (John Wiley & Sons, Inc.), 8.4.1-8.4.18). For each individual cell, DNA was labeled with propidium iodide (red), while K79-methylated-H3 was labeled with an FITC-conjugated secondary antibody (green). The intensities of green color and red color of a particular cell reflected K79 methylation level and DNA content, respectively. Negative controls without a primary antibody or with antibody against Mi-2, a component of a nucleosome remodeling and deacetylase complex (Zhang, et al. (1998) Cell 95:279-289), resulted in a slight increase in FITC signals when cells proceeded from G1-phase to G2/M phase (FIG. 4E, left and middle panels). This result was anticipated as cell size becomes bigger during this transition. However, labeling of the cells with the mK79-specific antibody resulted in a decrease in FITC-labeling when cells went through S-phase (FIG. 4E, right panel, compare early and late S phases). It is unlikely that the decrease in mK79 level during S-phase was caused by 'dilution' by nascent histones during chromatin assembly as a similar decrease was not observed in other methylation sites. By using two different methods, we demonstrated that the level of K79 methylation decreased during S-phase, reached its lowest level in G2, increased during M-phase, and was maintained at a high level during G1-phase.

EXAMPLE 3

Experimental Procedures

Structure of the Catalytic Domain of Human DOT1L

Protein Methods. To produce recombinant hDOT1L fragments containing the N-terminal 351, 370, 375, 385, 416, 452, and 472 amino acids in *E. coli*, corresponding cDNA fragments were amplified by PCR and cloned into a pGEX-KG vector (between EcoRI-XhoI sites). The presence of correct inserts was verified by DNA sequencing. The plasmid expressing the first 416 residues of hDOT1L, pGEX-KG/hDOT1L(1-416), was used for subsequent Δ(376-390) and Δ(390-407) deletions and N241D, N241A, Y312F and Y312A point mutations. The deletion and point mutations were carried out by PCR and confirmed by sequencing. GST-hDOT1L fusion proteins and mutants were first purified on a glutathione-SEPHAROSE® column. The GST-tag was then removed by thrombin digestion in the column. The eluted proteins were further purified on HITRAP™-SP and SUPERDEX™-75 columns (Amersham Pharmacia Biotech, Piscataway, N.J.).

Histone Methyltransferase Assay. Histone methyltransferase assay was performed using established methods (Wang, et al. (2001) *Science* 293:853-857). Oligo-nucleosomes purified from HeLa cells or chicken blood cells were quantified and equal concentrations were used in each assay. Briefly, recombinant hDOT1L proteins (0.75 μM) were incubated with oligo-nucleosomes (1.5 μM) in reactions containing 20 mM Tris-HCl (pH 8.0), 4 mM EDTA, 1 mM PMSF, 0.5 mM DTT, and 0.5 μL $^3$H-SAM (15 Ci/mM; NEN™ Life Science Products) for 1 hour at 30° C. For peptide competition, 1.5 μM, 15 μM, or 150 μM of positively charged C-RS10 peptide (Cys-Arg-Ser-Arg-Ser-Arg-Ser-Arg-Ser-Arg-Ser-Arg-Ser-Arg-Ser-Arg-Ser-Arg-Ser; SEQ ID NO:20) were added to reactions. Reactions were stopped by addition of 7 μL of 5×SDS loading buffer and proteins were separated in an 18% SDS-PAGE. Following stain and destain of COMMASSIE® Blue, gels were treated with Rapid Autoradiography Enhancer (NEN™ Life Science Products, Boston Mass.) for 40 minutes, dried, and exposed to X-ray films. For quantitation, gel slices were excised and counted with scintillation counting. Two independent experiments were performed at the same time and average $^3$H (CPM) values were used in the figures.

Gel Shift Assay. Different amount of recombinant hDOT1L proteins were incubated with HeLa mono-nucleosomes (1.5 μM) under the same conditions as those in the histone methyltransferase assay, except that SAM is omitted. Following incubation for 1 hour at 30° C., samples were resolved in a 1.8% agarose gel and visualized under UV by ethidium bromide staining.

EXAMPLE 4

Results

Structure of the Catalytic Domain of Human DOT1L

Disordered C-terminal Region is Important for Enzyme Activity and Nucleosome Binding. The full-length hDOT1L consists of 1537 amino acids (Example 2) but only the N-terminal ~360 amino acids share significant sequence similarity with yeast Dot1 (FIG. 2A). We determined that amino acids 1-416 of hDOT1L, hDOT1L(1-416), contain the active HMTase catalytic domain (FIG. 5).

The crystal structure of hDOT1L(1-416) complexed with SAM has been solved to 2.5 Å resolution using multiwavelength anomalous diffraction (MAD) of SeMet protein crystals (Min, et al. (2003) *Cell* 112:711-723; the disclosure of which is incorporated herein by reference). Atomic coordinates for the hDOT1L(1-416) structure have been deposited in the RCSB database under ID code 1NW3). Amino acids C-terminal to αK (amino acids 333-416) are disordered in the crystal structure. As disclosed above, we demonstrated that certain amino acids located between residue 351 and 416 were important for the enzymatic activity of hDOT1L, as hDOT1L(1-416) could methylate oligo-nucleosomes efficiently but hDot1(1-351) could not under the same conditions (FIG. 5). Since the C-terminal end of hDOT1L(1-416) was spatially distant from the SAM binding site and because access to the active site was rather restricted (Min, et al. (2003) *Cell* 112:711-723), the C-terminus might be important in substrate binding rather than having a direct involvement in catalysis. Accordingly, we tested the enzymatic activity (FIG.

6A) and nucleosome binding capability (FIG. 6B) of a series of hDOT1L variants truncated at the disordered C-terminal region.

Figure 6A:
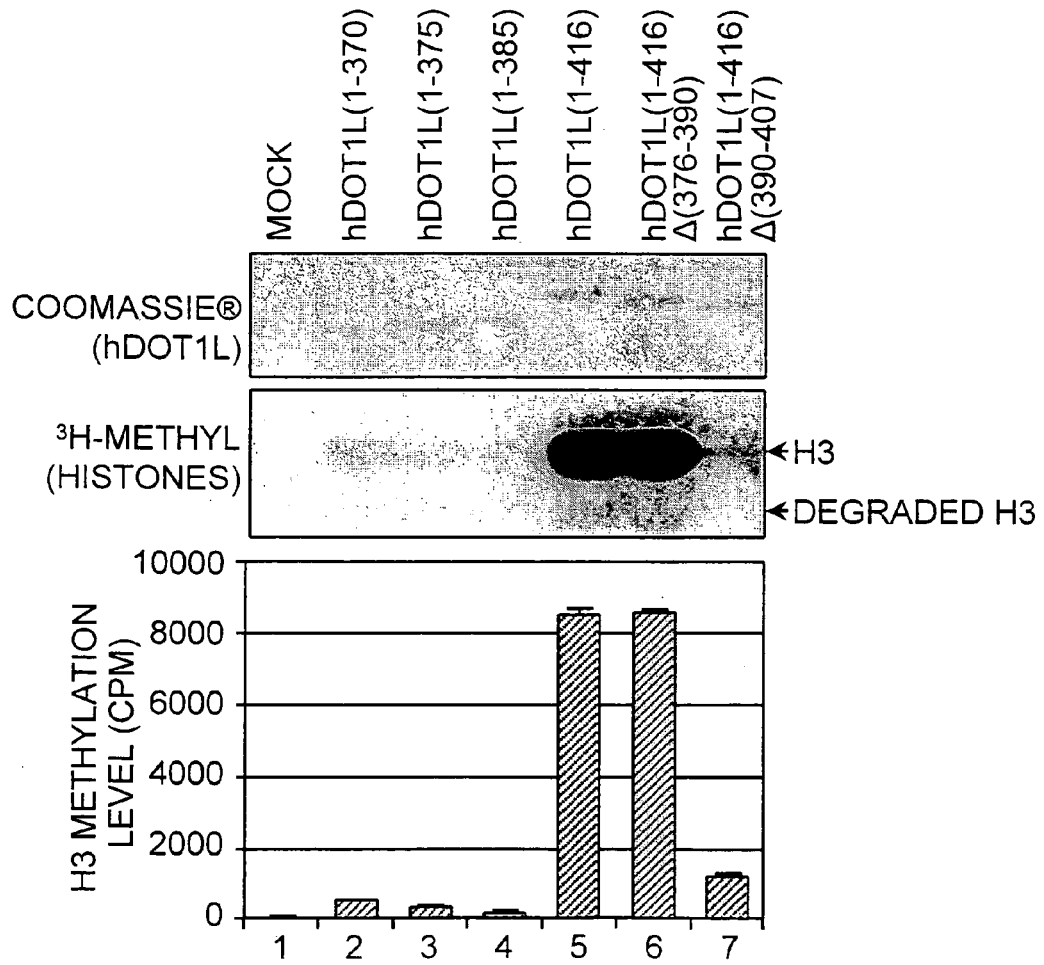

To identify the elements within the region between amino acids 351 and 416 that were critical for the HTMase activity of hDOT1L, we added back 19, 24 and 34 amino acids to the C-terminus of hDOT1L(1-351), termed hDOT1L(1-370), hDOT1L(1-375) and hDOT1L(1-385), respectively, to determine whether the HMTase activity of hDOT1L could be restored. FIG. 6A (lanes 2, 3 and 4) shows that all three constructs failed to restore the HMTase activity to a level comparable to that of hDOT1L(1-416). We then fused the last 26 amino acids of hDOT1L(1-416) to the inactive hDOT1L(1-375), creating an internal deletion mutant Δ(376-390). FIG. 6A (lane 6) shows that this mutant was as active as the wild-type hDOT1L(1-416), indicating that amino acids 391-416 were crucial for the HMTase activity. This region of hDOT1L is enriched with positively charged residues (FIG. 6C), and these residues may be important for the HMTase activity. Removing a stretch of amino acids containing 9 of the 15 positively charged residues in this region, Δ(390-407), significantly reduced the enzymatic activity (FIG. 6A, lane 7).

Figures 6B, 6C:
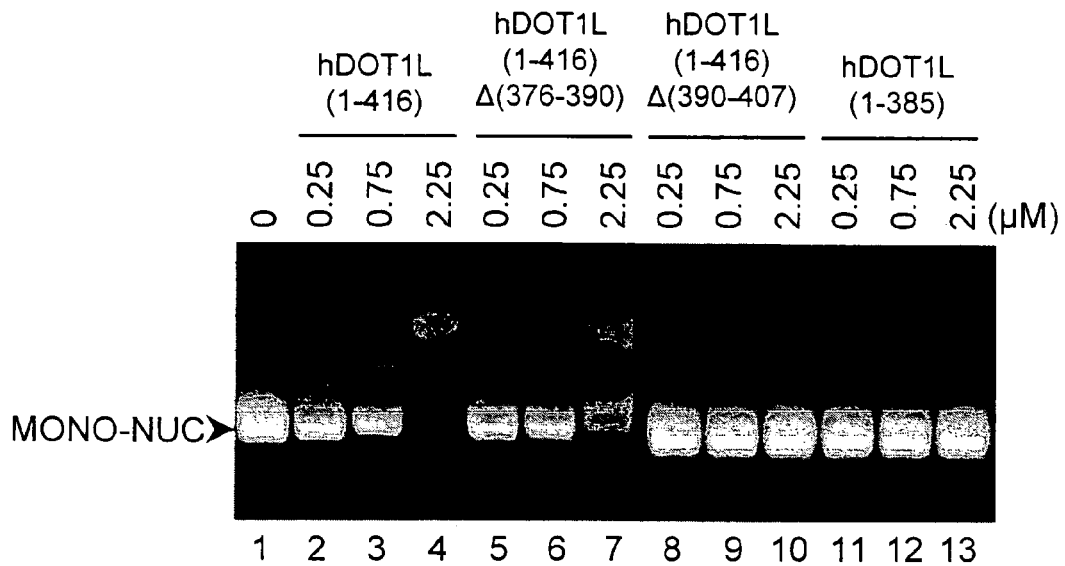
Figure 6D:
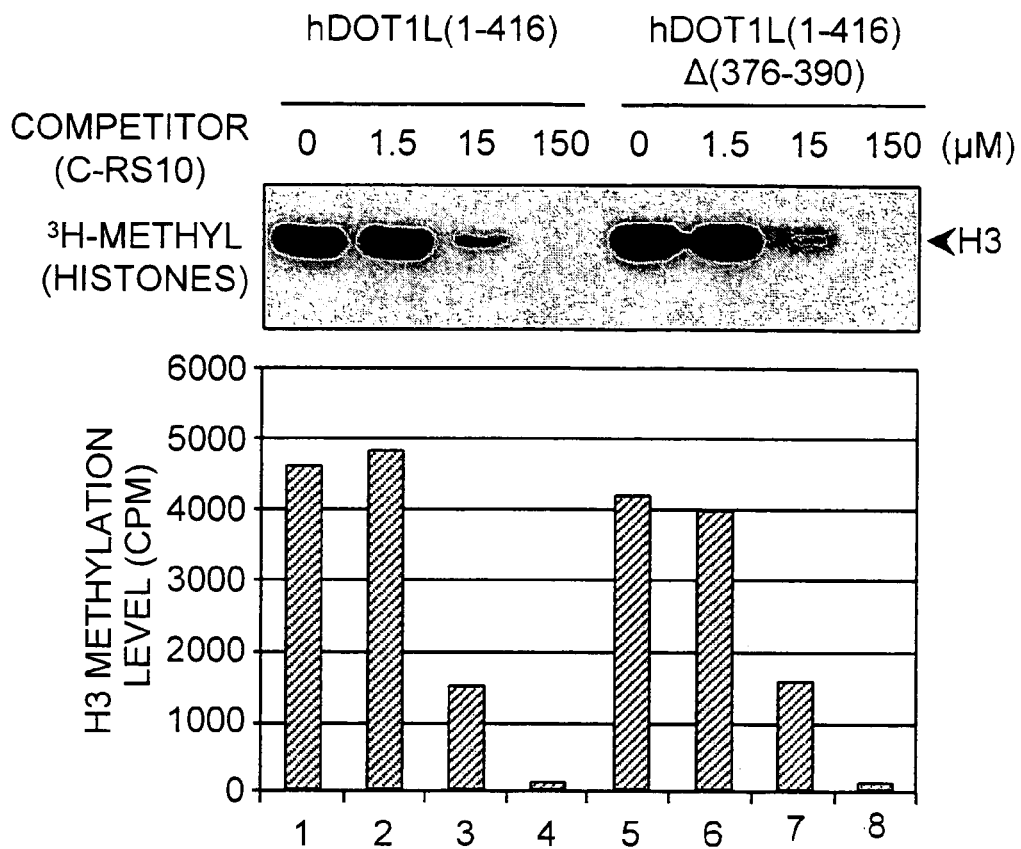

We next examined mono-nucleosome binding of hDot1(1-416) and several of its truncation variants by gel mobility shift assays (GSMA). FIG. 6B shows that enzymatically active hDOT1L(1-416) and Δ(376-390) caused slower migration of mono-nucleosomes (lanes 2-4 and 5-7), while weakly active Δ(390-407) and inactive hDOT1L(1-385) showed no detectable gel shifts within the sensitivity limit of the assay. The addition of SAM in the GSMA did not change the gel shift pattern in FIG. 6B. This observation qualitatively correlated the nucleosome binding ability with the HMTase activity of hDOT1L proteins and showed the importance of the positively charged C-terminal region in nucleosome binding. Our modeling of hDOT1L-nucleosome interaction indicated that the C-terminal region was near DNA and the disordered C-terminal positively charged region may be involved in substrate binding by interacting with the negatively charged nucleosomal DNA. Consistent with this, we could detect strong, but apparently non-sequence specific, binding of hDOT1L(1-416) with DNA extracted from mono-nucleosomes. To further probe the nature of hDOT1L-nucleosome interaction, we used a 21-residue highly charged peptide, C-RS$_{10}$, containing 10 tandem repeats of arginine and serine as a competitor in our nucleosome binding and HMTase assays. Adding the C-RS$_{10}$ peptide in GSMA prevented mono-nucleosomes from entering the gel well. The HMTase activities of hDOT1L(1-416) and Δ(376-390), shown in lanes 1-4 and 5-8 of FIG. 6D, respectively, were effectively competed with increasing concentrations of the peptide. These results clearly demonstrate the functional importance of the C-terminal charged region of hDOT1L(1-416).

EXAMPLE 5

Experimental Procedures

Characterization of hDOT1L Localization

Constructs. Full-length FLAG®-hDOT1L are described in Example 1. For FLAG®-tagged hDOT1L deletion mutants, PCR-amplified inserts were ligated to p FLAG®-beta-cDNA3 vector digested with EcoRI and XhoI. When constructing GFP-fused plasmids, all hDOT1L deletion mutants were constructed by cloning the inserts into the EcoRI and KpnI sites of pEGFP-C3 vector (CLONTECH™, Palo Alto, Calif.). For fragments larger than 20 amino acids, PCR was used to amplify the inserts. For fragments less than 20 amino acids, DNA were synthesized and annealed before ligation to the vector. For the construction of the hDOT1L-767-3xNLS construct, hDOT1 cDNA encoding amino acid 1-767 was fused with three tandem repeats of a nuclear localization signal (NLS) derived from SV40 T-antigen (Asp-Pro-Lys-Lys-Lys-Arg-Lys-Val; SEQ ID NO:21), and subcloned into pcDNA3b-FLAG® vector. All fragments amplified by PCR and all constructs involving mutagenesis were verified by sequencing.

Cell Culture, Transfection, and Immunoprecipitation. 293T or U2OS cell were maintained in Dulbecco's modified Eagle's medium (DMEM) supplemented with 10% fetal calf serum and grown at 37° C., 5% $CO_2$. Cells were transfected with QIAGEN® EFFECTENE™ Transfection Reagents Twenty-four hours after transfection, cells were harvested and washed with ice-cold phosphate-buffered saline (PBS) before being lysed with lysis buffer (50 mM Tris, 150 mM NaCl, 0.1% NP-40, 50 mM NaF, 1 mM dithiothreitol, 1 mM phenylmethylsulfonyl fluoride, 1 µg of aprotinin/mL, 0.5 µg of leupeptin/mL, and 0.7 µg of pepstatin/mL). After incubation for 30 minutes at 4° C., the cell debris was removed by centrifugation at 14,000 rpm for 5 minutes in an EPPENDORF® centrifuge (Brinkmann Instruments, Inc., Westbury, N.Y.). About 1 mg of protein extracts was incubated with 20 µL of FLAG®-M2 agarose beads (Sigma, St. Louis, Mo.) at 4° C. for 4 hours. After three washes with lysis buffer containing 300 mM salt, the immunoprecipitated proteins were analyzed by western blot.

In vivo Ubiquitination Assays. pcDNA3b-FLAG®-hDOT1L and pcDNA3b-FLAG®-Tat were transfected to 293T cells with or without pHA-Ubiquitin (Ub) by using FUGENE™ 6 transfection reagent (Roche Diagnostics, Indianapolis, Ind.). Twenty-four hours after transfection, MG132 was added at the final concentration of 25 mM, and the cells were cultured for 4 more hours. Cells were then lysed with lysis buffer (50 mM Tris-HCl, pH 7.5, 0.5 mM EDTA, 1% SDS, and 1 mM DTT), and boiled for 10 minutes before centrifugation at 14,000 rpm for 10 minutes. The supernatant was diluted by 10-fold with NP40 lysis buffer (50 mM Tris-HCl, pH 7.5, 150 mM NaCl, 0.1% NP40, 50 mM NaF, 10% glycerol, 1 mM DTT, and 1 mM PMSF), and incubated with 1.5 mg of FLAG®(M2) antibody for 4 hours at 4° C. Protein G beads were then added and incubated further for one hour. The beads were washed three times with lysis buffer containing 0.5% of NP40 before eluting the protein with SDS sample buffer for SDS-PAGE analysis.

Immunofluorescence Staining. U2OS cells ($4 \times 10^4$) were seeded in each well of a 12-well plate one day before transfection. 0.3 µg DNA was used for each transfection by QIAGEN® EFFECTENE™ Transfection Reagents. Twenty-four hours after transfection, cells were washed twice with PBS and then fixed in 3% paraformaldehyde (in PBS) for 10 minutes at room temperature. After washing once with PBS, the cells were incubated with 0.2% TRITON® X-100 (in PBS) for 5 minutes at 4° C. Then the cells were blocked with 0.5% bovine serum albumin (in PBS) for 30 minutes and stained with mouse anti-FLAG®M2 antibody (IBI, Napa, Calif.; 1:1,000) or rabbit anti-HA polyclonal antibody (Abcam, Cambridge, Mass.) for 1 hour at room temperature. After three washes with PBS, the cells were first incubated with rhodamine (or FITC)-conjugated Donkey anti-mouse (or rabbit) immunoglobulin G (IgG) (Jackson ImmunoResearch Laboratories, West Grove, Pa.) diluted 1:50 with 0.5% bovine serum albumin in PBS for 30 minutes and then stained with 1 µg of 4',6'-diamidino-2-phenylindole (DAPI)/mL (Sigma, St. Louis, Mo.) for 10 seconds. The cells were then washed three times with PBS, mounted with DAKO fluorescent mounting medium, and visualized by a Zeiss immunofluorescence microscope.

EXAMPLE 6

Results

Characterization of hDOT1L Localization

Rapid in vivo Degradation of hDOT1L. The in vivo function of hDOT1L was analyzed using a rabbit polyclonal antibody generated against an N-terminal fragment (amino acids 1-351) of hDOT1L. The affinity-purified antibody recognized 3 ng of recombinant GST-hDOT1L(1-351) (FIG. 7A, lane 6) but does not recognize any protein bands around the expected size of about 180 kDa either in nuclear extracts or nuclear pellet proteins derived from HeLa nuclei (FIG. 7A, lanes 4 and 5). Although two specific protein bands below and above the 97 kDa marker were detected in the protein fraction derived from nuclear pellet (FIG. 7A, compare lanes 2 and 5), purification and identification of these proteins indicated that they were not hDOT1L (data not-shown). The fact that we could not detect endogenous hDOT1L in spite of the extensive effort, indicated that either hDOT1L existed at very low abundance or it was subjected to rapid degradation in cells. To examine the stability of hDOT1L, two constructs expressing an N-terminal FLAG®-tagged hDOT1L or a C-terminal HA-tagged hDOT1L were transiently expressed in 293T cells. The cytosol and nuclear extracts derived from the transfected cells were subjected to western blot analysis using FLAG® and HA antibody, respectively. Results shown in FIG. 7B indicate that hDOT1L was subjected to rapid degradation as numerous protein bands were recognized by FLAG® antibody, and less than half of the FLAG®-hDOT1L existed in the full-length form although mixtures of proteinase inhibitors were included during the preparation of the protein extracts. Interestingly, almost no full-length FLAG®-hDOT1L protein was detected in the cytosol while shorter forms of FLAG®-hDOT1L proteins detected by FLAG® antibody were comparable to that in the nuclear extracts (FIG. 7B, compare lanes 1 and 2). This indicated that hDOT1L was more rapidly degraded in the cytosol than in the nucleus. Furthermore, the HA antibody that recognized the C-terminal tag of the recombinant protein detected much fewer protein bands indicating that the C-terminus of the protein was extremely labile.

Subsequently, the stability of the hDOT1L and its subcellular localization was analyzed using hDOT1L simultaneously tagged with an N-terminal FLAG® and a C-terminal HA. After transfection, cells were immunostained with antibodies against FLAG® and HA, respectively (FIG. 7C). Analysis of the transfected cells indicated that the great majority (>80%) of hDOT1L containing the C-terminal HA tag was localized to cytosol, while the majority (about 60%) of hDOT1L containing the N-terminal FLAG® tag was localized to the nucleus. This result is consistent with the observation that full-length hDOT1L is mainly observed in nuclear fractions, while partial hDOT1L protein is enriched in cytosol fraction. This indicates that degradation of hDOT1L may require export of hDOT1L out of the nucleus.

Ubiquitination of hDOT1L. Protein ubiquitination is the major pathway for rapid protein degradation (Pickart (2001) *Annu. Rev. Biochem* 70:503-533). Toward this end, we asked whether hDOT1L is subjected to ubiquitination. We transfected 293T cells with a construct encoding FLAG®-hDOT1L with or without co-transfection of a construct encoding HA-tagged ubiquitin. After immunoprecipitation with anti-FLAG® antibody, the immunoprecipitates were subjected to western blot analysis using anti-HA antibodies. To ensure that FLAG®-hDOT1L was successfully immunoprecipitated, the immunoprecipitates were also blotted with anti-FLAG® antibody (FIG. 8A, bottom panels). Results shown in FIG. 8A indicate that FLAG®-hDOT1L was ubiquitinated in the presence of HA-Ub (top panel, compare lanes 3 and 4). However, the presence of proteasome inhibitor MG132 successfully stabilized ubiquitinated Tat (FIG. 8A, top panel, compare lanes 6 and 7), but did not appear to stabilize the ubiquitinated form of FLAG®-hDOT1L (FIG. 8A, compare lanes 4 and 5), indicating that hDOT1L ubiquitination was not directly linked to its stability.

To analyze the potential function of hDOT1L ubiquitination, hDOT1L ubiquitination sites were mapped using the same approach described above. Different FLAG®-tagged hDOT1L deletion constructs were co-transfected with HA-Ub and the ubiquitination of the different hDOT1L mutants was detected by western blot analysis of HA after immunoprecipitation with the anti-FLAG® antibody. These analyses, summarized in FIG. 8B, allowed us to map the ubiquitination sites to a region between amino acids 469-756 of hDOT1L.

As demonstrated below, hDOT1L(1-767) is localized to cytosol. To determine whether ubiquitination of hDOT1L requires cytoplasm localization, we artificially prevented its cytoplasmic distribution by adding three NLSs to this construct and compared its ubiquitination level with a construct lacking these signals. Immunostaining of transfected cells (data not shown) confirmed that addition of the three NLSs efficiently prevented nuclear export of hDOT1L(1-767). However, western blot analysis of hDOT1L(1-767) with or without the three NLSs indicated that they had similar ubiquitination levels (FIG. 8C, compare lanes 5 and 6). Therefore, it was concluded that hDOT1L ubiquitination can occur both in the cytosol and the nucleus with similar efficiency.

Control of Cellular Localization of hDOT1L. Given that hDOT1L is a nucleosomal histone-specific methyltransferase, we expected that hDOT1L would function in the nucleus. However, results presented in FIG. 7B indicated that transfected hDOT1L could localize to both the nucleus and cytoplasm. To further verify this observation, we transfected a plasmid encoding FLAG®-hDOT1L and visualized the protein localization by immunofluorescent staining using anti-FLAG® antibody (data not shown). These studies confirmed that transiently expressed FLAG®-hDOT1L protein localized to both the nucleus and the cytoplasm.

Active nucleocytoplasmic transport plays an important role in proper regulation and trafficking of nuclear proteins involved in transcription, DNA replication and chromatin remodeling (Schwoebel and Moore (2000) *Essays Biochem.* 36:105-113). Many of these nuclear proteins contain both NLS and nuclear export signal (NES) sequences. In contrast to the sequences of NLS that are more conserved and could be predicted by certain software such as PredictNLS, the sequences of NES vary and no accurate prediction is available. However, most NES sequences do share some common features such as a high percentage of Leucine and other hydrophobic residues. Based on sequences of NES first identified from HIV Rev protein and protein kinase A inhibitor (PKI), a generally accepted loose consensus Leu-Xaa(2,3)-[Leu-Ile-Val-Phe-Met]-Xaa(2,3)-Leu-Xaa-[Leu-Ile] (SEQ ID NO:22) has been proposed. A NES database has been constructed and contains all previously identified NESs; only 36% of the NES sequences fit the widely accepted NES consensus (la Cour, et al. (2003) *Nucleic Acids Res.* 31:393-396).

When the primary sequence of hDOT1L was examined, two potential NLSs were predicted to exist. One was located at the N-terminus and the other at the C-terminus of hDOT1L (FIG. 9). In addition, a putative coiled-coil domain was predicted between amino acid 516-649, which includes a Leucine zipper between amino acids 564-599 (FIG. 9). Thus, we made three deletion mutant constructs of hDOT1L and examined their cellular localization by immunostaining. The N-terminal 472 amino acids mainly exhibited nucleolar localization in U2OS cells (data not shown), which is consistent with the presence of a predicted N-terminal NLS. However, the N-terminal 767 amino acids mainly showed cytoplasmic localization, indicating that there was a strong NES between amino acid 472 and 767, which could override the N-terminal NLS signal. The 756-1537 fragment was mainly localized in the nucleus, consistent with the presence of an NLS in this fragment.

Figure 10A:
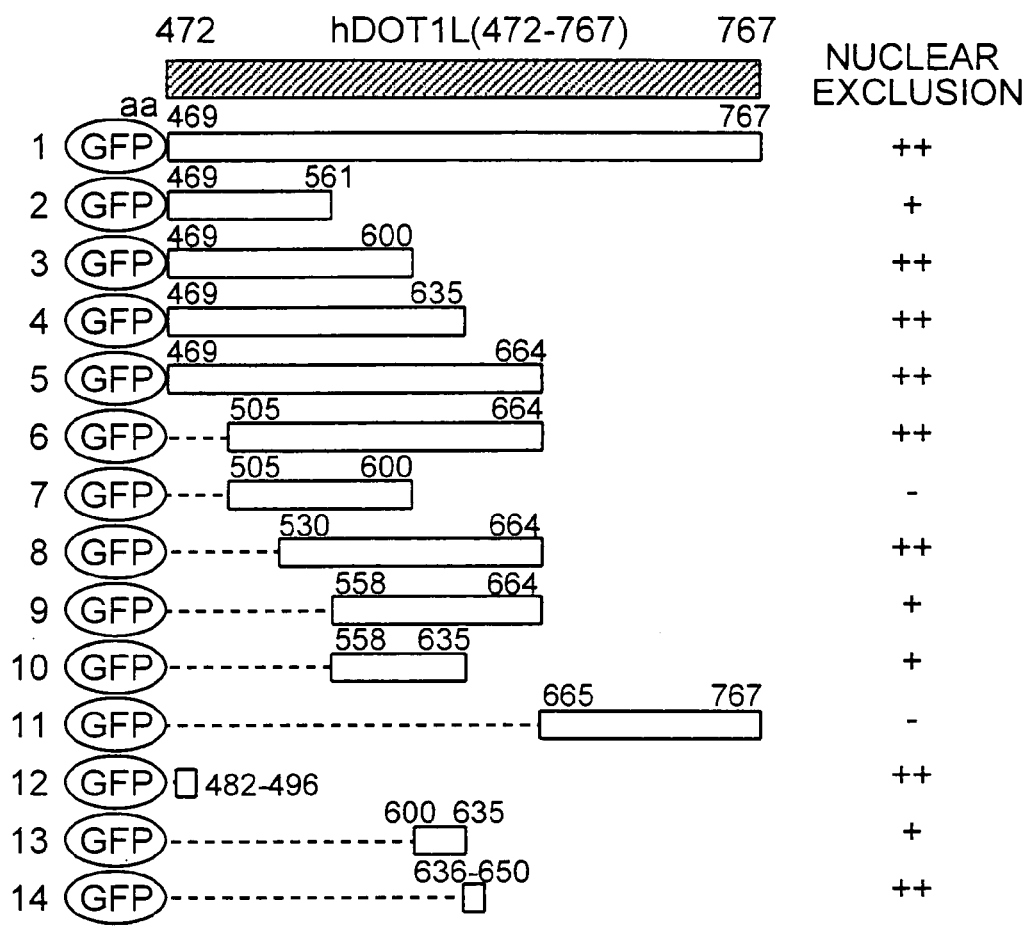
Figure 10B:
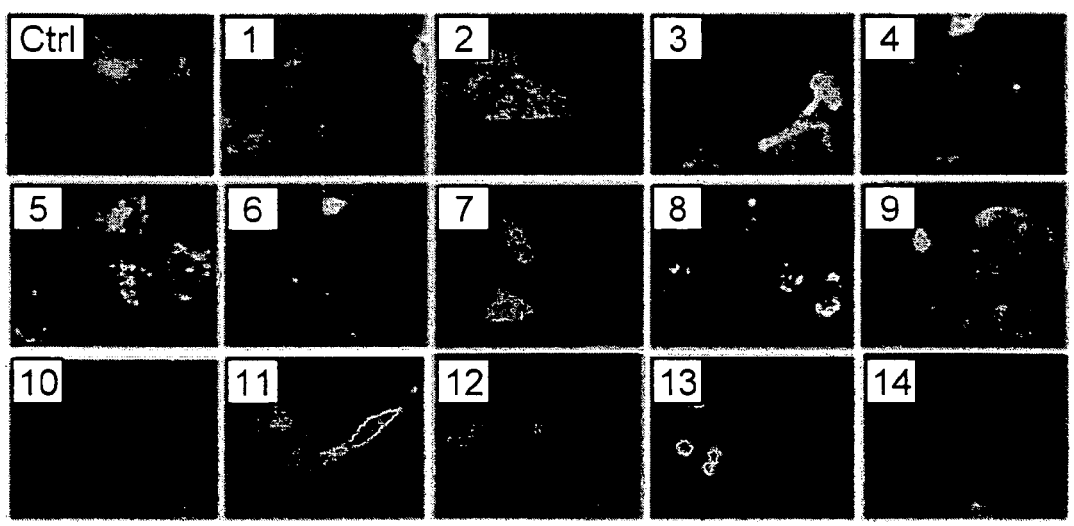
Figure 10C:
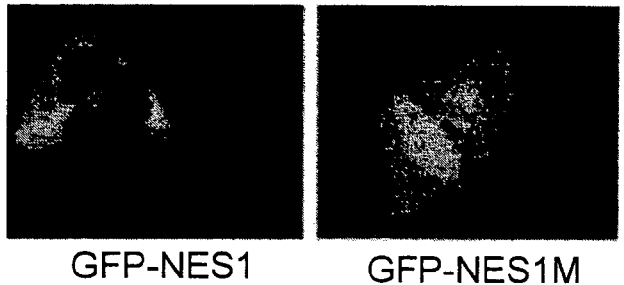
Figure 10D:
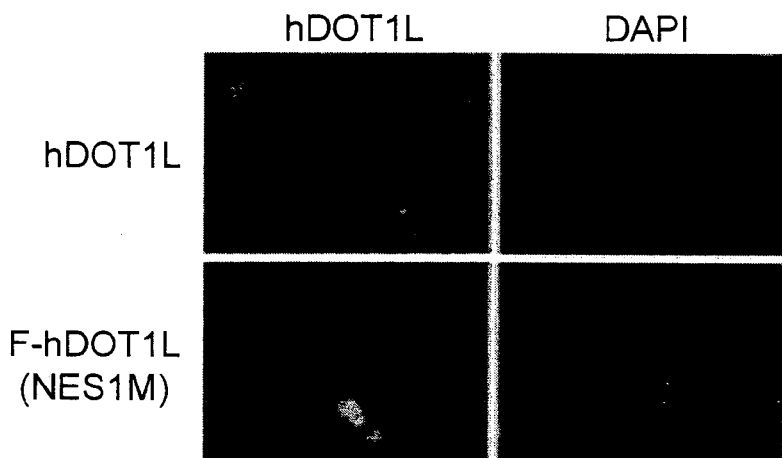
Figure 10E:
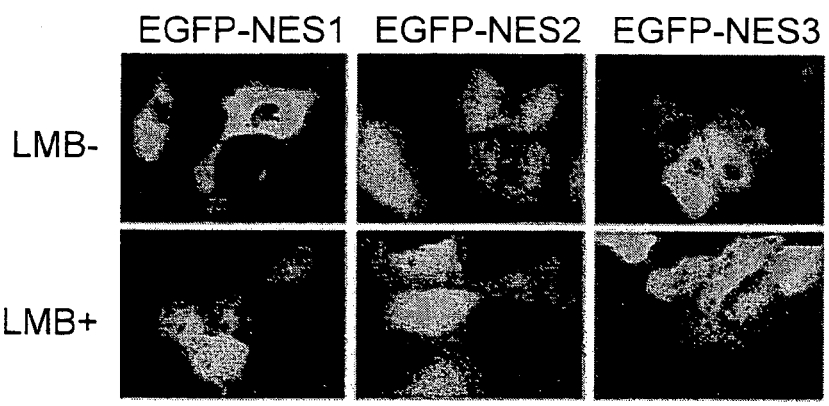

NESs in hDOT1L. Data presented above strongly indicated that there was at least one NES present between amino acids 473-767 of hDOT1L. Inspection of the amino acid sequences in this region failed to identify sequences that matched the NES consensus. To identify the NES in this region, a series of deletion mutants of hDOT1L (469-767) constructs were fused to EGFP (FIG. 10A). After transfection of these deletion mutants into U2OS cells, their cellular localization was visualized in living cells directly. Results presented in FIG. 10B indicate that there were three putative NES sequences in this region. The first NES (NES1) resided between amino acids 482 and 496 having the sequence Pro-Ala-Leu-Gln-Lys-Leu-Leu-Glu-Ser-Phe-Lys-Ile-Gln-Tyr-Leu (SEQ ID NO:12) (FIG. 10B, panel 12). The second NES (NES2) resided between amino acids 600 and 635 (FIG. 10B, panel 13) and the third NES (NES3) resided between amino acids 636 and 650 having the sequence of His-Cys-Leu-Glu-Leu-Gly-Ile-Ser-Ile-Val-Glu-Leu-Glu-Lys-Ser (SEQ ID NO:13) (FIG. 10B, panel 14). Although all three NESs were able to localize fused EGFP to cytoplasm (FIG. 10B, panels 12-14), NES1 and NES3 appeared to be much stronger than NES2. More than 95% of cells transfected with EGFP-NES1 and EGFP-NES3 showed clear nuclear exclusion, whereas about 60% of cells transfected with EGFP-NES2 showed nuclear exclusion, with trace amounts of EGFP still remaining in nuclei. When the sequences of NES1 and NES3 were compared with the NES of the human cAMP-dependent protein kinase inhibitor (PKI), several critical hydrophobic residues were found to be conserved (FIG. 10C). While most of the conserved amino acids were Leucine or Isoleucine, NES1 and NES3 have Phenylalanine or Valine instead of Leucine at one of the conserved residues. Previous studies indicate that C-terminal hydrophobic residues in NES sequences are more important for nuclear export function than N-terminal Leucines (Zhang and Xiong (2001) *Science* 292(5523):1910-5). To examine whether this was true for NES1, both the Phenylalanine and the Isoleucine of NES1 were mutated to Alanine. It was found that C-terminal hydrophobic residues were important for NES function as mutations on the two residues completely abrogated the nuclear exclusion ability of NES1 (FIG. 10C). While the NES1 itself was capable of localizing EGFP to cytoplasm, it was important to demonstrate that NES1 was functional in nuclear exclusion in the context of full-length hDOT1L. Thus, we examined the localization of a full-length hDOT1L NES1 mutant and found that mutation of NES1 prevented cytoplasm localization of hDOT1L (FIG. 10D) indicating that NES1 is important for hDOT1L nuclear export.

To further characterize the nuclear export ability of the three NESs identified, it was determined whether the NESs were involved in active nuclear export mediated by the CRM1 (chromosomal region maintenance) pathway. CRM1 was initially identified as a *S. pombe* protein whose mutation affects higher order chromosome structure (Adachi and Yanagida (1989) *J. Cell Biol.* 108:1195-1207). Subsequent studies indicate that CRM1 is an export receptor for Leucine-rich nuclear export signals (Fornerod, et al. (1997) *Cell* 90:1051-1060; Ossareh-Nazari, et al. (1997) *Science* 278:141-144; Stade, et al. (1997) *Cell* 90:1041-1050). Leptomycin B (LMB), a *Streptomyces* metabolite, has been shown to be capable of preventing CRM1-mediated active nuclear export through covalent attachment to a Cysteine residue in the central region of CRM1 (Kudo, et al. (1998) *Exp. Cell Res.* 242:540-547; Nishi, et al. (1994) *J. Biol. Chem.* 269:6320-6324). To investigate the effect of LMB treatment on the nuclear export ability of the NESs, U2OS cells were transfected with constructs encoding each of the three NESs fused with EGFP in the presence or absence of 20 nM of LMB. Eight hours after LMB treatment, green fluorescence was observed under a microscope in living cells. Results shown in FIG. 10E demonstrate that LMB treatment prevented nuclear export by all the three NESs. These results indicate that hDOT1L nuclear export is mediated through the CRM1 pathway.

EXAMPLE 7

Experimental Procedures hDOT1L and MLL-AF10-Mediated Leukemogenesis

Constructs. For yeast two-hybrid screening, the coding sequence of hDOT1L was cloned in-frame with the Gal4 DNA-binding domain in the pGBKT7 plasmid. For the mammalian two-hybrid assay (CLONTECH™, Palo Alto, Calif.), various regions of hDOT1L were cloned into the pM vector (CLONTECH™) to generate fusions with the Gal4 DNA-binding domain. Various regions of AF10 were cloned into the pVP16 vector (CLONTECH™) to generate fusions with the VP16 transcriptional activation domain. pG5LUC is a reporter vector which contains the luciferase coding region downstream of the minimal promoter of the adenovirus E1b gene and five GAL4 binding sites. For retroviral vector construction, 5' LTR region of murine stem cell virus vector (MSCVneo, CLONTECH™) were replaced by cytomegalovirus immediate early promoter sequences (MSCN). MSCN-MLL(N) and MSCN-MLL-AF10 were constructed from MSCV-5'MLL and MSCV-MLL-AF10 with a FLAG®-tag upstream of MLL gene. MSCN-hDOT1L constructs were constructed by inserting a hDOT1L cDNA (encoding amino acids 1-416 and 1-670, respectively) downstream of MLL gene. MSCB vector was constructed by the replacement of neomycin-resistant gene of MSCN with the blasticidin-resistant gene, and insertion of the full-length of hDOT1L (encoding amino acids 1-1,537) downstream of a FLAG®-tag.

Yeast Two-Hybrid Screen. To identify hDOT1L interacting proteins, yeast two-hybrid screening was performed with the MATCHMAKER™ Gal4 two-hybrid system 3 (CLONTECH™). The cDNA encoding the full-length hDOT1L was fused in-frame to the GAL4 DNA-binding domain in the bait vector-pGBKT7. This construct was transformed into Saccharomyces cerevisiae host strain AH109. A Pre-transformed Mouse Testis MATCHMAKER™ cDNA Library (CLONTECH™) was screened by mating with the bait strain in accordance with the manufacturer's instructions. Approximately 4.8×10$^6$ individual clones were screened and about 53 clones grew on the selected medium lacking His, Ade, Trp and Leu. The clones were further selected by growth on SD/-Ade/-His/-Leu/-Trp/X-a-Gal master plates. The prey plasmids were rescued and electroporated into E. coli strain Top 10. The DNA recovered from the bacteria was sequenced to identify the candidate proteins that interact with hDOT1L.

Cell Culture, Transfections, Immunoprecipitation and Immunofluorescence. 293T and U2OS cells were maintained in DMEM supplemented with 10% fetal calf serum and grown at 37° C. with 5% $CO_2$. Cell transfection and immunoprecipitations were conducted as described in Example 5 above.

Immunofluorescence Staining. Performed as described in Example 5 above.

Retrovirus Preparation and Transduction. MSCN vector containing MLL-AF10 or MLL-hDOT1L were co-transfected with pGag-pol and pVSVG to human embryonic kidney cells (293T) by a standard calcium-phosphate method. After 48 to 72 hours of transfection, the supernatants were collected and were used for bone marrow cell transduction as follows: 4 to 12-week old C57BL/6 mice were injected intravenously with 5-fluorouracil (150 mg/kg), and bone marrow (BM) cells were harvested from both femurs at 5 days post-injection. Retroviral supernatants were used to transduce BM cells by spinoculation. After two derail infections, infected cells were plated into methylcellulose cultures.

Methylcellulose Colony Assays. Retrovirally-infected BM cells (1×10$^4$) were plated in 0.9% methylcellulose (Stem Cell Technologies, Vancouver, BC) supplemented with 10 ng/mL murine IL-3, IL-6, GM-CSF, and 50 ng/mL SCF in the presence of 1 mg/mL G418 (GIBCO, Grand Island, N.Y.). After 7 days of culture, the number of colonies was counted and 1×10$^4$ cells of the single-cell suspensions prepared from G418-resistant colonies were replated into methylcellulose supplemented with the same growth factors without G418. Further plating was repeated every 10 days. For the experiment in FIG. 15, 1×10$^4$ cells were plated with 5 µg/mL of Blasticidin.

RT-PCR Analysis of Hox Genes. Total RNA was isolated from primary bone marrow cells or MLL-AF10/MLL-hDOT1L-transduced cells using RNEASY® (QIAGEN®). One microgram of total RNA was treated with RNase-free DNase I, and applied for reverse transcription using IMPROM-II™ (PROMEGA®, Madison, Wis.) according to manufacturer's protocol. The resulting cDNA was used as template for PCR amplification of Hox genes using PLATINUM® Taq Polymerase (INVITROGEN™, Carlsbad, Calif.). Primers sequences were designed based on the known hox gene sequences.

Mouse Transplantation and Histological Analysis. Six-week-old non-obese/severe combined immunodeficiency (NOD/SCID) mice were injected intravenously through ophthalmic vein with 10$^6$ MLL-hDOT1L(1-670)- or MLL-AF10-transduced BM cells derived from the 3$^{rd}$ round of methylcellulose colonies. For tumor analysis, tumor tissues were fixed in 4% paraformaldehyde. After being paraffin embedding and sectioning, slides were stained with hematoxylin and eosin using standard techniques.

EXAMPLE 8

Results hDOT1L and MLL-AF10-Mediated Leukemogenesis

AF10 Interacts with hDOT1L. Having cloned and characterized the structure, H3-K79-specific methyltransferase activity, and subcellular localization of hDOT1L, we searched for functional partners by yeast two-hybrid screening. This screen resulted in repeated isolation of cDNAs encoding the C-terminal half of AF10 (FIG. 11A), a frequent fusion partner of MLL and CALM in leukemia (Chaplin, et al. (1995) *Blood* 86:2073-2076; Dreyling, et al. (1996) *Proc. Natl. Acad. Sci. USA* 93:4804-4809). To confirm the interaction, we co-expressed AF10 and hDOT1L, respectively tagged with FLAG® and HA. Following immunoprecipitation with anti-FLAG® antibody and western blot analysis with anti-HA antibody, we demonstrated that the two proteins can be co-immunoprecipitated (FIG. 11B, compare lanes 3 and 6). In addition, the interaction was also confirmed by mammalian two-hybrid assays (FIG. 12 and FIG. 13). Therefore, AF10 associates with hDOT1L in vivo.

Figure 12A:
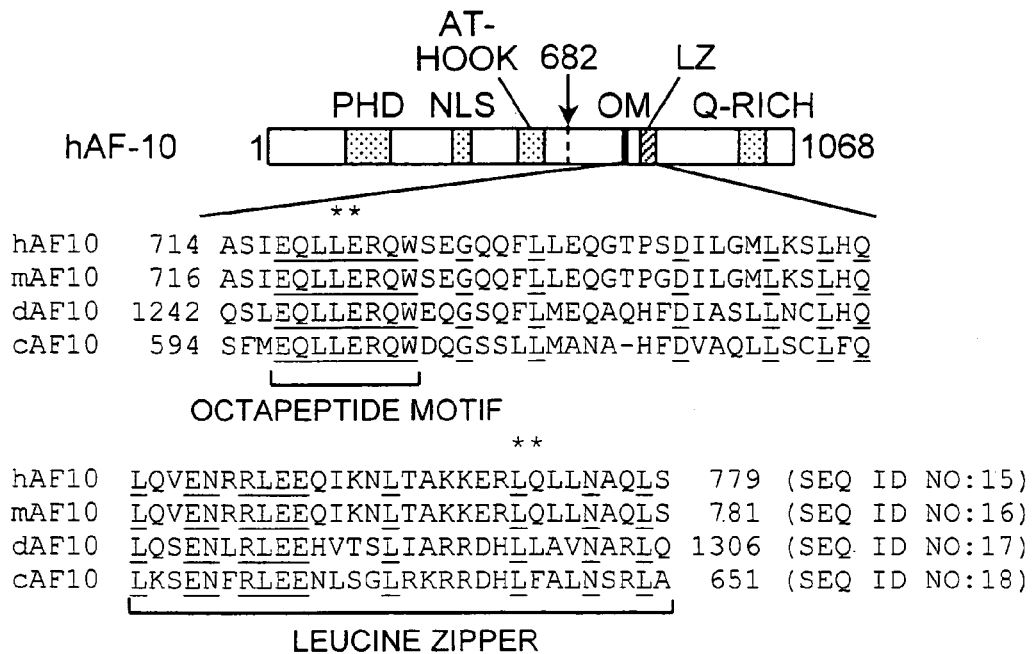
Figure 12B:
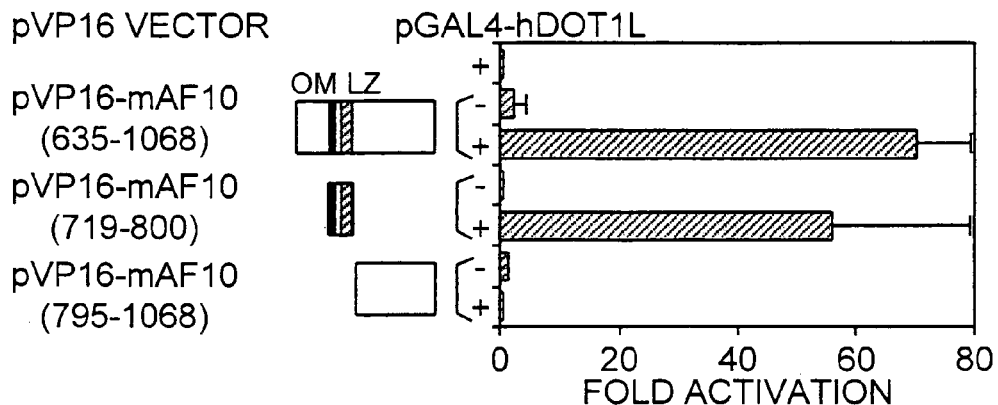
Figure 12C:
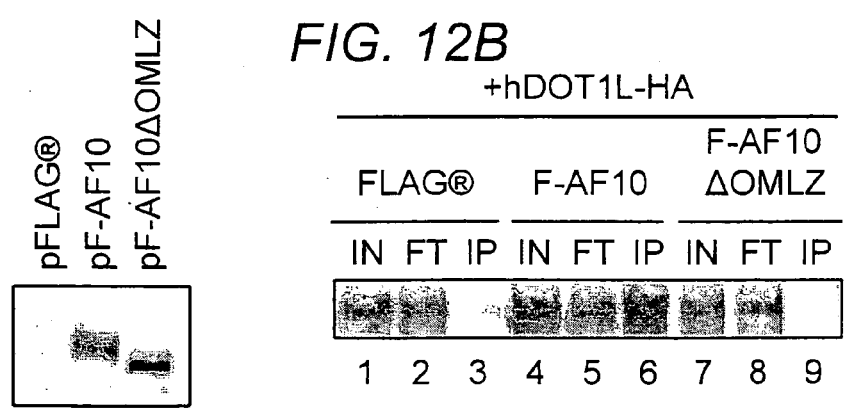
Figure 12D:
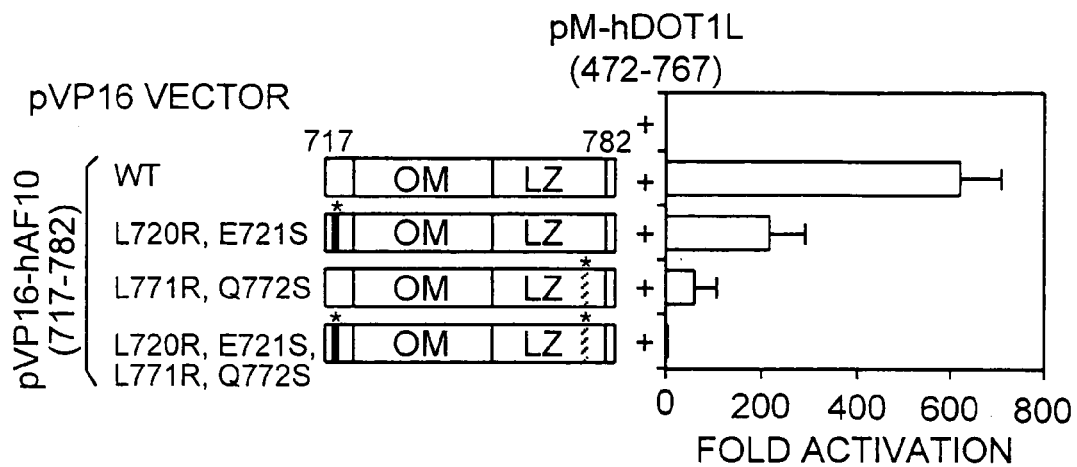

The OM-LZ Region of AF10 is Necessary and Sufficient for the AF10-hDOT1L Interaction. AF10 was initially discovered by virtue of its involvement in t(10; 11)(p12; q23) chromosomal translocations found in acute myeloid leukemia patients (Chaplin, et al. (1995) *Blood* 86:2073-2076). This genetic rearrangement results in fusion of the C-terminal half of AF10 to the N-terminal third of MLL. AF10 contains several motifs common to transcription factors, and the minimal portion of AF10 fused to MLL contains a leucine zipper (LZ) motif that is highly conserved between homologs of AF10 from C. elegans to human (FIG. 12A). To characterize the nature of the AF10-hDOT1L interaction, we mapped the region(s) of AF10 involved in the interaction. Mammalian two-hybrid assays were performed in 293T cells. AF10 and hDOT1L, fused to the VP16 activation domain and the Gal4-DBD, respectively, were co-expressed in the presence of a luciferase reporter containing five Gal4 binding sites. Results shown in FIG. 12B demonstrate that a region of about 80 amino acids (amino acids 719-800) is sufficient to mediate the interaction. Interestingly, this same region has been recently demonstrated to be required for leukemic transformation of the MLL-AF10 fusion protein (DiMartino, et al. (2002) *Blood* 99:3780-3785). To evaluate whether this 80-amino acid region was necessary for the interaction, we created an AF10 construct where this region was deleted. FLAG®-tagged AF10 with or without this region was co-expressed with hDOT1L-HA and their ability to interact with each other was analyzed by co-immunoprecipitation. Although both constructs were expressed to a similar level (FIG. 12C, left panel), deletion of this 80 amino acid region abrogated the ability of AF10 to interact with hDOT1L (FIG. 12C, right panel, compare lanes 6 and 9). Therefore, we concluded that the 80-amino acid region was necessary for the AF10-hDOT1L interaction.

In addition to a leucine zipper, this 80-amino acid region also includes an octapeptide motif (OM), (Glu-Gln-Leu-Leu-Glu-Arg-Gln-Trp; SEQ ID NO:19), which is highly conserved among AF10 homologs (FIG. 12A). Previous studies indicate that fusion of OM or LZ alone to MLL is not sufficient for leukemic transformation. However, fusion of MLL to OM+LZ is sufficient for leukemic transformation (DiMartino, et al. (2002) *Blood* 99:3780-3785). To evaluate the relative contribution of OM and LZ to hDOT1L interaction, we created constructs harboring mutations in the two regions individually or in combination and analyzed their effect on the AF10-hDOT1L interaction using the mammalian two-hybrid assay described herein. Results shown in FIG. 12D indicate that while mutation in each of the two regions greatly reduced their interaction, mutation in both regions simultaneously completely destroyed the interaction. Thus, it was concluded that both OM and LZ contributed to the hDOT1L-AF10 interaction. Collectively, these data indicate that the OM-LZ region required for leukemic transformation is both necessary and sufficient for hDOT1L-AF10 interaction.

A Leucine-Rich Region Mediates the AF10-hDOT1L Interaction. Having defined the region in AF10 required for the AF10-hDOT1L interaction, we mapped the region(s) in hDOT1L involved in the interaction. Constructs encoding different regions of the hDOT1L were generated and co-expressed with AF10 in 293T cells. The ability of these hDOT1L deletion mutant proteins to interact with AF10 was analyzed by co-immunoprecipitation. Results shown in FIG. 13A indicate that a region of 294 amino acids (amino acids 473-766) to be important for the interaction (compare lanes 8 and 10).

To confirm these results and narrow down the interaction region, the mammalian two-hybrid assay described above4 was used. Specifically, a plasmid encoding the VP16 activation domain fused to the OM-LZ region of AF10 was co-expressed with various constructs encoding Gal4DBD fused to different portions of hDOT1L(472-767). Interaction was measured by activation of a luciferase reporter containing five Gal4 binding sites. Comparison of the activation ability of the first five constructs allowed us to map the interaction domain to a region of 130 amino acids (amino acids 500-630) predicted to form a coiled-coil domain with potential to be a leucine zipper (FIG. 13B, 1-5). Further deletion and mutational studies identified two leucine residues (L532 and L592) critical to the interaction (FIG. 13B, 6-9). The importance of these two leucine residues in mediating the hDOT1L and AF10 interaction was verified in the context of partial and full-length hDOT1L (FIG. 13B, 10-13). Accordingly, it was concluded that a leucine rich region between amino acids 500-630 of hDOT1L is involved in hDOT1L and AF10 interaction and at least two of the leucine residues (L532 and L592) are critical for the interaction.

Immortalization of Primary Murine Myeloid Progenitor Cells by MLL-hDOT1L. The fact that the OM-LZ domain of AF10 is both necessary and sufficient in mediating AF10 and hDOT1L interaction in combination with the fact that the same region is required for leukemic transformation (DiMartino, et al. (2002) *Blood* 99:3780-3785) raised the possibility that MLL-AF10-mediated leukemic transformation may involve recruitment of hDOT1L and its associated HMTase activity to affect expression of MLL target genes. Consistent with this, immunofluorescence staining revealed co-localization of transfected hDOT1L and MLL-AF10 as large nuclear foci (data not shown). If the fused AF10 in MLL-AF10 only serves to recruit hDOT1L, leukemic transformation may be achieved by direct fusion of hDOT1L to MLL. To test this, a methylcellulose serial replating assay, outlined in FIG. 14A, was used to assess immortalization of murine myeloid progenitor cells by MLL-hDOT1L. A modified murine stem cell virus (MSCV)-derived retroviral vector, designated as MSCN, was used to transduce freshly harvested bone marrow cells from mice pretreated with 5-flurouracil. MSCN constructs encoding MLL sequences 5' of the translocation breakpoint with AF10 (MLL-N), MLL-AF10 that mimic the most frequent fusion involving the two proteins, MLL fused to various length of hDOT1L, and hDOT1L were made (FIG. 14B). To facilitate expression analysis of these constructs, an N-terminal FLAG®-tag was added to each of the constructs. Due to the size limitation for efficient packaging of retroviral vectors, MLL-hDOT1L fusion constructs encoding more than the first 670 amino acids of hDOT1L had dramatically decreased retroviral transduction efficiency (data not shown), which prevented us from analyzing MLL-hDOT1L that contained the full-length hDOT1L using this assay. Nevertheless, retroviruses with similar titer as that of MLL-AF10 were successfully generated with MLL-hDOT1L(1-416) and MLL-hDOT1L(1-670) (data not shown). As disclosed herein, hDOT1L(1-416) has robust H3-K79 methyltransferase activity in vitro. Importantly, transient transfection of MLL-hDOT1L(1-416) and MLL-hDOT1L(1-670) into 293T cells resulted in increased H3-K79 methylation in vivo (data not shown) indicating that both fusion proteins were enzymatically active. Similar to the full-length hDOT1L mutant, the two parallel constructs that harbor "GSG163-165RCR" mutations were enzymatically inactive in the same assay (data not shown). Western blot analysis of extracts from transiently-transfected retroviral packaging cells confirmed that MLL-N, MLL-AF10, MLL-hDOT1L(1-416), MLL-hDOOT1L(1-670), and hDOT1L constructs were efficiently expressed (data not shown). Plating of cells transduced with the various MSCN constructs under selective conditions showed a variable number (50-100) of colonies that were consistent with their respective virus titer. However, significant differences were observed in a second round of plating of $10^4$ cells pooled from colonies harvested from the first round of cultures. Compared to the first round, vector alone, MLL-N, hDOT1L, and the two MLL-hDOT1L mutants transduced cultures produced a decreased number of secondary colonies. In contrast, MLL-hDOT1L(1-416), MLL-hDOT1L(1-670) and MLL-AF10 transduced cells gave rise to hundreds of colonies, an amount significantly higher than that from the first round of plating. When a third round of plating was assayed, only MLL-hDOT1L(1-670) and MLL-AF10 transduced cells gave rise to an increased number of colonies compared with that from the second round of plating. It was therefore concluded that similar to MLL-AF10, MLL-hDOT1L(1-670) has leukemic transformation capability. This ability depends on both the hDOT1L H3-K79 methyltransferase activity and the region between amino acid 417-670.

HMTase Activity of hDOT1L is Required to Maintain the Growth Capacity of MLL-AF10-Transformed Cells. To further demonstrate that the enzymatic activity of hDOT1L is critical in MLL-AF10-mediated leukemogenesis, we examined the effect of the wild-type hDOT1L and the HMTase-defective mutant hDOT1L on the sustaining growth capability of MLL-AF10-transduced bone marrow cells. Nucleic acid sequences encoding full-length wild-type and HMTase-defective mutant hDOT1L proteins were cloned into the retroviral vector PMSCB which expresses the Blasticidin resistant gene. Viruses generated using this vector were used to infect MLL-AF10-transduced bone marrow cells derived from the third round of plating (FIG. 15A). Cells expressing hDOT1L were selected in the presence of Blasticidin. After 10 days of methylcellulose culture, we observed a dramatic difference in the colony formation assay (FIG. 15B). While transduction of wild-type hDOT1L into MLL-AF10 expressing-cells still supported colony formation, transduction of HMTase-defective hDOT1L into MLL-AF10 expressing-cells completely eliminated the ability of MLL-AF10 to support colony formation. These results support the finding that MLL-AF10's ability to sustain the growth of transformed bone marrow cells is dependent upon the HMTase activity of hDOT1L. It also indicates that the HMTase-defective hDOT1L protein can function as a dominant-negative factor in maintaining the growth capacity of MLL-AF10 transformed cells.

Immortalization of Murine Myeloid Progenitors by MLL-hDOT1L. While MLL-hDOT1L(1-670) is capable of transforming bone marrow cells, the number of colonies formed is different from that of MLL-AF10 (FIG. 14C). In addition, the morphology of the colonies formed also appeared to be different (FIG. 16A). Similar to a previous report (DiMartino, et al. (2002) Blood 99:3780-3785), colonies arising from MLL-AF10-transduced bone marrow cells exhibited round, compact morphology (FIG. 16A). In contrast, MLL-hDOT1L(1-670)-transformed bone marrow cells form colonies with two types of morphologies that were different from that of MLL-AF10 transformed cells (FIG. 16A). Interestingly, the cells of type 11 colonies from MLL-DOT1(1-670)-transformed cells have a significant growth advantage relative to that of type I colonies in the third round of plating (FIG. 16B). To determine the cell lineage of these colonies, immunophenotyping of these cells in early liquid cultures was performed. Consistent with myeloid cell lineage, many cells derived from MLL-AF10-transformed colonies or the type I MLL-hDOT1L-transformed colonies expressed the early myeloid markers Mac-1 and c-Kit (FIG. 16C). In contrast, the majority of cells from the type II colonies of MLL-hDOT1L-transformed cells were negative for Mac-1 or c-Kit, indicating they were most likely not of myeloid lineage (FIG. 16C). These results indicated that although MLL-hDOT1L(1-670) was capable of immortalizing bone marrow cells arrested at a relatively early stage of myeloid differentiation, it could not completely phenocopy MLL-AF10. Whether the difference was caused by the use of partial, instead of the full-length, hDOT1L in the MLL fusion and colony assay remains to be determined.

Up-Regulation of a Specific Subset of Hox Genes in MLL-hDOT1L-Mediated Myeloid Transformation. Similar to its Drosophila homologue Trx, mouse MLL plays an important role in maintaining the Hox gene expression pattern during embryogenesis (Yu, et al. (1995) Nature 378:505-508). In addition to participating in embryogenesis, Hox gene expression also plays important roles in normal hematopoiesis and leukemogenesis processes (Buske and Humphries (2000) Int. J. Hematol. 71:301-308; Sauvageau, et al. (1994) Proc. Natl. Acad. Sci. USA 91:12223-12227). To understand how hDOT1L and its associated HMTase activity may contribute to leukemogenesis, we determined the expression profile of Hox genes in murine primary bone marrow cells before and after immortalization by MLL-AF10 or MLL-hDOT1L(1-670). Since these cell lines represent the earliest stages of myeloid leukemogenesis, they likely have sustained very few, if any, secondary mutations. Given that MLL-hDOT1L-transformed bone marrow cells give rise to two types of morphologically different colonies, we analyzed their Hox gene expression patterns separately. Accordingly, RNAs were isolated from primary, MLL-AF10- or MLL-hDOT1L-transformed bone marrow cells. Expression of individual Hox genes in these cells was analyzed by reverse transcriptase PCR (RT-PCR). GAPDH was used as a control for equal RNA input for the different samples. Similar to a previous report (Ayton and Cleary (2003) Genes Dev. 17:2298-2307), cells immortalized by MLL-AF10 have the most numbers of genes in the HoxA complex up-regulated relative to that in primary bone marrow cells (FIG. 17A). Consistent with the colony assay result demonstrating that the colonies generated from MLL-hDOT1L(1-670)-transduced cells were different from those generated from MLL-AF10 transduced cells, cells derived from both types of MLL-hDOT1L(1-670)-transduced colonies had fewer numbers of Hox genes up-regulated relative to the MLL-AF10-transformed cells. Indeed, a complete analysis of all the 39 Hox genes identified HoxA9 as the only gene that was up-regulated in MLL-AF10 and both types of MLL-hDOT1L(1-670)-transformed cells (FIG. 17B). These data indicate that HoxA9 is likely to be a critical gene in leukemogenesis-mediated by MLL fusion proteins.

MLL-hDOT1L-Transduced Cells Induce Tumors in Mice. The fact that MLL-hDOT1L can transform bone marrow cells in the colony assay indicates that hDOT1L may be an oncogene. To evaluate the tumorgenic potential of MLL-hDOT1L, cells derived from third round of plating were transplanted into SCID mice. Of the four mice transplanted with MLL-hDOT1L-transformed cells, two developed terminal tumor within four weeks of transplantation, the other two mice still appeared healthy at five weeks after transplantation (data not shown). The control mice and the mice transplanted with MLL-AF10-transformed cells still appeared healthy at four weeks of transplantation, consistent with previous reports that SCID mice transplanted with MLL-AF10-transformed bone marrow cells have at least eight weeks of latency. Histological analysis of the tumor derived from transplant of MLL-hDOT1L-transformed bone marrow cells revealed the tumor as undifferentiated tumor (data not shown).

hDOT1L Transports AF10 to the Cytosol. Results provided herein indicate that hDOT1L participates in MLL-AF10-mediated leukemogenesis. To understand the functional consequence of the AF10 and hDOT1L interaction in a non-leukemic situation, we examined the effect of their association on their cellular localization in view of the fact that the three NESs of hDOT1L overlap with the region involved in the AF10 interaction. AF10 and hDOT1L, tagged with green fluorescent protein (GFP) and FLAG®, respectively, were transfected into U2OS cells and their cellular localization was viewed by microscopy. Immunostaining with anti-FLAG® antibody revealed that hDOT1L localized to both the nucleus and the cytoplasm while GFP-AF10 localized to the nucleus exclusively when the two proteins were expressed individually (data not shown). Unexpectedly, when co-expressed, these proteins not only co-localized, but were also excluded from nucleus (data not shown), indicating that one of the consequences of AF10 and hDOT1L association is export of both proteins to cytoplasm. Given that the function of hDOT1L is to methylate nucleosomal histone H3, association with AF10 and subsequent transport to cytosol likely impedes the ability of hDOT1L to methylate nucleosomal H3. In addition, the nuclear function of AF10 is most likely affected by its export from nucleus. It is possible that the association of AF10 with hDOT1L may expose the NLS of hDOT1L and facilitate its nuclear export.

These results, in combination with the finding that MLL-AF10 can direct the nuclear localization of hDOT1L allowed us to propose a function for hDOT1L in normal and leukemia cells. Not to be bound by theory, AF10 is possibly exported from nucleus when it associates with hDOT1L under normal conditions (FIG. 18A). However, in leukemia cells, where the C-terminal part of AF10 is fused to MLL, although the MLL-AF10 fusion protein is still capable of interacting with hDOT1L through the OM-LZ present in the C-terminal half of AF10, the MLL-AF10/hDOT1L complex cannot export from the nucleus either because the N-terminal of AF10 is missing or because the nuclear localization signal in MLL keeps the protein complex from exporting (FIG. 18B). Regardless of the underlying mechanism, one significant epigenetic change in leukemia cells relative to that of normal cells is predictable. It has been demonstrated that MLL is an H3-K4 methyltransferase (Milne, et al. (2002) Mol. Cell 10:1107-1117; Nakamura, et al. (2002) *Mol. Cell* 10:1119-1128). The promoter of MLL target genes, for example HoxA9, are likely to be enriched for H3-K4 methylation in normal cells. However, in leukemia cells, as a consequence of MLL and AF10 fusion, the promoter of MLL target gene will not be enriched for H3-K4 methylation due to the loss of the MLL C-terminal SET domain. Instead, the MLL-AF10 fusion will bring in the hDOT1L resulting in H3-K79 methylation of the MLL target gene promoter (FIG. 18A and FIG. 18B).

The foregoing is illustrative of the present invention, and is not to be construed as limiting thereof. The invention is defined by the following claims, with equivalents of the claims to be included therein.

That which is claimed is:

1. An isolated DOT1L polypeptide comprising the amino acid sequence of SEQ ID NO:2.

2. The isolated DOT1L polypeptide of claim 1 consisting of the amino acid sequence of SEQ ID NO:2.

3. A fusion protein comprising the DOT1L polypeptide of claim 1.

4. An isolated functional fragment of SEQ ID NO:2 comprising at least 400 amino acids of the amino acid sequence of SEQ ID NO:2 or an amino acid sequence having at least 95% amino acid sequence similarity thereto, wherein said functional fragment comprises a DOT1L histone methyltransferase catalytic domain and has H3-K79 methyltransferase activity, further wherein said domain comprises amino acids 157 to 270 of SEQ ID NO:2 or an amino acid sequence having at least 95% amino acid sequence similarity thereto.

5. The isolated functional fragment of claim 4, wherein the catalytic domain of the functional fragment further comprises amino acids 121-306 of SEQ ID NO:2 or an amino acid sequence having at least 95% amino acid sequence similarity thereto.

6. The isolated functional fragment of claim 4, further comprising amino acids 390 to 407 of SEQ ID NO:2 or an amino acid sequence having at least 95% amino acid sequence similarity thereto.

7. The isolated functional fragment of claim 4 further comprising a leucine rich region that binds AF10.

8. The isolated functional fragment of claim 7, wherein the leucine rich region that binds AF10 comprises amino acids 500 to 630 of SEQ ID NO:2 or an amino acid sequence having at least 95% amino acid sequence similarity thereto.

9. The isolated functional fragment of claim 4 further comprising a nuclear export signal.

10. The isolated functional fragment of claim 9, wherein the nuclear export signal comprises an amino acid sequence selected from the group consisting of:
   (i) amino acids 482 to 496 of SEQ ID NO:2 or an amino acid sequence having at least 95% amino acid sequence similarity thereto;
   (ii) amino acids 600 to 635 of SEQ ID NO:2 or an amino acid sequence having at least 95% amino acid sequence similarity thereto;
   (iii) amino acid 636 to 650 of SEQ ID NO:2 or an amino acid sequence having at least 95% amino acid sequence similarity thereto; and
   (iv) a combination of any of (i) to (iii) above.

11. The isolated functional fragment of claim 9, wherein the nuclear export signal comprises amino acids 472 to 767 of SEQ ID NO:2 or an amino acid sequence having at least 95% amino acid sequence similarity thereto.

12. A fusion protein comprising the isolated functional fragment of claim 4.

* * * * *

UNITED STATES PATENT AND TRADEMARK OFFICE
CERTIFICATE OF CORRECTION

| | | |
|---|---|---|
| PATENT NO. | : 7,442,685 B2 | Page 1 of 1 |
| APPLICATION NO. | : 10/866908 | |
| DATED | : October 28, 2008 | |
| INVENTOR(S) | : Zhang et al. | |

It is certified that error appears in the above-identified patent and that said Letters Patent is hereby corrected as shown below:

In the Application:

Column 1, Line 15: Please correct "Nos. GM63076 and GM68804 awarded by the National"
to read -- Nos. GM63067 and GM68804 awarded by the National --

Signed and Sealed this
Fourteenth Day of June, 2011

David J. Kappos
*Director of the United States Patent and Trademark Office*

UNITED STATES PATENT AND TRADEMARK OFFICE
CERTIFICATE OF CORRECTION

PATENT NO.       : 7,442,685 B2
APPLICATION NO.  : 10/866908
DATED            : October 28, 2008
INVENTOR(S)      : Zhang et al.

It is certified that error appears in the above-identified patent and that said Letters Patent is hereby corrected as shown below:

Title Page, Item (75) Inventor is corrected to read:
-- Yi Zhang, Chapel Hill (NC);
    Qin Feng, Houston (TX) --.

Signed and Sealed this
Fifteenth Day of March, 2016

Michelle K. Lee
*Director of the United States Patent and Trademark Office*

```
                           SEQUENCE LISTING

<160> NUMBER OF SEQ ID NOS: 22

<210> SEQ ID NO 1
<211> LENGTH: 4889
<212> TYPE: DNA
<213> ORGANISM: Homo sapiens

<400> SEQUENCE: 1
cccgcctagc atggtgcggc ggccgcgcgc gcggacatgg gggagaagct ggagctgaga      60
ctgaagtcgc ccgtgggggc tgagcccgcc gtctaccgt ggccgctgcc ggtctacgat     120
aaacatcacg atgctgctca tgaaatcatc gagaccatcc gatgggtctg tgaagaaatc     180
ccggatctca agctcgctat ggagaattac gttttaattg actatgacac caaaagcttc     240
gagagcatgc agaggctctg cgacaagtac aaccgtgcca tcgacagcat ccaccagctg     300
tggaagggca ccacgcagcc catgaagctg aacacgcggc cgtccactgg actcctgcgc     360
catatcctgc agcaggtcta caaccactcg gtgaccgacc ccgagaagct caacaactac     420
gagcccttct cccccgaggt gtacggggag acctccttcg acctggtggc ccagatgatt     480
gatgagatca agatgaccga cgacgacctg tttgtggact tggggagcgg tgtgggccag     540
gtcgtgctcc aggttgctgc tgccaccaac tgcaaacatc actatggcgt cgagaaagca     600
gacatcccgg ccaagtatgc ggagaccatg gaccgcgagt tcaggaagtg gatgaaatgg     660
tatggaaaaa agcatgcaga atacacattg gagagaggcg atttcctctc agaagagtgg     720
agggagcgaa tcgccaacac gagtgttata tttgtgaata atttttgcctt tggtcctgag     780 gtggatcacc agctgaagga gcggtttgca aacatgaagg aaggtggcag aatcgtgtcc     840
tcgaaaccct ttgcacctct gaacttcaga ataaacagta gaaacttgag tgacatcggc     900
accatcatgc gcgtggtgga gctctcgccc ctgaagggct cggtgtcgtg gacggggaag     960
ccagtctcct actacctgca cactatcgac cgcaccatac ttgaaaacta tttttctagt    1020
ctgaaaaacc caaaactcag ggaggaacag gaggcagccc ggcgccgcca gcagcgcgag    1080
agcaagagca acgcggccac gcccactaag ggcccagagg gcaaggtggc cggccccgcc    1140
gacgccccca tggactctgg tgctgaggaa gagaaggcgg gagcagccac cgtgaagaag    1200
ccgtctccct ccaaagcccg caagaagaag ctaaacaaga aggggaggaa gatggctggc    1260
cgcaagcgcg ggcgccccaa gaagatgaac actgcgaacc ccgagcggaa gcccaagaag    1320
aaccaaactg cactggatgc cctgcacgct cagaccgtgt ctcagacggc ggcctcctca    1380
ccccaggatg cctacagatc ccctcacagc ccgttctacc agctacctcc gagcgtgcag    1440
cggcactccc ccaacccgct gctggtggcg cccacccgc ccgcgctgca gaagcttcta    1500
gagtccttca gatccagta cctgcagttc ctggcataca caaagacccc ccagtacaag    1560
gccagcctgc aggagctgct gggccaggag aaggagaaga acgcccagct cctgggtgcg    1620
gctcagcagc tcctcagcca ctgccaggcc cagaaggagg agatcaggag gctgtttcag    1680
caaaaattgg atgagctggg tgtgaaggcg ctgacctaca acgacctgat tcaagcgcag    1740
```

```
aaggagatct ccgcccataa ccagcagctg cgggagcagt cggagcagct ggagcaggac    1800
aaccgcgcgc tccgcggcca gagcttgcag ctgctcaagg ctcgctgcga ggagctgcag    1860
ctggactggg ccacgctgtc gctggagaag ctgttgaagg agaagcaggc cctgaagagc    1920
cagatctcgg agaagcagag gcactgcctg gagctgcaga tcagcattgt ggagctagag    1980
aagagccagc ggcagcagga gctcctgcag ctcaagtcct gtgtgccgcc tgacgacgcc    2040
ctgtccctgc acctgcgtgg aagggcgcc ctgggccgcg agctggagcc tgacgccagc    2100
cggctgcacc tggagctgga ctgcaccaag ttctcgctgc ctcacttgag cagcatgagc    2160
ccggagctct ccatgaacgg ccaggctgct ggctatgagc tctgcggtgt gctgagccgg    2220
ccttcgtcga agcagaacac gccccagtac ctggcctcac ccctggacca ggaggtggtg    2280
ccctgtaccc ctagccacgt cggccggccg cgcctggaga agctgtctgg cctagccgca    2340
cccgactaca ctaggctgtc cccggccaag attgtgctga gcggcacct gagccaggac    2400 cacacggtgc ccggcaggcc ggctgccagt gagctgcatt cgagagctga gcacaccaag    2460
gagaacggcc ttccctacca gagccccagc gtgcctggca gcatgaagct gagccctcag    2520
gacccgcggc ccctgtcccc tggggccttg cagcttgctg gagagaagag cagtgagaag    2580
ggcctgagag agcgcgccta cggcagcagc ggggagctca tcaccagcct gcccatcagc    2640
atcccgctca gcaccgtgca gcccaacaag ctcccggtca gcattcccct ggccagcgtg    2700
gtgctgccca gccgcgccga gagggcgagg agcaccccca gtcccgtgct gcagccccgt    2760 gaccccctcgt ccacacttga aaagcagatt ggtgctaatg cccacggtgc tgggagcaga    2820
agccttgccc tggcccccgc aggcttctcc tacgctggct cggtggccat cagcggggcc    2880
ttggcgggca gcccggcctc tctcacacct ggagccgagc cggccacctt ggatgagtcc    2940
tccagctctg ggagccttt tgccaccgtg gggtcccgca gctccacgcc acagcacccc    3000
ctgctgctgg cacagccccg gaactcgctt cctgcctctc ccgcccacca gctctcctcc    3060
agtccccggc ttggtggggc cgcccagggc ccgttgcccg aggccagcaa gggagacctg    3120
ccctccgatt ccggcttctc agatcctgag agtgaagcca agaggaggat tgtgttcacc    3180
atcaccactg gtgcgggcag tgccaagcag tcgccctcca gcaagcacag ccccctgacc    3240
gccagcgccc gtgggggactg tgtgccgagc cacgggcagg acagtcgcag gcgcggccgg    3300
cggaagcgag catctgcggg gacgcccagc ttgagcgcag gcgtgtcccc caagcgccga    3360
gccctgccgt ccgtcgctgg cctttttcaca cagccttcgg ggtctcccct caacctcaac    3420
tccatggtca gtaacatcaa ccagcccctg gagattacag ccatctcgtc cccggagacc    3480
tccctgaaga gctcccctgt gccctaccag gaccacgacc agccccccgt gctcaagaag    3540
gagcggcctc tgagccagac caatggggca cactactccc cactcacctc agacgaggag    3600
ccaggctctg aggacgagcc cagcagtgct cgaattgaga gaaaaattgc aacaatctcc    3660
ttagaaagca aatctccccc gaaaaccttg gaaaatggtg gtggcttggc gggaaggaag    3720
cccgcgcccg ccggcgagcc agtcaatagc agcaagtgga gtccaccctt ctcgcccatc    3780
tccgacatcg gcctggccaa gtcggcggac agcccgctgc aggccagctc cgcccctcagc    3840 cagaactccc tgttcacgtt ccggcccgcc ctgaggagc cctctgccga tgccaagctg    3900
gccgctcacc ccaggaaagg ctttcccggc tccctgtcgg gggctgacgg actcagcccg    3960
ggcaccaacc ctgccaacgg ctgcaccttc ggcggggcc tggccgcgga cctgagtttta   4020 cacagcttca gtgatggtgc ttctcttccc cacaagggcc ccgaggcggc cggcctgagc    4080
```

-continued

```
tccccgctga gcttcccctc gcagcgcggc aaggagggct cggacgccaa cccttcctg      4140 agcaagaggc agctggacgg cctggctggg ctgaagggcg agggcagccg cggcaaggag      4200
gcaggggagg gcggcctacc gctgtgcggg cccacggaca agaccccact gctgagcggc      4260
aaggccgcca aggcccggga ccgcgaggtc gacctcaaga atggccacaa cctcttcatc      4320
tctgcggcgg ccgtgcctcc cggaagcctc ctcagcggcc ccggcctggc cccggcggcg      4380
tcctccgcag gcggcgcggc gtcctccgcc cagacgcacc ggtccttcct gggccccttc      4440
ccgccgggac cgcagttcgc gctcggcccc atgtccctgc aggccaacct cggctccgtg      4500
gccggctcct ccgtgctgca gtcgctgttc agctctgtgc cggccgccgc aggcctggtg      4560
cacgtgtcgt ccgctgccac cagactgacc aactcgcacg ccatgggcag cttttccggg      4620
gtggcaggcg gcacagttgg aggtaactag gatttctacc tcaaccgcga gacctatgca      4680
aggacggtgt ggaccaactc gcgccgcgg catggtgccc gccggcctgc cgggctccca      4740
cccctggacg gcagaggcaa ggacggacgg gagctccact gtgaatcggc ggcacgcgcc      4800
gcaggaggct gggactggtc cagtttgtac tgtcgatagt tttagataaa gtatttatca      4860 tttttttaaaa agtaaaaaaa aaaaaaaaa                                       4889

<210> SEQ ID NO 2
<211> LENGTH: 1537
<212> TYPE: PRT
<213> ORGANISM: Homo sapiens

<400> SEQUENCE: 2

Met Gly Glu Lys Leu Glu Leu Arg Leu Lys Ser Pro Val Gly Ala Glu
1               5                   10                  15

Pro Ala Val Tyr Pro Trp Pro Leu Pro Val Tyr Asp Lys His His Asp
            20                  25                  30

Ala Ala His Glu Ile Ile Glu Thr Ile Arg Trp Val Cys Glu Glu Ile
        35                  40                  45

Pro Asp Leu Lys Leu Ala Met Glu Asn Tyr Val Leu Ile Asp Tyr Asp
    50                  55                  60

Thr Lys Ser Phe Glu Ser Met Gln Arg Leu Cys Asp Lys Tyr Asn Arg
65                  70                  75                  80

Ala Ile Asp Ser Ile His Gln Leu Trp Lys Gly Thr Thr Gln Pro Met
                85                  90                  95

Lys Leu Asn Thr Arg Pro Ser Thr Gly Leu Leu Arg His Ile Leu Gln
            100                 105                 110

Gln Val Tyr Asn His Ser Val Thr Asp Pro Glu Lys Leu Asn Asn Tyr
        115                 120                 125

Glu Pro Phe Ser Pro Glu Val Tyr Gly Glu Thr Ser Phe Asp Leu Val
    130                 135                 140

Ala Gln Met Ile Asp Glu Ile Lys Met Thr Asp Asp Leu Phe Val
145                 150                 155                 160

Asp Leu Gly Ser Gly Val Gly Gln Val Val Leu Gln Val Ala Ala Ala
                165                 170                 175

Thr Asn Cys Lys His His Tyr Gly Val Glu Lys Ala Asp Ile Pro Ala
            180                 185                 190

Lys Tyr Ala Glu Thr Met Asp Arg Glu Phe Arg Lys Trp Met Lys Trp
        195                 200                 205

Tyr Gly Lys Lys His Ala Glu Tyr Thr Leu Glu Arg Gly Asp Phe Leu
    210                 215                 220

Ser Glu Glu Trp Arg Glu Arg Ile Ala Asn Thr Ser Val Ile Phe Val
```

```
            225                 230                 235                 240
        Asn Asn Phe Ala Phe Gly Pro Glu Val Asp His Gln Leu Lys Glu Arg
                    245                 250                 255
        Phe Ala Asn Met Lys Glu Gly Gly Arg Ile Val Ser Ser Lys Pro Phe
                    260                 265                 270
        Ala Pro Leu Asn Phe Arg Ile Asn Ser Arg Asn Leu Ser Asp Ile Gly
                    275                 280                 285
        Thr Ile Met Arg Val Val Glu Leu Ser Pro Leu Lys Gly Ser Val Ser
            290                 295                 300
        Trp Thr Gly Lys Pro Val Ser Tyr Tyr Leu His Thr Ile Asp Arg Thr
        305                 310                 315                 320
        Ile Leu Glu Asn Tyr Phe Ser Ser Leu Lys Asn Pro Lys Leu Arg Glu
                    325                 330                 335
        Glu Gln Glu Ala Ala Arg Arg Arg Gln Gln Arg Glu Ser Lys Ser Asn
                    340                 345                 350
        Ala Ala Thr Pro Thr Lys Gly Pro Glu Gly Lys Val Ala Gly Pro Ala
                    355                 360                 365
        Asp Ala Pro Met Asp Ser Gly Ala Glu Glu Lys Ala Gly Ala Ala
            370                 375                 380
        Thr Val Lys Lys Pro Ser Pro Ser Lys Ala Arg Lys Lys Leu Asn
        385                 390                 395                 400
        Lys Lys Gly Arg Lys Met Ala Gly Arg Lys Arg Gly Arg Pro Lys Lys
                    405                 410                 415
        Met Asn Thr Ala Asn Pro Glu Arg Lys Pro Lys Lys Asn Gln Thr Ala
                    420                 425                 430
        Leu Asp Ala Leu His Ala Gln Thr Val Ser Gln Thr Ala Ala Ser Ser
                    435                 440                 445
        Pro Gln Asp Ala Tyr Arg Ser Pro His Ser Pro Phe Tyr Gln Leu Pro
            450                 455                 460
        Pro Ser Val Gln Arg His Ser Pro Asn Pro Leu Val Ala Pro Thr
        465                 470                 475                 480
        Pro Pro Ala Leu Gln Lys Leu Leu Glu Ser Phe Lys Ile Gln Tyr Leu
                    485                 490                 495
        Gln Phe Leu Ala Tyr Thr Lys Thr Pro Gln Tyr Lys Ala Ser Leu Gln
                    500                 505                 510
        Glu Leu Leu Gly Gln Glu Lys Glu Lys Asn Ala Gln Leu Leu Gly Ala
            515                 520                 525
        Ala Gln Gln Leu Leu Ser His Cys Gln Ala Gln Lys Glu Glu Ile Arg
            530                 535                 540
        Arg Leu Phe Gln Gln Lys Leu Asp Glu Leu Gly Val Lys Ala Leu Thr
        545                 550                 555                 560
        Tyr Asn Asp Leu Ile Gln Ala Gln Lys Glu Ile Ser Ala His Asn Gln
                    565                 570                 575
        Gln Leu Arg Glu Gln Ser Glu Gln Leu Glu Gln Asp Asn Arg Ala Leu
                    580                 585                 590
        Arg Gly Gln Ser Leu Gln Leu Leu Lys Ala Arg Cys Glu Glu Leu Gln
                    595                 600                 605
        Leu Asp Trp Ala Thr Leu Ser Leu Glu Lys Leu Leu Lys Glu Lys Gln
            610                 615                 620
        Ala Leu Lys Ser Gln Ile Ser Glu Lys Gln Arg His Cys Leu Glu Leu
        625                 630                 635                 640
        Gln Ile Ser Ile Val Glu Leu Glu Lys Ser Gln Arg Gln Gln Glu Leu
                    645                 650                 655
```

-continued

```
Leu Gln Leu Lys Ser Cys Val Pro Pro Asp Ala Leu Ser Leu His
            660                 665                 670

Leu Arg Gly Lys Gly Ala Leu Gly Arg Glu Leu Glu Pro Asp Ala Ser
            675                 680                 685

Arg Leu His Leu Glu Leu Asp Cys Thr Lys Phe Ser Leu Pro His Leu
            690                 695                 700

Ser Ser Met Ser Pro Glu Leu Ser Met Asn Gly Gln Ala Ala Gly Tyr
705                 710                 715                 720

Glu Leu Cys Gly Val Leu Ser Arg Pro Ser Lys Gln Asn Thr Pro
                725                 730                 735

Gln Tyr Leu Ala Ser Pro Leu Asp Gln Glu Val Val Pro Cys Thr Pro
            740                 745                 750

Ser His Val Gly Arg Pro Arg Leu Glu Lys Leu Ser Gly Leu Ala Ala
            755                 760                 765

Pro Asp Tyr Thr Arg Leu Ser Pro Ala Lys Ile Val Leu Arg Arg His
            770                 775                 780

Leu Ser Gln Asp His Thr Val Pro Gly Arg Pro Ala Ala Ser Glu Leu
785                 790                 795                 800

His Ser Arg Ala Glu His Thr Lys Glu Asn Gly Leu Pro Tyr Gln Ser
                805                 810                 815

Pro Ser Val Pro Gly Ser Met Lys Leu Ser Pro Gln Asp Pro Arg Pro
            820                 825                 830

Leu Ser Pro Gly Ala Leu Gln Leu Ala Gly Glu Lys Ser Ser Glu Lys
            835                 840                 845

Gly Leu Arg Glu Arg Ala Tyr Gly Ser Ser Gly Glu Leu Ile Thr Ser
850                 855                 860

Leu Pro Ile Ser Ile Pro Leu Ser Thr Val Gln Pro Asn Lys Leu Pro
865                 870                 875                 880

Val Ser Ile Pro Leu Ala Ser Val Val Leu Pro Ser Arg Ala Glu Arg
                885                 890                 895

Ala Arg Ser Thr Pro Ser Pro Val Leu Gln Pro Arg Asp Pro Ser Ser
            900                 905                 910

Thr Leu Glu Lys Gln Ile Gly Ala Asn Ala His Gly Ala Gly Ser Arg
            915                 920                 925

Ser Leu Ala Leu Ala Pro Ala Gly Phe Ser Tyr Ala Gly Ser Val Ala
            930                 935                 940

Ile Ser Gly Ala Leu Ala Gly Ser Pro Ala Ser Leu Thr Pro Gly Ala
945                 950                 955                 960

Glu Pro Ala Thr Leu Asp Glu Ser Ser Ser Gly Ser Leu Phe Ala
                965                 970                 975

Thr Val Gly Ser Arg Ser Ser Thr Pro Gln His Pro Leu Leu Leu Ala
            980                 985                 990

Gln Pro Arg Asn Ser Leu Pro Ala Ser Pro Ala His Gln Leu Ser Ser
            995                 1000                1005

Ser Pro Arg Leu Gly Gly Ala Ala Gln Gly Pro Leu Pro Glu Ala
            1010                1015                1020

Ser Lys Gly Asp Leu Pro Ser Asp Ser Gly Phe Ser Asp Pro Glu
            1025                1030                1035

Ser Glu Ala Lys Arg Arg Ile Val Phe Thr Ile Thr Thr Gly Ala
            1040                1045                1050

Gly Ser Ala Lys Gln Ser Pro Ser Ser Lys His Ser Pro Leu Thr
            1055                1060                1065
```

-continued

```
Ala Ser  Ala Arg Gly Asp Cys Val Pro Ser His Gly Gln Asp Ser
    1070         1075            1080

Arg Arg  Arg Gly Arg Arg Lys Arg Ala Ser Ala Gly Thr Pro Ser
    1085         1090            1095

Leu Ser  Ala Gly Val Ser Pro Lys Arg Arg Ala Leu Pro Ser Val
    1100         1105            1110

Ala Gly  Leu Phe Thr Gln Pro Ser Gly Ser Pro Leu Asn Leu Asn
    1115         1120            1125

Ser Met  Val Ser Asn Ile Asn Gln Pro Leu Glu Ile Thr Ala Ile
    1130         1135            1140

Ser Ser  Pro Glu Thr Ser Leu Lys Ser Ser Pro Val Pro Tyr Gln
    1145         1150            1155

Asp His  Asp Gln Pro Pro Val Leu Lys Lys Glu Arg Pro Leu Ser
    1160         1165            1170

Gln Thr  Asn Gly Ala His Tyr Ser Pro Leu Thr Ser Asp Glu Glu
    1175         1180            1185

Pro Gly  Ser Glu Asp Glu Pro Ser Ser Ala Arg Ile Glu Arg Lys
    1190         1195            1200

Ile Ala  Thr Ile Ser Leu Glu Ser Lys Ser Pro Pro Lys Thr Leu
    1205         1210            1215

Glu Asn  Gly Gly Gly Leu Ala Gly Arg Lys Pro Ala Pro Ala Gly
    1220         1225            1230

Glu Pro  Val Asn Ser Ser Lys Trp Lys Ser Thr Phe Ser Pro Ile
    1235         1240            1245

Ser Asp  Ile Gly Leu Ala Lys Ser Ala Asp Ser Pro Leu Gln Ala
    1250         1255            1260

Ser Ser  Ala Leu Ser Gln Asn Ser Leu Phe Thr Phe Arg Pro Ala
    1265         1270            1275

Leu Glu  Glu Pro Ser Ala Asp Ala Lys Leu Ala Ala His Pro Arg
    1280         1285            1290

Lys Gly  Phe Pro Gly Ser Leu Ser Gly Ala Asp Gly Leu Ser Pro
    1295         1300            1305

Gly Thr  Asn Pro Ala Asn Gly Cys Thr Phe Gly Gly Gly Leu Ala
    1310         1315            1320

Ala Asp  Leu Ser Leu His Ser Phe Ser Asp Gly Ala Ser Leu Pro
    1325         1330            1335

His Lys  Gly Pro Glu Ala Ala Gly Leu Ser Ser Pro Leu Ser Phe
    1340         1345            1350

Pro Ser  Gln Arg Gly Lys Glu Gly Ser Asp Ala Asn Pro Phe Leu
    1355         1360            1365

Ser Lys  Arg Gln Leu Asp Gly Leu Ala Gly Leu Lys Gly Glu Gly
    1370         1375            1380

Ser Arg  Gly Lys Glu Ala Gly Glu Gly Gly Leu Pro Leu Cys Gly
    1385         1390            1395

Pro Thr  Asp Lys Thr Pro Leu Leu Ser Gly Lys Ala Ala Lys Ala
    1400         1405            1410

Arg Asp  Arg Glu Val Asp Leu Lys Asn Gly His Asn Leu Phe Ile
    1415         1420            1425

Ser Ala  Ala Val Pro Pro Gly Ser Leu Leu Ser Gly Pro Gly
    1430         1435            1440

Leu Ala  Pro Ala Ala Ser Ala Gly Gly Ala Ala Ser Ser Ala
    1445         1450            1455

Gln Thr  His Arg Ser Phe Leu Gly Pro Phe Pro Pro Gly Pro Gln
```

-continued

```
      1460              1465               1470
Phe Ala Leu Gly Pro Met Ser Leu Gln Ala Asn Leu Gly Ser Val
        1475                1480                1485
Ala Gly Ser Ser Val Leu Gln Ser Leu Phe Ser Ser Val Pro Ala
        1490                1495                1500
Ala Ala Gly Leu Val His Val Ser Ser Ala Ala Thr Arg Leu Thr
        1505                1510                1515
Asn Ser His Ala Met Gly Ser Phe Ser Gly Val Ala Gly Gly Thr
        1520                1525                1530
Val Gly Gly Asn
        1535

<210> SEQ ID NO 3
<211> LENGTH: 53
<212> TYPE: PRT
<213> ORGANISM: Homo sapiens

<400> SEQUENCE: 3

Arg Lys Leu Pro Phe Gln Arg Leu Val Arg Glu Ile Ala Gln Asp Phe
1               5                   10                  15

Lys Thr Asp Leu Arg Phe Gln Ser Ala Ala Ile Gly Ala Leu Gln Glu
            20                  25                  30

Ala Ser Glu Ala Tyr Leu Val Gly Leu Phe Glu Asp Thr Asn Leu Cys
        35                  40                  45

Ala Ile His Ala Lys
    50

<210> SEQ ID NO 4
<211> LENGTH: 11
<212> TYPE: PRT
<213> ORGANISM: Homo sapiens

<400> SEQUENCE: 4

Ile Ala Gln Asp Phe Lys Thr Asp Leu Arg Phe
1               5                   10

<210> SEQ ID NO 5
<211> LENGTH: 293
<212> TYPE: PRT
<213> ORGANISM: Saccharomyces cerevisiae

<400> SEQUENCE: 5

Glu Thr Ile Leu Pro Asp Leu Asn Ala Ser Phe Asp Asn Ser Asp Thr
1               5                   10                  15

Lys Gly Phe Val Asn Ala Ile Asn Leu Tyr Asn Lys Met Ile Arg Glu
            20                  25                  30

Ile Pro Arg Gln Arg Ile Ile Asp His Leu Glu Thr Ile Asp Lys Ile
        35                  40                  45

Pro Arg Ser Phe Ile His Asp Phe Leu His Ile Val Tyr Thr Arg Ser
    50                  55                  60

Ile His Pro Gln Ala Asn Lys Leu Lys His Tyr Lys Ala Phe Ser Asn
65                  70                  75                  80

Tyr Val Tyr Gly Glu Leu Leu Pro Asn Phe Leu Ser Asp Val Tyr Gln
            85                  90                  95

Gln Cys Gln Leu Lys Lys Gly Asp Thr Phe Met Asp Leu Gly Ser Gly
            100                 105                 110

Val Gly Asn Cys Val Val Gln Ala Ala Leu Glu Cys Gly Cys Ala Leu
        115                 120                 125
```

```
Ser Phe Gly Cys Glu Ile Met Asp Asp Ala Ser Asp Leu Thr Ile Leu
            130                 135                 140

Gln Tyr Glu Glu Leu Lys Lys Arg Cys Lys Leu Tyr Gly Met Arg Leu
145                 150                 155                 160

Asn Asn Val Glu Phe Ser Leu Lys Lys Ser Phe Val Asp Asn Asn Arg
                165                 170                 175

Val Ala Glu Leu Ile Pro Gln Cys Asp Val Ile Leu Val Asn Asn Phe
            180                 185                 190

Leu Phe Asp Glu Asp Leu Asn Lys Lys Val Glu Lys Ile Leu Gln Thr
        195                 200                 205

Ala Lys Val Gly Cys Lys Ile Ile Ser Leu Lys Ser Leu Arg Ser Leu
    210                 215                 220

Thr Tyr Gln Ile Asn Phe Tyr Asn Val Glu Asn Ile Phe Asn Arg Leu
225                 230                 235                 240

Lys Val Gln Arg Tyr Asp Leu Lys Glu Asp Ser Val Ser Trp Thr His
                245                 250                 255

Ser Gly Gly Glu Tyr Tyr Ile Ser Thr Val Met Glu Asp Val Asp Glu
            260                 265                 270

Ser Leu Phe Ser Pro Ala Ala Arg Gly Arg Arg Asn Arg Gly Thr Pro
        275                 280                 285

Val Lys Tyr Thr Arg
    290

<210> SEQ ID NO 6
<211> LENGTH: 292
<212> TYPE: PRT
<213> ORGANISM: Homo sapiens

<400> SEQUENCE: 6

Leu Ala Met Glu Asn Tyr Val Leu Ile Asp Tyr Asp Thr Lys Ser Phe
1               5                   10                  15

Glu Ser Met Gln Arg Leu Cys Asp Lys Tyr Asn Arg Ala Ile Asp Ser
            20                  25                  30

Ile His Gln Leu Trp Lys Gly Thr Gln Pro Met Lys Leu Asn Asn Thr
        35                  40                  45

Arg Pro Ser Thr Gly Leu Leu Arg His Ile Leu Gln Gln Val Tyr Asn
    50                  55                  60

His Ser Val Thr Asp Pro Glu Lys Leu Asn Asn Tyr Glu Pro Phe Ser
65                  70                  75                  80

Pro Glu Val Tyr Gly Glu Thr Ser Phe Asp Leu Val Ala Gln Met Ile
                85                  90                  95

Asp Glu Ile Lys Met Thr Asp Asp Leu Phe Val Asp Leu Gly Ser
            100                 105                 110

Gly Val Gly Gln Val Val Leu Gln Val Ala Ala Ala Thr Asn Cys Lys
        115                 120                 125

His His Tyr Gly Val Glu Lys Ala Asp Ile Pro Ala Lys Tyr Ala Glu
    130                 135                 140

Thr Met Asp Arg Glu Phe Arg Lys Trp Met Lys Trp Tyr Gly Lys Lys
145                 150                 155                 160

His Ala Glu Tyr Thr Leu Glu Arg Gly Asp Phe Leu Ser Glu Glu Trp
                165                 170                 175

Arg Glu Arg Ile Ala Asn Thr Ser Val Ile Phe Val Asn Asn Phe Ala
            180                 185                 190

Phe Gly Pro Glu Val Asp His Gln Leu Lys Glu Arg Phe Ala Asn Met
```

```
                195                 200                 205
Lys Glu Gly Gly Arg Ile Val Ser Ser Lys Pro Phe Ala Pro Leu Asn
    210                 215                 220

Phe Arg Ile Asn Ser Arg Asn Leu Ser Asp Ile Gly Thr Ile Met Arg
225                 230                 235                 240

Val Val Glu Leu Ser Pro Leu Lys Gly Ser Val Ser Trp Thr Gly Lys
                245                 250                 255

Pro Val Ser Tyr Tyr Leu His Thr Ile Asp Arg Thr Ile Leu Glu Asn
                260                 265                 270

Tyr Phe Ser Ser Leu Lys Asn Pro Lys Leu Arg Glu Glu Gln Glu Ala
                275                 280                 285

Ala Arg Arg Arg
    290

<210> SEQ ID NO 7
<211> LENGTH: 293
<212> TYPE: PRT
<213> ORGANISM: Drosophila melanogaster

<400> SEQUENCE: 7

Ser Ala Phe Glu Glu Thr Asn Leu His Gln Ile Asp Thr Ala Cys Tyr
1               5                   10                  15

Lys Thr Met Thr Gly Leu Val Asp Arg Phe Asn Lys Ala Val Asp Ser
                20                  25                  30

Ile Val Ala Leu Glu Lys Gly Thr Ser Leu Pro Ala Glu Arg Leu Asn
            35                  40                  45

Lys Phe Ala His Pro Ser Leu Leu Arg His Ile Leu Gln Leu Val Tyr
        50                  55                  60

Asn Ala Ala Val Leu Asp Pro Asp Lys Leu Asn Gln Tyr Glu Pro Phe
65                  70                  75                  80

Ser Pro Glu Val Tyr Gly Glu Thr Ser Tyr Glu Leu Val Gln Gln Met
                85                  90                  95

Leu Lys His Val Thr Val Ser Lys Glu Asp Thr Phe Ile Asp Leu Gly
            100                 105                 110

Ser Gly Val Gly Gln Val Val Leu Gln Met Ala Gly Ser Phe Pro Leu
        115                 120                 125

Lys Thr Cys Ile Gly Ile Glu Lys Ala Asp Thr Pro Ala Arg Tyr Ala
    130                 135                 140

Glu Arg Met Asp Val Ile Phe Arg Gln Tyr Met Gly Trp Phe Gly Lys
145                 150                 155                 160

Arg Phe Cys Glu Tyr Lys Leu Ile Lys Gly Asp Phe Leu Val Asp Glu
                165                 170                 175

His Arg Glu Asn Ile Thr Ser Ser Thr Leu Val Phe Val Asn Asn Phe
                180                 185                 190

Ala Phe Gly Pro Thr Val Asp His Gln Leu Lys Glu Arg Phe Ala Asp
            195                 200                 205

Leu Arg Asp Gly Ala Arg Val Val Ser Ser Lys Ser Phe Cys Pro Leu
    210                 215                 220

Asn Phe Arg Ile Thr Asp Arg Asn Leu Ser Asp Ile Gly Thr Ile Met
225                 230                 235                 240

His Val Ser Glu Ile Pro Pro Leu Lys Gly Ser Val Ser Trp Thr Cys
                245                 250                 255

Lys Pro Val Ser Tyr Tyr Leu His Val Ile Asp Arg Thr Ile Leu Glu
                260                 265                 270
```

-continued

```
Arg Tyr Phe Gln Arg Leu Lys Thr Lys Gly Gly Asn Asp His Glu Ser
        275                 280                 285
Val Gly Thr Val Arg
    290

<210> SEQ ID NO 8
<211> LENGTH: 278
<212> TYPE: PRT
<213> ORGANISM: Caenorhabditis elegans

<400> SEQUENCE: 8

Val Pro Leu Pro Ser Asp Ala Val Gly Asn Pro Lys Phe Ser
1               5                   10                  15

Gln Tyr Ile Asp Ala Leu Asn Leu Lys Leu Ala His Pro Asp Val Leu
            20                  25                  30

Ser Arg Val Pro Ala Lys His His Glu Ile Thr Ser Thr Arg Leu Cys
        35                  40                  45

Ser Leu Thr Val Ala Ile Lys Leu Ala Glu Leu Ala Tyr Arg Phe Ser
    50                  55                  60

Val Pro Asp Ala Asn Val Leu Arg His Tyr Ala Val Gly Thr Ser Thr
65                  70                  75                  80

Val Tyr Gly Glu Leu His Cys Ser Gln Met Ala Ser Phe Val Asp Gln
                85                  90                  95

Leu Asn Met Gly Pro Ser Asp Tyr Phe Met Asp Leu Gly Ser Gly Ile
            100                 105                 110

Gly His Leu Val Asn Phe Val Ala Ala Tyr Ala Arg Thr Gln Met Ser
        115                 120                 125

Val Gly Val Glu Leu Met Asp Asn Leu Ala Glu Ile Ala Glu Lys Asn
    130                 135                 140

Lys Glu Phe Asn Glu Arg Leu Leu Asn His Phe Gly Lys Lys Val Tyr
145                 150                 155                 160

Ala Thr Arg Phe Ile His Gly Ser Phe Thr Ser Pro Ala Val Ile Arg
                165                 170                 175

Glu Ile Gln Thr Lys Ala Thr Val Ile Leu Ala Asn Asn Val Arg Phe
            180                 185                 190

Asp Pro Glu Leu Lys Leu Gln Leu Lys Glu Ile Leu Met Gly Cys Lys
        195                 200                 205

Asp Arg Thr Arg Ile Ile Ser Ser Glu Pro Leu Val Pro Ser Arg Ala
    210                 215                 220

Arg Gln Thr Asn Ser Arg Arg Ala Asp Asp Phe Val Lys Ile Ser Asp
225                 230                 235                 240

Glu Ser Leu Leu Asn Leu Val Asp Asn Asn Val Ser Trp Thr Ser Arg
                245                 250                 255

Lys Val Pro Phe Tyr Leu Thr Thr Ile Asn Arg Asn Lys Val Ser Phe
            260                 265                 270

Phe Tyr Cys Val Arg Phe
        275

<210> SEQ ID NO 9
<211> LENGTH: 56
<212> TYPE: PRT
<213> ORGANISM: Homo sapiens

<400> SEQUENCE: 9

Glu Gly Lys Val Ala Gly Pro Ala Asp Ala Pro Met Asp Ser Gly Ala
1               5                   10                  15
```

```
Glu Glu Glu Lys Ala Gly Ala Ala Thr Val Lys Lys Pro Ser Pro Ser
        20                  25                  30

Lys Ala Arg Lys Lys Leu Asn Lys Lys Gly Arg Lys Met Ala Gly
        35                  40                  45

Arg Lys Arg Gly Arg Pro Lys Lys
    50                  55
```

<210> SEQ ID NO 10
<211> LENGTH: 58
<212> TYPE: PRT
<213> ORGANISM: Saccharomyces cerevisiae

<400> SEQUENCE: 10

```
Lys Gly Lys Asp Asn Gly Leu Val Pro Leu Val Glu Lys Val Ile Pro
1               5                   10                  15

Pro Ile His Lys Lys Thr Asn Arg Asn Thr Arg Lys Lys Ser Ser
        20                  25                  30

Thr Thr Thr Lys Lys Asp Val Lys Pro Lys Ala Ala Lys Val Lys
        35                  40                  45

Gly Lys Asn Gly Arg Thr Asn His Lys His
    50                  55
```

<210> SEQ ID NO 11
<211> LENGTH: 15
<212> TYPE: PRT
<213> ORGANISM: Homo sapiens

<400> SEQUENCE: 11

```
Asn Glu Leu Ala Leu Lys Leu Ala Gly Leu Asp Ile Asn Lys Thr
1               5                   10                  15
```

<210> SEQ ID NO 12
<211> LENGTH: 15
<212> TYPE: PRT
<213> ORGANISM: Homo sapiens

<400> SEQUENCE: 12

```
Pro Ala Leu Gln Lys Leu Leu Glu Ser Phe Lys Ile Gln Tyr Leu
1               5                   10                  15
```

<210> SEQ ID NO 13
<211> LENGTH: 15
<212> TYPE: PRT
<213> ORGANISM: Homo sapiens

<400> SEQUENCE: 13

```
His Cys Leu Glu Leu Gln Ile Ser Ile Val Glu Leu Glu Lys Ser
1               5                   10                  15
```

<210> SEQ ID NO 14
<211> LENGTH: 15
<212> TYPE: PRT
<213> ORGANISM: Homo sapiens

<400> SEQUENCE: 14

```
Pro Ala Leu Gln Lys Leu Leu Glu Ser Ala Lys Ala Gln Tyr Leu
1               5                   10                  15
```

<210> SEQ ID NO 15
<211> LENGTH: 66
<212> TYPE: PRT
<213> ORGANISM: Homo sapiens

<400> SEQUENCE: 15

Ala Ser Ile Glu Gln Leu Leu Glu Arg Gln Trp Ser Glu Gly Gln Gln
1               5                   10                  15

Phe Leu Leu Glu Gln Gly Thr Pro Ser Asp Ile Leu Gly Met Leu Lys
            20                  25                  30

Ser Leu His Gln Leu Gln Val Glu Asn Arg Arg Leu Glu Glu Gln Ile
        35                  40                  45

Lys Asn Leu Thr Ala Lys Lys Glu Arg Leu Gln Leu Leu Asn Ala Gln
    50                  55                  60

Leu Ser
65

<210> SEQ ID NO 16
<211> LENGTH: 66
<212> TYPE: PRT
<213> ORGANISM: Mus musculus

<400> SEQUENCE: 16

Ala Ser Ile Glu Gln Leu Leu Glu Arg Gln Trp Ser Glu Gly Gln Gln
1               5                   10                  15

Phe Leu Leu Glu Gln Gly Thr Pro Gly Asp Ile Leu Gly Met Leu Lys
            20                  25                  30

Ser Leu His Gln Leu Gln Val Glu Asn Arg Arg Leu Glu Glu Gln Ile
        35                  40                  45

Lys Asn Leu Thr Ala Lys Lys Glu Arg Leu Gln Leu Leu Asn Ala Gln
    50                  55                  60

Leu Ser
65

<210> SEQ ID NO 17
<211> LENGTH: 66
<212> TYPE: PRT
<213> ORGANISM: Drosophila melanogaster

<400> SEQUENCE: 17

Gln Ser Leu Glu Gln Leu Leu Glu Arg Gln Trp Glu Gln Gly Ser Gln
1               5                   10                  15

Phe Leu Met Glu Gln Ala Gln His Phe Asp Ile Ala Ser Leu Leu Asn
            20                  25                  30

Cys Leu His Gln Leu Gln Ser Glu Asn Leu Arg Leu Glu Glu His Val
        35                  40                  45

Thr Ser Leu Ile Ala Arg Arg Asp His Leu Leu Ala Val Asn Ala Arg
    50                  55                  60

Leu Gln
65

<210> SEQ ID NO 18
<211> LENGTH: 65
<212> TYPE: PRT
<213> ORGANISM: Caenorhabditis elegans

<400> SEQUENCE: 18

Ser Phe Met Glu Gln Leu Leu Glu Arg Gln Trp Asp Gln Gly Ser Ser
1               5                   10                  15

Leu Leu Met Ala Asn Ala His Phe Asp Val Ala Gln Leu Leu Ser Cys
            20                  25                  30

Leu Phe Gln Leu Lys Ser Glu Asn Phe Arg Leu Glu Glu Asn Leu Ser
        35                  40                  45

```
Gly Leu Arg Lys Arg Arg Asp His Leu Phe Ala Leu Asn Ser Arg Leu
    50                  55                  60

Ala
65

<210> SEQ ID NO 19
<211> LENGTH: 8
<212> TYPE: PRT
<213> ORGANISM: Artificial Sequence
<220> FEATURE:
<223> OTHER INFORMATION: Conserved octapeptide motif

<400> SEQUENCE: 19

Glu Gln Leu Leu Glu Arg Gln Trp
1               5

<210> SEQ ID NO 20
<211> LENGTH: 21
<212> TYPE: PRT
<213> ORGANISM: Artificial Sequence
<220> FEATURE:
<223> OTHER INFORMATION: Synthetic positively charged C-RS10 peptide

<400> SEQUENCE: 20

Cys Arg Ser Arg Ser Arg Ser Arg Ser Arg Ser Arg Ser Arg
1               5                   10                  15

Ser Arg Ser Arg Ser
        20

<210> SEQ ID NO 21
<211> LENGTH: 8
<212> TYPE: PRT
<213> ORGANISM: Artificial Sequence
<220> FEATURE:
<223> OTHER INFORMATION: SV40 T-antigen nuclear localization signal

<400> SEQUENCE: 21

Asp Pro Lys Lys Lys Arg Lys Val
1               5

<210> SEQ ID NO 22
<211> LENGTH: 12
<212> TYPE: PRT
<213> ORGANISM: Artificial Sequence
<220> FEATURE:
<223> OTHER INFORMATION: Concensus nuclear export signal
<220> FEATURE:
<221> NAME/KEY: MISC_FEATURE
<222> LOCATION: (2)..(2)
<223> OTHER INFORMATION: "Xaa" denotes 2 or 3 of any amino acid
<220> FEATURE:
<221> NAME/KEY: MISC_FEATURE
<222> LOCATION: (8)..(8)
<223> OTHER INFORMATION: "Xaa" denotes 2 or 3 of any amino acid
<220> FEATURE:
<221> NAME/KEY: MISC_FEATURE
<222> LOCATION: (10)..(10)
<223> OTHER INFORMATION: "Xaa" denotes any amino acid

<400> SEQUENCE: 22

Leu Xaa Leu Ile Val Phe Met Xaa Leu Xaa Leu Ile
1               5                   10
```